(12) United States Patent
Berg et al.

(10) Patent No.: US 6,410,532 B2
(45) Date of Patent: Jun. 25, 2002

(54) SUBSTITUTED 1,2,3,4-TETRAHYDRONAPHTHALENE DERIVATIVES

(75) Inventors: Stefan Berg, Ekero; Mats Linderberg; Svante Ross, both of Södertälje; Seth-Olov Thorberg, Strängnäs; Bengt Ulff, Södertälje, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/902,000

(22) Filed: Jul. 10, 2001

Related U.S. Application Data

(62) Division of application No. 09/171,577, filed as application No. PCT/SE98/01390 on Jul. 15, 1998, now Pat. No. 6,313,118.

(30) Foreign Application Priority Data

Jul. 25, 1997  (SE) ............................................. 9702799

(51) Int. Cl.[7] ................ C07D 295/135; C07D 295/155; C07D 211/26; A61K 31/495; A61K 31/445
(52) U.S. Cl. .................... 514/235.5; 544/130; 514/331; 546/216
(58) Field of Search ....................... 544/130; 514/235.5, 514/331; 546/216

(56) References Cited

U.S. PATENT DOCUMENTS 5,196,454 A   3/1993   Crauert et al. .............. 514/654

FOREIGN PATENT DOCUMENTS

| EP | 402923 | 12/1990 |
|----|--------|---------|
| EP | 533266 | 3/1993 |
| EP | 533267 | 3/1993 |
| EP | 533268 | 3/1993 |
| GB | 2273930 | 7/1994 |
| WO | 9413659 | 6/1994 |
| WO | 9421619 | 9/1994 |
| WO | 9511243 | 4/1995 |
| WO | 9734883 | 9/1997 |

Primary Examiner—Richard L. Raymond
Assistant Examiner—Hong Liu
(74) Attorney, Agent, or Firm—White & Case LLP

(57) ABSTRACT

The present invention relates to new piperidyl- or piperazinyl-substituted-1,2,3,4-tetrahydronaphthalene derivatives having the formula I

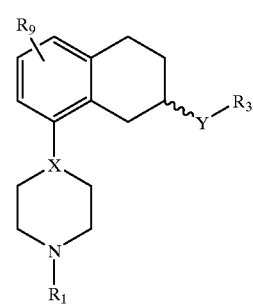

(I)

wherein
X is N or CH;
Y is $NR_2CH_2$, $CH_2$—$NR_2$, $NR_2$—CO, CO—$NR_2$ or $NR_2SO_2$ wherein $R_2$ is H or $C_{1-6}$ alkyl;
$R_1$ is H, $C_1$–$C_6$ alkyl or $C_3$–$C_6$ cycloalkyl;
$R_3$ is $C_1$–$C_6$ alkyl, $C_3$–$C_6$ cycloalkyl or $(CH_2)_n$-aryl, wherein aryl is phenyl or a heteroaromatic ring containing one or two heteroatoms selected from N, O and S and which may be mono- or di-substituted
n is 0–4;
$R_9$ is $C_1$–$C_6$ alkyl, $C_3$–$C_6$ cycloalkyl, $OCF_3$, $OCHF_2$, $OCH_2F$, halogen, CN, $CF_3$, OH, $C_1$–$C_6$ alkoxy, $C_1$–$C_6$ alkoxy—$C_1$–$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent(s) is(are) $C_1$–$C_6$ alkyl; or $COR_8$; wherein $R_6$, $R_7$ and $R_8$ are as defined above,
as (R)-enantiomers, (S)-enantiomers or racemates in the form of a free base or pharmaceutically acceptable salts thereof, a process for their preparation, pharmaceutical compositions containing said therapeutically active compounds and to the use of said active compounds in therapy.

22 Claims, 1 Drawing Sheet

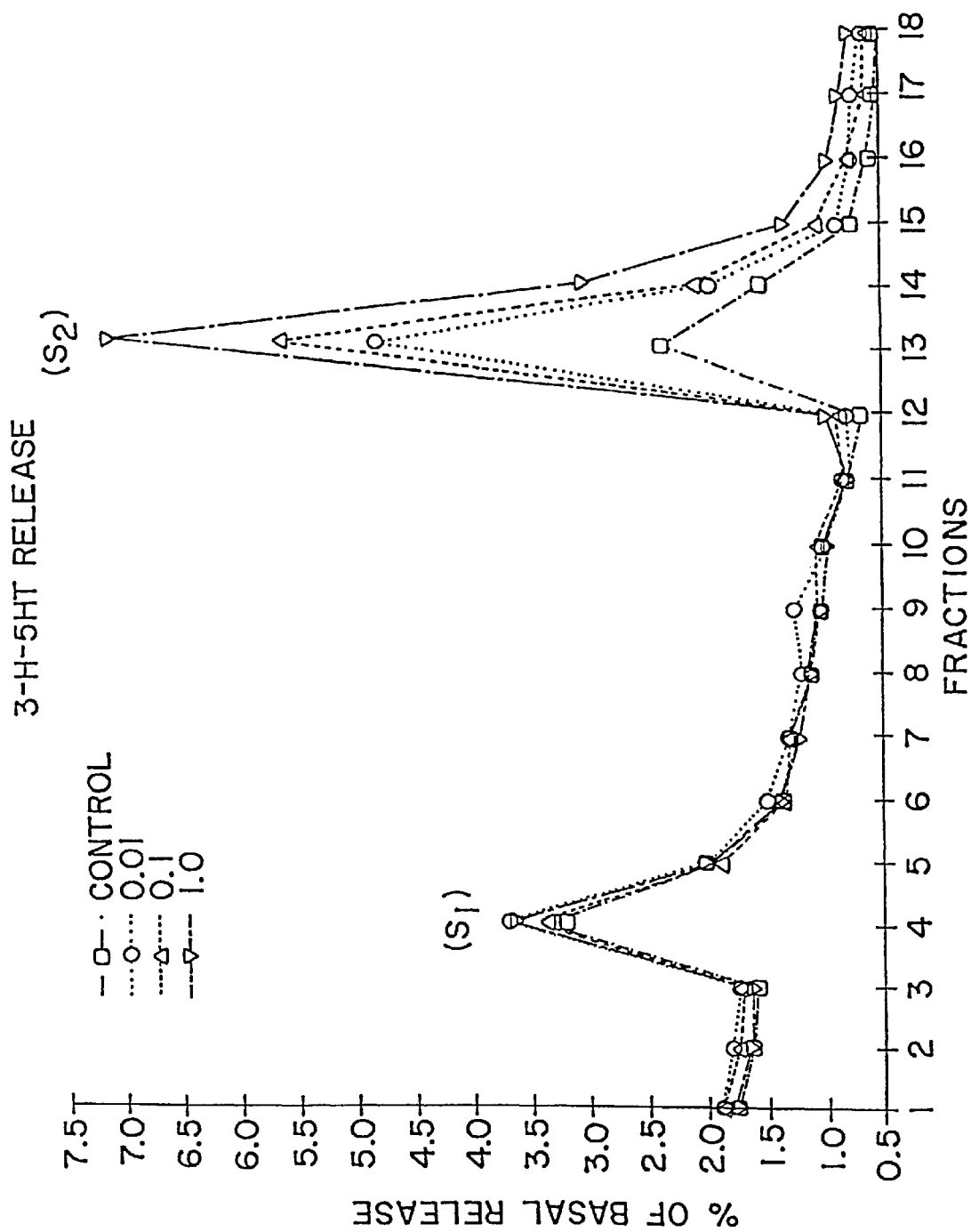

SUBSTITUTED 1,2,3,4-TETRAHYDRONAPHTHALENE DERIVATIVES

This application is a divisional of U.S. application Ser. No. 09/171,577, filed Oct. 21, 1998, U.S. Pat. No. 6,313,118, which was the National Stage of International application Ser. No. PCT/SE98/01390, filed Jul. 15, 1998.

FIELD OF THE INVENTION

The present invention relates to new piperidyl- or piperazinyl-substituted-1,2,3,4-tetrahydronaphthalene derivatives as (R)-enantiomers, (S)-enantiomers or racemates in the form of free base or pharmaceutically acceptable salts thereof, a process for their preparation, pharmaceutical compositions containing said therapeutically active compounds and to the use of said active compounds in therapy.

An object of the invention is to provide compounds for therapeutic use, especially compounds having a selective effect at a subgroup of 5-hydroxy-tryptamine receptors, designated the $h5-HT_{1B}$-receptor (previously called the $5-HT_{1D\beta}$-receptor) in mammals including man.

It is also an object of the invention to provide compounds with a therapeutic effect after oral administration.

PRIOR ART

Different classes of piperazinyl substituted benzanilide derivatives as $^5-HT_{1D}$ antagonists are disclosed in inter alia EP 533266, EP 533267, EP 533268, GB 2273930 and WO 95/11243.

WO 94/13659 discloses an extremely broad class of fused benzo compounds having a para substituted piperidyl or piperazinyl radical in the aromatic ring, said class of compounds are stated to bind to the $5-HT_{1A}$ receptor.

WO 94/21619 discloses fully aromatic naphthalene ring system which may be substituted with a piperidyl or piperazinyl group, said compounds are also stated to be potent serotonin ($5HT_1$) agonists and antagonists.

EP 402923 discloses 2-aminoalkyl or alkylenaromatic substituted 1,2,3,4-tetrahydronaphthalene derivatives having a further nitrogen substitution in the 5 position in the tetraline ring, said compounds act as dopamine agonists.

BACKGROUND OF THE INVENTION

Various central nervous system disorders such as depression, anxiety, etc. appear to involve the disturbance of the neurotransmitters noradrenaline (NA) and 5-hydroxytryptamine(5-HT), the latter also known as serotonin. The drugs most frequently used in the treatment of depression are believed to act by improving the neurotransmission of either or both of these physiological agonists. It appears that the enhancement of 5-HT neurotransmission primarily affects the depressed mood and anxiety, whereas the enhancement of noradrenaline neurotransmission affects the retardation symptoms occurring in depressed patients. The invention concerns compounds which have an effect on 5-HT neurotransmission.

Serotonin, or 5-HT, activity is thought to be involved in many different types of psychiatric disorders. For instance it is thought that an increase in 5-HT activity is associated with anxiety, while a decrease in 5-HT release has been associated with depression. Serotonin has in addition been implicated in such diverse conditions as eating disorders, gastrointestinal disorders, cardiovascular regulation and sexual behavior.

The 5-HT Receptors

The various effects of 5-HT may be related to the fact that serotonergic neurons stimulate the secretion of several hormones, e.g. cortisol, prolactin, β-endorphin, vasopressin and others. The secretion of each of these other hormones appears to be regulated on a specific basis by several different 5-HT (serotonin) receptor subtypes. With the aid of molecular biology techniques, to date these receptors have been classified as $5-HT_1$, $5-HT_2$, $5-HT_3$, $5-HT_4$, $5-HT_5$, $5-HT_6$ and $5-HT_7$ with the $5-HT_1$ receptor further divided into the $^5-HT_{1A}$, $5-HT_{1B}$, $5-HT_{1D}$, $5-HT_{1E}$ and $5-HT_{1F}$ subtypes. Each receptor subtype is involved in a different serotonin function and has different properties.

Regulation of the 5-HT transmission

The release of 5-HT at the nerve terminals is feedback-regulated by two different subtypes of 5-HT receptors. Inhibitory $5-HT_{1A}$ autoreceptors are located on the cell bodies in the raphe nuclei which upon stimulation by 5-HT decrease the impulse propagation in the 5-HT neurons and thereby reducing the 5-HT release at the nerve terminals. Another subtype of inhibitory 5-HT receptors is located on the 5-HT nerve terminals, the $h5-HT_{1B}$ receptors (in rodents the $r5-HT_{1B}$ receptors) which regulate the synaptic concentration of 5-HT by controlling the amount of 5-HT that is released. An antagonist of these terminal autoreceptors thus increases the amount of 5-HT released by nerve impulses which has been shown in both in vitro and in vivo experiments.

The use of an antagonist of the terminal $h5-HT_{1B}$ autoreceptor will accordingly increase the synaptic 5-HT concentration and enhance the transmission in the 5-HT system. It would thus produce an antidepressant effect making it useful as a medication for depression.

Other vocalizations of $h5-HT_{1B}$ receptor subtype also exist. A large part of these postsynaptic receptors appear to be located on nerve terminals of other neuronal systems (so called-heteroreceptors). Since the $h5-HT_{1B}$ receptor mediates inhibitory responses an antagonist of this receptor subtype might also increase the release of other neurotransmitters than 5-HT.

Compounds having $h5-HT_{1B}$ activity may according to well known and recognised pharmacological tests be divided into full agonists, partial agonists and antagonists.

DISCLOSURE OF THE INVENTION

The object of the present invention is to provide compounds having a selective effect at the $h5-HT_{1B}$ receptor, preferably antagonistic properties, as well as having a good bioavailability. The effect on the other receptors chosen from, for example, the $5-HT_{1A}$, $5-HT_{2A}$, $D_1$, $D_{2A}$, $D_3$, $\alpha_1$ and $\alpha_2$ receptor has been investigated. Accordingly, the present invention provides compounds of the formula I

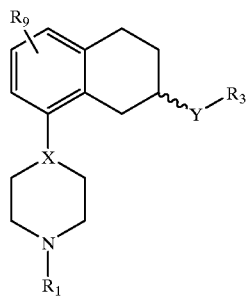

(I)

wherein
X is N or CH;
Y is $NR_2CH_2$, $CH_2$—$NR_2$, $NR_2$—CO, CO—$NR_2$ or $NR_2SO_2$
wherein $R_2$ is H or $C_1$–$C_6$ alkyl;
$R_1$ is H, $C_1$–$C_6$ alkyl or $C_3$–$C_6$ cycloalkyl;
$R_3$ is $C_1$–$C_6$ alkyl, $C_3$–$C_6$ cycloalkyl or $(CH_2)_n$-aryl,
wherein aryl is phenyl or a heteroaromatic ring containing one or two heteroatoms selected from N, 0 and S and which may be mono- or di-substituted with $R_4$ and/or $R_5$;
wherein $R_4$ is H, $C_1$–$C_6$ alkyl, $C_3$–$C_6$ cycloalkyl, halogen, CN, $CF_3$, OH, $C_1$–$C_6$ alkoxy, $NR_6R_7$, $OCF_3$, $SO_3CH_3$, $SO_3CF_3$, $SO_2NR_6R_7$, phenyl, phenyl-$C_1$–$C_6$ alkyl, phenoxy, $C_1$–$C_6$ alkyl phenyl, an optionally substituted heterocyclic ring containing one or two heteroatoms selected from N, O, S, SO and $SO_2$ wherein the substituent(s) is(are) selected from $C_1$–$C_6$ alkyl, $C_3$–$C_6$ cycloalkyl and phenyl—$C_1$–$C_6$ alkyl, an optionally substituted heteroaromatic ring containing one or two heteroatoms selected from N, O and S wherein the substituent(s) is(are) selected from $C_1$–$C_6$ alkyl, $C_3$–$C_6$ cycloalkyl and phenyl-$C_1$–$C_6$ alkyl, or $COR_8$;
wherein $R_6$ is H, $C_1$–$C_6$ alkyl or $C_3$–$C_6$ cycloalkyl; $R_7$ is H, $C_1$–$C_6$ alkyl or $C_3$–$C_6$ cycloalkyl; and
$R_8$ is $C_1$–$C_6$ alkyl, $C_3$–$C_6$ cycloalkyl, $CF_3$, $NR_6R_7$, phenyl, a heteroaromatic ring containing one or two heteroatoms selected from N, O and S or a heterocyclic ring containing one or two heteroatoms selected from N, O, S, SO and $SO_2$;
wherein $R_5$ is H, OH, $CF_3$, $OCF_3$, halogen, $C_1$–$C_6$ alkyl or $C_1$–$C_6$ alkoxy;
n is 0–4;
$R_9$ is $C_1$–$C_6$ alkyl, $C_3$–$C_6$ cycloalkyl, $OCF_3$, $OCHF_2$, $OCH_2F$, halogen, CN, $CF_3$, OH, $C_1$–$C_6$ alkoxy, $C_1$–$C_6$ alkoxy-$C_1$–$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from N, O and S wherein the substituent(s) is(are) $C_1$–$C_6$ alkyl; or $COR_8$; wherein $R_6$, $R_7$ and $R_8$ are as defined above,
as (R)-enantiomers, (S)-enantiomers or a racemate in the form of a free base or a pharmaceutically acceptable salt or solvate thereof which possess a high selective effect at the h5-$HT_{1B}$ receptor and also shows sufficient bioavailability after oral administration.

In the present context $C_1$–$C_6$ alkyl may be straight or branched. $C_1$–$C_6$ alkyl may be methyl, ethyl, n-propyl, i-propyl, n-butyl, i-butyl, s-butyl, t-butyl, n-pentyl, i-pentyl, t-pentyl, neo-pentyl, n-hexyl or i-hexyl In the present context $C_1$–$C_6$ alkoxy may be straight or branched. $C_1$–$C_6$ alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy, n-hexyloxy or i-hexyloxy.

In the present context $C_3$–$C_6$ cycloalkyl may be cyclopropyl, cyclobutyl, cyclopentyl or cyclohexyl.

In the present context halogen may be fluoro, chloro, bromo or iodo.

In the present context the heteroaromatic ring containing one or two heteroatoms selected from N, O and S preferably is a 5- or 6-membered heteroaromatic ring and may be furyl, imidazolyl, isoxazolyl, isothiazolyl, oxazolyl, pyrazinyl, pyrazolyl, pyridazinyl, pyridyl, pyrimidyl, pyrrolyl, thiazolyl or thienyl. The heteroaromatic ring can be either substituted or unsubstituted.

In the present context the heterocyclic ring containing one or two heteroatoms selected from N, O, S, SO and $SO_2$ may optionally contain a carbonyl function and is preferably a 5-, 6- or 7-membered heterocyclic ring and may be imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, preferably piperidino, 1-piperazinyl, morpholino, thiomorpholino and 4-piperidon-1-yl.

A preferred embodiment of the invention relates to compounds of formula I wherein Y is NHCO or CONH i.e. amides. Of those compounds, the compounds wherein $R_9$ is $C_1$–$C_6$ alkyl, $C_1$–$C_6$ alkoxy, $OCHF_2$ or $OCH_2F$ and $R_3$ is unsubstituted phenyl, or mono- or di-substituted phenyl, and especially ortho-, meta- or para- substituted phenyl, and particularly those wherein the substituent $R_4$ is phenyl, phenyl-$C_1$–$C_6$ alkyl, cyclohexyl, piperidino, 1-piperazinyl, morpholino, $CF_3$, 4-piperidon-1-yl, n-butoxy or $COR_8$ wherein $R_8$ is phenyl, cyclohexyl, 4-piperidon-1-yl, 1-piperazinyl, morpholino, $CF_3$, piperidino or $NR_6R_7$, are preferred.

Examples of Combinations of Substituents are:
X is N, Y is $CONR_2$, $R_1$ is H, $CH_3$, $C_2H_5$ or $C_3H_7$, $R_2$ is H, $R_3$ is $CH_2$-phenyl, $R_9$ is $CH_3$, $C_2H_5$ or $C_3H_7$;
X is CH, Y is $CONR_2$, $R_1$ is H, $CH_3$, $C_2H_5$ or $C_3H_7$, $R_2$ is H, $R_3$ is phenyl, $R_4$ is phenyl, phenylmethyl or phenylethyl, $R_5$ is H, $R_9$ is $OCH_3$;
X is CH, Y is $CONR_2$, $R_1$ is H, $CH_3$, $C_2H_5$ or $C_3H_7$, $R_2$ is H, $R_3$ is $CH_2$-phenyl, $R_4$ is piperidino, $R_5$ is H, $R_9$ is $CH_3$, $C_2H_5$ or $C_3H_7$;
X is N, Y is $NR_2CO$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $OCH_3$;
X is CH, Y is $NR_2CO$, $R_1$ is H, $CH_3$, $C_2H_5$ or $C_3H_7$, $R_2$ is H, $R_3$ is $(CH_2)$-phenyl, $R_9$ is $OCH_3$;
X is N, Y is $NR_2CO$, $R_1$ is H, $CH_3$, $C_2H_5$ or $C_3H_7$, $R_2$is H, $R_3$is$(CH_2)_2$-phenyl, $R_4$ is morpholino, $R_5$ is H, $R_9$ is $OCH_3$, $C_2H_5$ or $C_3H_7$;
X is CH, Y is $CONR_2$, $R_1$ is H, $CH_3$, $C_2H_5$ or $C_3H_7$, $R_2$ is H, $R_3$ is phenyl, $R_4$ is morpholino, $R_5$ is H, $R_9$ is $OCH_3$;
X is CH, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $CH_3$, $C_2H_5$ or $C_3H_7$;
X is CH, Y is $NR_2CO$, $R_1$ is H, $CH_3$, $C_2H_5$ or $C_3H_7$, $R_2$is H, $R_3$is $CH_2$-phenyl, $R_4$ is phenyl, phenylmethyl or phenylethyl, $R_5$ is H, $R_9$ is $OCH_3$;
X is N, Y is $CONR_2$, $R_1$ is H, $CH_3$, $C_2H_5$ or $C_3H_7$, $R_2$ is H, $R_3$ is phenyl, $R_9$ is $CH_3$, $C_2H_5$ or $C_3H_7$;
X is N, Y is $CONR_2$, $R_1$ is H, $CH_3$, $C_2H_5$ or $C_3H_7$, $R_2$ is H, $R_3$ is $(CH_2)_2$-phenyl, $R_4$ is piperidino, $R_5$ is H, $R_9$ is $OCH_3$;
X is CH, Y is $CONR_2$, $R_1$ is H, $CH_3$, $C_2H_5$ or $C_3H_7$, $R_2$ is H, $R_3$ is phenyl, $R_4$ is piperidino, $R_5$is H, $R_9$ is $OCH_3$;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is cyclohexyl, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is CH$_2$-phenyl, R$_9$ is CH$_3$, C$_2$H$_5$ or C$_3$H$_7$.

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is piperidino, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is morpholino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is phenyl, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_4$ is morpholino, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is CH$_2$-phenyl, R$_9$ is OCH$_3$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is OCH$_3$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_9$ is OCH$_3$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is phenyl, R$_4$ is piperidino, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is cyclohexyl, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_9$ is OCH$_3$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is COR$_8$, R$_8$ is NR$_6$R$_7$, R$_6$R$_7$CH$_3$, C$_2$H$_5$ or C$_3$H$_7$, R$_9$ is OCH$_3$;

X is N, Y is NR$_2$CO, R$_1$ is H, CH$_3$, C$_2$H$_5$ or C$_3$H$_7$, R$_2$ is H, R$_3$ is CH$_2$-phenyl, R$_9$ is OCH$_3$.

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_9$ is OCH$_3$;

X is N, Y is NR$_2$CO, R$_1$ is H, CH$_3$, C$_2$H$_5$ or C$_3$H$_7$, R$_2$ is H, R$_3$ is phenyl, R$_4$ is piperidino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_4$ is piperidino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)-phenyl, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_9$ is OCH$_3$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is COR$_8$, R$_8$ is NR$_6$R$_7$, R$_6$R$_7$CH$_3$, C$_2$H$_5$ or C$_3$H$_7$, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is OCH$_3$;

X is CH, Y is CONR$_2$, R$_1$ is H, CH$_3$, C$_2$Hs or C$_3$H$_7$, R$_2$ is H, R$_3$ is phenyl, R$_4$ is morpholino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is phenyl, R$_4$ is morpholino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_4$ is morpholino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is (CH$_2$)-phenyl, R$_9$ is OCH$_3$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is phenyl, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is (CH$_2$)-phenyl, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is phenyl, R$_4$ is piperidino, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is piperidino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is CH$_3$, C$_2$H$_5$ or C$_3$H$_7$;

X is N, Y is CONR$_2$, R$_1$ is H, CH$_3$, C$_2$Hs or C$_3$H$_7$, R$_2$ is H, R$_3$ is phenyl, R$_4$ is phenyl, phenylmethyl or phenylethyl, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is phenyl, R$_4$ is piperidino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is OCH$_3$;

X is N, Y is CONR$_2$, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is phenyl, R$_4$ is morpholino, R$_5$is H, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_4$ is morpholino, R$_5$ is H, R$_9$ is OCH$_3$;

X is CH, Y is CONR$_2$, R$_1$ is H, CH$_3$, C$_2$H$_5$ or C$_3$H$_7$, R$_2$ is H, R$_3$ is phenyl, R$_4$ is phenyl, phenylmethyl or phenylethyl, R$_5$ is H, R$_9$ is CH$_3$, C$_2$H$_5$ or C$_3$H$_7$;

X is N, Y is NR$_2$CO, R$_1$ is H, CH$_3$, C$_2$H$_5$ or C$_3$H$_7$, R$_2$ is H, R$_3$ is phenyl, R$_4$ is COR$_8$, R$_8$ is morpholino, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is phenyl, R$_9$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is phenyl, phenylmethyl or phenylethyl, R$_5$ is H, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$-phenyl, R$_4$ is morpholino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)2-phenyl, R$_4$ is piperidino, R$_5$ is H, R$_9$ is OCH$_3$;

X is N, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is morpholino, R$_5$ is H, R$_9$ is OCH$_3$;

X is CH, Y is NR$_2$CO, R$_1$ is H, CH$_3$, C$_2$H$_5$ or C$_3$H$_7$, R$_2$ is H, R$_3$ is (CH$_2$)$_2$-phenyl, R$_4$ is phenyl, phenylmethyl or phenylethyl, R$_5$ is H, R$_5$ is CH$_3$, C$_2$H$_5$ or C$_3$H$_7$;

X is N, Y is CONR$_2$, R$_1$ is H, CH$_3$, C$_2$H$_5$ or C$_3$H$_7$, R$_2$ is H, R$_3$ is CH$_2$-phenyl, R$_4$ is piperidino, R$_5$ is H, R$_9$ is CH$_3$, C$_2$H$_5$ or C$_3$H$_7$;

X is CH, Y is CONR$_2$, R$_1$ is H, CH$_3$, C$_2$H$_5$ or C$_3$H$_7$, R$_2$ is H, R$_3$ is (CH$_2$)$_2$-phenyl, R$_9$ is CH$_3$, C$_2$H$_5$ or C$_3$H$_7$;

X is CH, Y is NR$_2$CO, R$_1$ is H, CH$_3$, C$_2$H$_5$ or C$_3$H$_7$, R$_2$ is H, R$_3$ is CH$_2$ phenyl, R$_4$ is phenyl, phenylmethyl or phenylethyl, R$_5$ is H, R$_9$ is CH$_3$, C$_2$H$_5$ or C$_3$H$_7$.

Preferred Compounds are:

(R)-N-[5-Methoxymethyl-8-(4-methylpiperazin-1-yl)-1,2,3,4-tetrahydro-2-naphthyl]-4-morpholinobenzamide;

(R)-N-[5-Bromo-8-(4-methylpiperazin-1-yl)-1,2,3,4-tetrahydro-2-naphthyl]-4-trifluoromethylbenzamide;

(R)-N-[5-Bromo-8-(4-methylpiperazin-1-yl)-1,2,3,4-tetrahydro-2-naphthyl]-4-morpholinobenzamide;

(R)-N-[5-Bromo-8-(piperazin-1-yl)-1,2,3,4-tetrahydro-2-naphthyl]-4-morpholinobenzamide;

(R)-N-[5-Hydroxy-8-(4-methylpiperazin-1-yl)-1,2,3,4-tetrahydro-2-naphthyl]-4-butoxybenzamide;

(R)-N-[5-Methoxy-8-(4-methylpiperazin-1-yl)-1,2,3,4-tetrahydro-2-naphthyl]-4-morpholinobenzamide;

(R)-N-[5-Methoxy-8-(4-methylpiperazin-1-yl)-1,2,3,4-tetrahydro-2-naphthyl]-4-morpholinocarbonylbenzamide;

(R)-N-[5-Methyl-8-(piperazin-1-yl)-1,2,3,4-tetrahydro-2-naphthyl]-4-morpholinobenzamide;

(R)-N-[5-Bromo-8-(4-methylpiperazin-1-yl)-1,2,3,4-tetrahydro-2-naphthyl]-4-morpholinocarbonylbenzamide;

N-(4-Morpholinophenyl)--(4-methylpiperazinyl)-5-methoxy-1,2,3,4-tetrahydronaphthalene-2-carboxamide;

N-(Morpholinocarbonylphenyl)-8-(4-methylpiperazin-1-yl)-5-methoxy-1,2,3,4-tetrahydronaphthalene-2-carboxamide;

(R)-N-[5-Ethyl-8-(4-methylpiperazin-1-yl)-1,2,3,4-tetrahydro-2-naphtyl]-4-morpholinobenzamide;

(R)-N-[5-Ethyl-8-(4-methylpiperazin-1-yl)-1,2,3,4-tetrahydro-2-naphthyl]-(4-morpholinocarbonyl)benzamide;

(R)-N-[5-Difluoromethoxy-8-(4-methylpiperazin-1-yl)-1,2,3,4-tetrahydro-2-naphthyl]-4-morpholinobenzamide; and (R)-N-[5-Methyl-8-(4-methylpiperazin-1-yl)-1,2,3,4-tetrahydro-2-naphthyl]-4-morpholinobenzamide.

The compounds of the present invention are in the form of the racemate or the (R)- or (S)-enantiomer in the form of a free base or a pharmaceutically acceptable salt or solvate thereof. Compounds in the forn of the (R)-enantiomer are preferred ones. Both organic and inorganic acids can be employed to form non-toxic pharmaceutically acceptable acid addition salts of the compounds of this invention. Illustrative acids are sulfuric, nitric, phosphoric, oxalic, hydrochloric, fornic, hydrobromic, citric, acetic, lactic, tartaric, dibenzoyltartaric, diacetyltartaric, palmoic, ethanedisulfonic, sulfamic, succinic, propionic, glycolic, malic, gluconic, pyruvic, phenylacetic, 4-aminobenzoic, anthranilic, salicylic, 4-aminosalicylic, 4-hydroxybenzoic, 3,4-dihydroxybenzoic, 3,5-dihydroxybenzoic, 3-hydroxy-2-naphthoic, nicotinic, methanesulfonic, ethanesulfonic, hydroxyethanesulfonic, benzenesulfonic, p-toluenesulfonic, sulfanilic, naphthalenesulfonic, ascorbic, cyclohexylsulfamic, fumaric, maleic and benzoic acids. These salts are readily prepared by methods known in the art.

The preferred solvates of the compounds of this invention are the hydrates.

Pharmaceutical Formulations

In a second aspect the present invention provides a pharmaceutical formulation comprising as active ingredient a therapeutically effective amount of the compound of formula I as an enantiomer or a racemate in the form of a free base or a pharmaceutically acceptable salt or solvate thereof, optionally in association with diluents, excipients or inert carriers.

According to the present invention the compound of the invention will normally be administered orally, rectally or by injection, in the form of pharmaceutical formulations comprising the active ingredient either as a free base or a pharmaceutically acceptable non-toxic acid addition salt, e.g. the hydrochloride, hydrobromide, lactate, acetate, phosphate, sulfate, sulfamate, citrate, tartrate, oxalate and the like in a pharmaceutically acceptable dosage form. The dosage form may be a solid, semisolid or liquid preparation. Usually the active substance will constitute between 0.1 and 99% by weight of the preparation, more specifically between 0.5 and 20% by weight for preparations intended for injection and between 0.2 and 50% by weight for preparations suitable for oral administration.

To produce pharmaceutical formulations containing the compound of the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the person skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or poly-ethylene glycol. Hardgelatine capsules may contain granules of the active substance using either the above mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into is hard gelatine capsules.

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.1% to about 20% by weight of the active substance herein described, the balance being sugar and mixture of ethanol, water, glycerol and propylene glycol. Optionally such liquid preparations may con tain colouring agents, flavouring agents, saccharine and carboxymethylcellulose as a thickening agent or other excipients known to the person skilled in the art.

Solutions for parenteral applications by injection can be prepared in an aqueous solution of a water-soluble pharmaceutically acceptable salt of the active substance, preferably in a concentration of from about 0.1% to about 10% by weight. These solutions may also contain stabilizing agents and/or buffering agents and may conveniently be provided in various dosage unit ampoules.

Suitable daily doses of the compound of the invention in therapeutical treatment of humans are about 0.01–100 mg/kg bodyweight at peroral administration and 0.001–100 mg/kg bodyweight at parenteral administration.

The compound of the invention may be used in a combination with a 5-HT reuptake inhibitor, such as fluoxetine, paroxetine, citalopram, clomipramine, sertraline, alaproclate or fluvoxamin, preferably paroxetine or citalopram. Another possible combination is to use the compound of the invention together with a monoamine oxidase inhibitor, such as moclobemide, tranylcypramine, brofaromide or phenelzine, preferably moclobemide or phenelzine . Still another possible combination is the compound of the invention together with a 5-$HT_{1A}$ antagonist, such as the compounds disclosed in WO 96/33710, preferably (R)-5-carbamoyl-3-(N,N-dicyclobutylamino)-8-fluoro-3,4-dihydro-2H-1-benzopyran.

Medical and Pharmaceutical Use

In a further aspect the present invention provides the use of the compounds of formula I in therapy as a h5-$HT_{1B}$ antagonists, partial agonists or full agonists, preferably as antagonists and the use in the treatment of 5-hydroxytryptamine mediated disorders. Examples of such disorders are disorders in the CNS such as mood disorders (depression, major depressive episodes, dysthymia, seasonal affective disorder, depressive phases of bipolar disorder), anxiety disorders (obsessive compulsive disorder, panic disorder with/without agoraphobia, social phobia, specific phobia, generalized anxiety disorder, posttraumatic stress disorder), personality disorders (disorders of impulse control, trichotellomania), obesity, anorexia, bulimia, premenstrual syndrome, sexual disturbances, alcoholism, tobacco abuse, autism, attention deficit, hyperactivity disorder, migraine, memory disorders (age associated memory impairment, presenile and senile dementia), pathological aggression, schizophrenia, endocrine disorders (e g hyperprolactinaemia), stroke, dyskinesia, Parkinson's disease, thermoregulation, pain, hypertension. Other examples of hydroxytryptamine mediated disorders are urinary incontinence, vasospasm and growth control of tumors (e g lung carcinoma).

Methods of Preparation

The present invention also relates to processes for preparing the compound of formula I. Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Greene, Wiley-Interscience, New York, 1991.

Methods of Preparation of Intermediates

1. In the case where Y is NR₂CO and X is N (i) Benzylation of the compound of the formula II, either as a racemate or as an enantiomer,

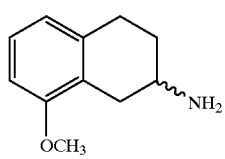

(II)

to obtain a compound of formula III may be carried out by reaction with a suitable benzylation agent e.g. a benzyl halide such as benzyl bromide or benzyl chloride or an activated alcohol e.g. benzylmesylate or benzyltosylate. The reaction may be carried out using a salt or the base of compound II in a suitable solvent e.g. N,N-dimethylformamide, acetone or acetonitrile with a suitable base e.g. NaOH, NaHCO₃, K₂CO₃ or a trialkylamine such as triethylamine at a temperature within the range of +20° C. to +150° C. The presence of a suitable catalyst e.g. potassium iodide or sodium iodide, may increase the speed of the reaction. The nitrogen in compound II may also be protected by reductive alkylation with an arylaldehyde in the presence of a reductive agent such as sodium cyanoborohydride, sodium borohydride or catalytically with H₂ and a suitable catalyst containing palladium, platinum, rhodium or nickel in a suitable solvent e.g. tetrahydrofuran, dioxane, methanol or ethanol. A proton donor such as p-toluenesulfonic acid can be used to catalyze the formation of the imine/enamine, and adjustment of pH to slightly acidic by an appropriate acid such as acetic acid may speed up the reaction, resulting in compound III.

(ii) Demethylation of the compound of formula III

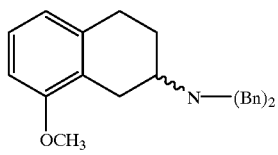

(III)

to obtain a compound of formula IV may be carried out by treating the compound with an acidic reagent such as aqueous HBr, HI, HBr/CH₃COOH, BBr₃, AlCl₃, pyridine-HCl or with a basic nucleophilic reagent such as CH₃C₆H₄S⁻ or C₂H₅S⁻ in a suitable solvent. Suitable solvents may be methylene chloride or chloroform and the reaction may occur between −78° C. and +60° C.

(iii) Conversion of the compound of formula IV to a compound of formula V

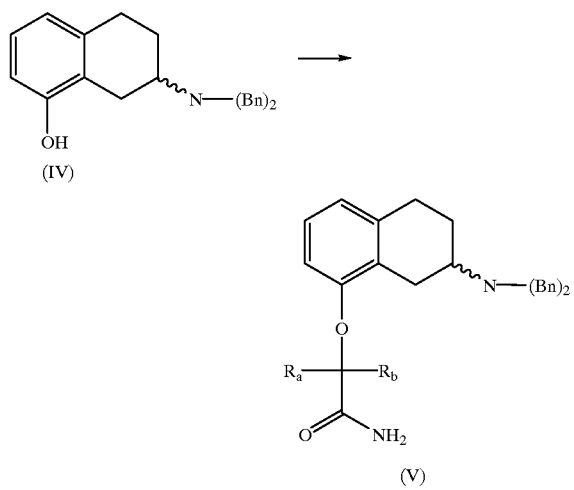

may be carried out by the reaction with a compound of formula VI

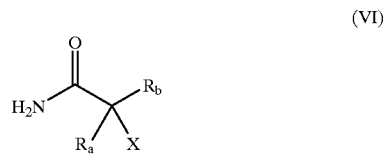

(VI)

where X stands for a leaving group, e.g. a halogen such as chlorine, bromine or iodine or an alkane- or arenesulfonyloxy group such as a p-toluenesulfonyloxy group and $R_a$ and $R_b$ are hydrogen or a lower alkyl group e.g. methyl. The process may be carried out with a salt of the compound of formula IV obtained by reaction with a base such as K₂CO₃, Na₂CO₃, KOH, NaOH, BuLi or NaH. The reaction may be conducted in a suitable solvent e.g. an aprotic solvent such as dioxane, N,N-dimethylformamide, tetrahydrofuran, toluene, benzene or petroleum ether and the reaction may occur between +20° C. and +150° C.

(iv) Rearrangement of a compound of formula V to a compound of formula VII

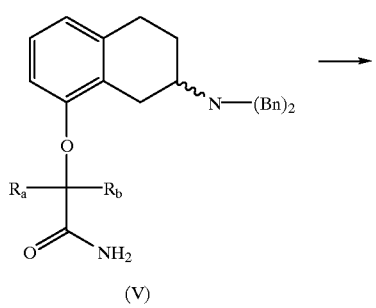

(V)

-continued

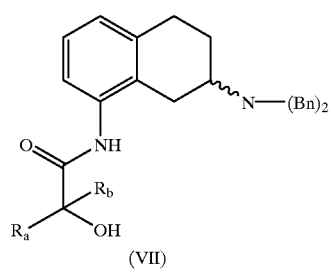

(VII)

may be carried out in a suitable solvent e.g. aprotic solvent such as N,N dimethylformamide, dioxane, 1,1,3,3-tetramethylurea, tetrahydrofuran or hexamethylphosphoric triamide with a suitable base e.g. $K_2CO_3$, KOH, potassium tert-butoxide or NaH at a temperature within the range of +20° C. to +150° C.

The presence of a cosolvent such as 1,3-dimethyl-3,4,5,6-tetrahydro-2(1H)-pyrimidone or hexamethylphosphoric triamide in appropriate concentration in the solvent may increase the speed of the reaction.

(v) Hydrolysis of a compound of formula VII to a compound VIII may be carried out under acidic conditions using acids such as $H_2SO_4$, HCl or HBr in a suitable solvent e.g. $H_2O$, ethanol, methanol or mixtures thereof and the reaction may occur between +20° C. and +100° C. or under basic conditions using bases such as NaOH or KOH in a suitable solvent e.g. $H_2O$, ethanol, methanol or mixtures thereof and the reaction may occur between +20° C. and +100° C.

(vi) Conversion of compound of formula VIII to a compound of formula IX

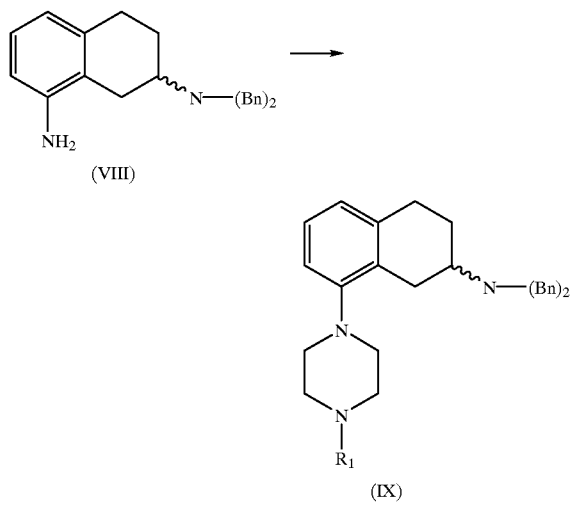

may be carried out by
a) reaction with a compound of formula X

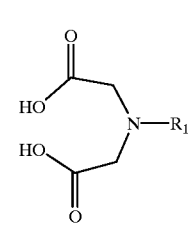

where $R_1$ is $C_1$–$C_6$ alkyl or $C_3$–$C_6$ cycloalkyl. The process may be carried out in a suitable solvent e.g. an aprotic/anhydrous solvent such as tetrahydrofuran or N,N-dimethylformamide in the presence of coupling reagent such as N,N'-carbonyldiimidazole and the reaction may occur between +20° C. and +130° C. The reaction is followed by the reduction of the imide with a suitable reducing agent e.g. $LiAlH_4$ in a suitable solvent e.g. diethyl ether or tetrahydrofuran at a temperature between +20° C. and reflux, or b) by reaction with a compound of formula XI

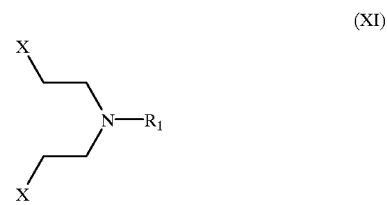

where X stands for a leaving group, e.g. a halogen such as chlorine or bromine or an alkane- or arenesulfonyloxy group such as p-toluenesulfonyloxy group and $R_1$ is H, $C_1$–$C_6$-alkyl or $C_3$–$C_6$ cycloalkyl. The process may be carried out in a suitable solvent such as ethanol, buthanol, N,N-dimethylformamide, acetonitrile or a mixture of water and acetonitrile with a suitable base e.g. $K_2CO_3$, $NaHCO_3$ or KOH and the reaction may occur between +20° C. and +150° C.

(vii) Compound of formula IX may also be prepared by benzylation of the compound of the formula LVIII, where $R_e$ is a halogen such as chlorine, bromine or iodine, either as a racemate or as an enantiomer,

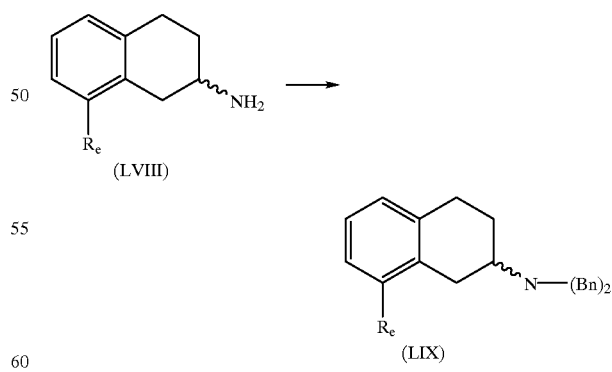

to obtain a compound of formula LIX by the reaction with a suitable benzylation agent e.g. a benzyl halide such as benzyl bromide or benzyl chloride or an activated alcohol e.g. benzylmesylate or benzyltosylate. The reaction may be carried out using a salt or the base of compound LVIII in a suitable solvent e.g. N,N-dimethylformamide, acetone or acetonitrile with a suitable base e.g. NaOH, NaHCO$_3$, K$_2$CO$_3$ or a trialkylamine such as triethylamine at a temperature within the range of +20° C. to +150° C. The presence of a suitable catalyst e.g. potassium iodide or sodium iodide may increase the speed of the reaction.

(viii) Conversion of the compound of formula LIX to a compound of formula IX, where R$_1$ is Hydrogen, C$_1$–C$_6$ alkyl or C$_3$–C$_6$ cycloalkyl, may be carried out by reaction with a compound of formula XXII.

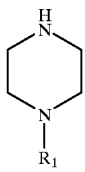

(XXII)

The process may be carried out in a suitable solvent e.g. an aprotic solvent such as benzene, toluene, dioxane, tetrahydrofuran or N,N-dimethylformamide with a suitable base such as sodium tert-butoxide or lithium bis(trimethylsilyl)amide in the presence of a suitable palladium catalyst such as PdX$_2$, L$_2$Pd(0) or L$_2$PdX$_2$ where X stands for a halogen such as chlorine or bromine and L stands for a suitable ligand such as triphenylphosphine, tri-o-tolylphosphine, trifurylphosphine, triphenylarsine or dibenzylidenacetone and with or without an addition of a ligand L' such as triphenylphosphine, tri-o-tolylphosphine, trifurylphosphine, 2,2'-bis(diphenylphosphino)-1,1'-binaphthalene (either as a racemate or as an enantiomer) or triphenylarsine and the reaction may occur at a temperature between +20° C. and +150° C., resulting in the compound of the formula IX.

The conversion of LIX to IX can also proceed via the tranformation of XXII to an aminostannane or aminoborane using agents such as (N,N-diethylamino)tributyltin or tris(dimethylamino)borane in a suitable solvent e.g an aprotic solvent such as benzene, toluene, dioxan, tetrahydrofuran or N,N-dimethylformamide and then using similar conditions as described in the above description, resulting in the compound of the formula IX.

(ix) Halogenation of the compound of formula IX, where R$_1$ is hydrogen, C$_1$–C$_6$-alkyl or C$_3$–C$_6$-cycloalkyl,

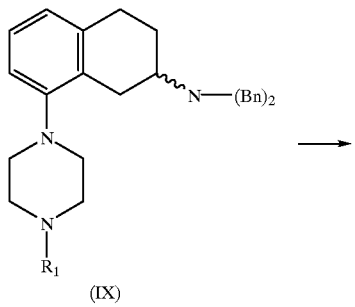

(IX)

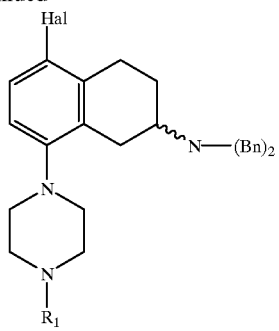

(XII)

to obtain a compound of formula XII may be performed by aromatic electrophilic substitution using a suitable halogenation agent such as Br$_2$, Cl$_2$, I$_2$, ICl, or SO$_2$Cl$_2$. The reaction may be carried out using the salt or the base of the compound IX in an appropriate solvent e.g. acetic acid, HCl/ethanol or water with or without a suitable base e.g. alkali metal acetate such as sodium acetate and at a reaction temperature between −20° C. and room temperature.

A compound of the formula XII may also be prepared by benzylation of a compound of the formula XVI to obtain a compound of formula XII by reaction with a suitable benzylation agent e.g. a benzyl halide such as benzyl bromide or benzyl chloride or an activated alcohol e.g. benzylmesylate or benzyltosylate in a suitable solvent e.g. N,N-dimethylformamide, acetone or acetonitrile with a suitable base e.g. NaOH, NaHCO$_3$, K$_2$CO$_3$ or a trialkylamine such as triethylamine at a temperature within the range of +20° C. to +150 ° C. The presence of a suitable catalyst e.g. potassium iodide or sodium iodide, may increase the speed of the reaction.

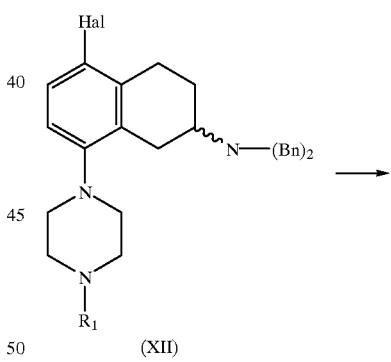

(XII)

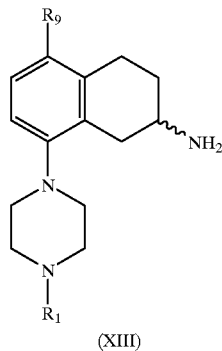

(XIII)

(x) Conversion of the compound of formula XII to a compound of formula XIII, where R$_1$ is hydrogen, C$_1$–C$_6$ alkyl or $C_3$–$C_6$ cycloalkyl and $R_9$ is $C_1$–$C_6$ alkyl, may be carried out by a metal-halogen exchange, in a appropriate anhydrous solvent such as tetrahydrofuran or diethyl ether using a suitable alkyl-lithium or metal e.g. buthyllithium, lithium or magnesium turnings, followed by treatment with appropriate alkyl halide such as methyl iodide, ethyl bromide or propyl iodide and the reaction may be performed at a reaction temperature within the range of −78° C. to room temperature, followed by cleavage of the benzyl groups by hydrogenation over a suitable catalyst containing palladium, rhodium, platina or nickel, in a suitable solvent e.g. acetic acid or ethanol and at a reaction temperature between +20° C. and +120° C., or treatment with other electrophiles such as acetaldehyde or methyl chloroformate and a thereafter following suitable work-up. The reaction may be performed at a reaction temperature within the range of −78° C. to room temperature.

In the case where acetaldehyde is used as electrophile, the above reaction is followed by reduction of the benzyl alcohol and cleavage of the benzyl groups by hydrogenation over a suitable catalyst containing palladium, rhodium, platina or nickel, in a suitable solvent e.g. acetic acid or ethanol and the reaction may occur between +20° C. and +120° C.

In the case where methyl chloroformate is used as electrophile, the above reaction is followed by reduction of the methyl ester in a suitable solvent such as diethyl ether or tetrahydrofuran with an appropriate reductive agent such as lithium aluminum hydride and the reaction may occur between +20° C. and reflux, followed by cleavage of the benzyl groups and reduction of the benzyl alcohol by hydrogenation over a suitable catalyst containing palladium, rhodium, platina or nickel, in a suitable solvent e.g. acetic acid or ethanol and the reaction may occur between +20° C. and +120° C.

When $R_1$ is hydrogen, the piperazine nitrogen is protected with a suitable protecting group before the lithiation step such as a benzyl group or another protecting group known by a person skilled in the art and then removed by methods known by a person skilled in the art, resulting in the compound of formula XIII.

(xi) Compound of formula XIII, where $R_1$ is hydrogen, may also be prepared by,

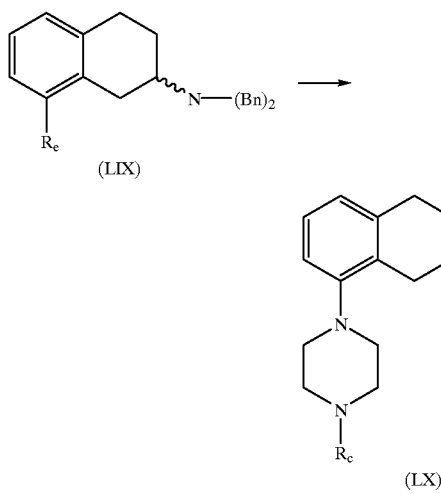

the conversion of the compound of formula LIX to a compound of formula LX, by the reaction with a compound of formula LXI, where $R_c$ is a suitable protecting group such as a benzyl group.

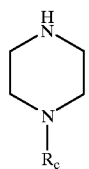

(LXI)

The process may be carried out in a suitable solvent e.g. an aprotic solvent such as benzene, toluene, dioxane, tetrahydrofuran or N,N-dimethylformamide with a suitable base such as sodium tert-butoxide or lithium bis(trimethylsilyl)amide in the presence of a suitable palladium catalyst such as $PdX_2$, $L_2Pd(0)$ or $L_2PdX_2$ where X stands for a halogen such as chlorine or bromine and L stands for a suitable ligand such as triphenylphosphine, tri-o-tolylphosphine, trifurylphosphine, triphenylarsine or dibenzylidenacetone and with or without an addition of a ligand L' such as triphenylphosphine, tri-o-tolylphosphine, trifurylphosphine, 2,2'-bis(diphenylphosphino)-1,1'-binaphthalene (either as a racemate or as an enantiomer) or triphenylarsine and the reaction may occur at a temperature between +20° C. and +150° C., resulting in the compound of the formula LX.

The conversion of LIX to LX can also proceed via the tranformation of LXI to an aminostannane or aminoborane using agents such as (N,N-diethylamino)tributyltin or tris(dimethylamino)borane in a suitable solvent e.g an aprotic solvent such as benzene, toluene, dioxan, tetrahydrofuran orN,N-dimethylformamide and then using similar conditions as described in the above description, resulting in the compound of the formula LX.

(xii) Halogenation of the compound of formula LX,

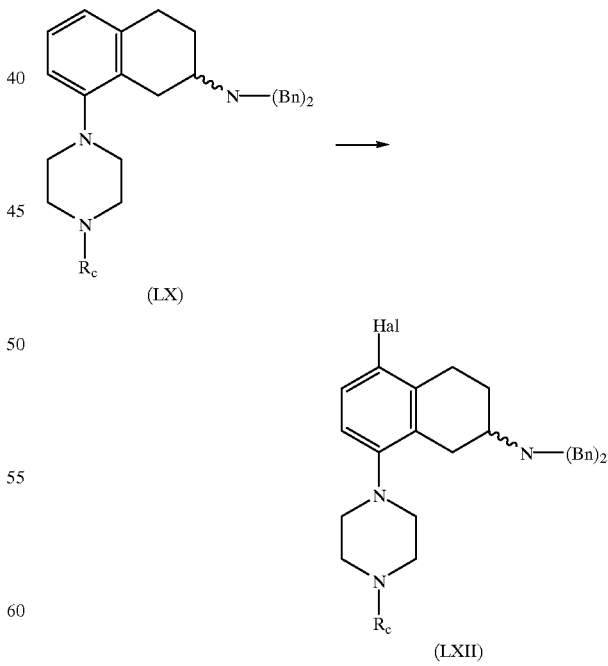

to obtain a compound of formula LXII may be performed by aromatic electrophilic substitution using a suitable halogenation agent such as $Br_2$, $Cl_2$, $I_2$, ICl, or $SO_2Cl_2$. The reaction may be carried out using the salt or the base of the compound LX in an appropriate solvent e.g. acetic acid, HCl/ethanol or water with or without a suitable base e.g. alkali metal acetate such as sodium acetate and at a reaction temperature between −20° C. and room temperature.

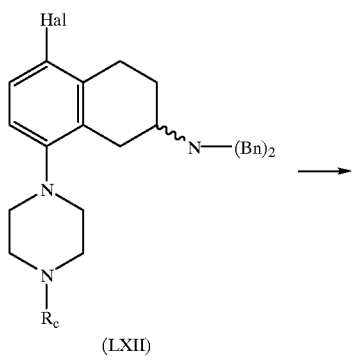

(LXII)

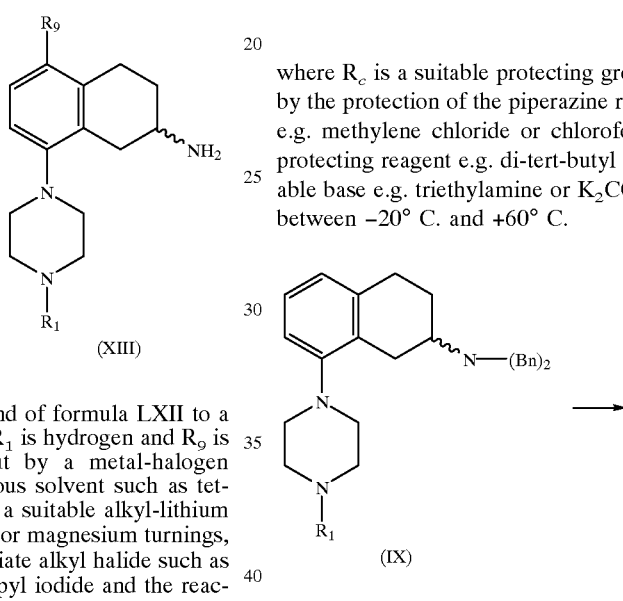

(XIII)

(xiii) Conversion of the compound of formula LXII to a compound of formula XIII, where $R_1$ is hydrogen and $R_9$ is $C_1$–$C_6$ alkyl, may be carried out by a metal-halogen exchange, in a appropriate anhydrous solvent such as tetrahydrofuran or diethyl ether using a suitable alkyl-lithium or metal e.g. buthyllithium, lithium or magnesium turnings, followed by treatment with appropriate alkyl halide such as methyl iodide, ethyl bromide orpropyl iodide and the reaction may be performed at a reaction temperature within the range of −78° C. to room temperature, followed by cleavage of the benzyl groups by hydrogenation over a suitable catalyst containing palladium, rhodium, platina or nickel, in a suitable solvent e.g. acetic acid or ethanol and at a reaction temperature between +20° C. and +120° C., or treatment with other electrophiles such as acetaldehyde or methyl chloroformate and a thereafter following suitable work-up. The reaction may be performed at a reaction temperature within the range of −78° C. to room temperature.

In the case where acetaldehyde is used as electrophile, the above reaction is followed by reduction of the benzyl alcohol and cleavage of the benzyl groups by hydrogenation over a suitable catalyst containing palladium, rhodium, platina or nickel, in a suitable solvent e.g. acetic acid or ethanol and the reaction may occur between +20° C. and +120° C.

In the case where methyl chloroformate is used as electrophile, the above reaction is followed by reduction of the methyl ester in a suitable solvent such as diethyl ether or tetrahydrofuran with an appropriate reductive agent such as lithium aluminum hydride and the reaction may occur between +20° C. and reflux, followed by cleavage of the benzyl groups and reduction of the benzyl alcohol by hydrogenation over a suitable catalyst containing palladium, rhodium, platina or nickel, in a suitable solvent e.g. acetic acid or ethanol and the reaction may occur between +20° C. and +120° C.

(xiv) Conversion of a compound of formula XIII, where $R_1$ is hydrogen, to a compound of formula XIV,

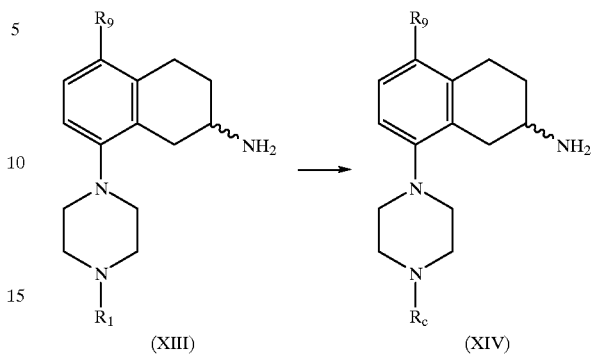

(XIII)                (XIV)

where $R_c$ is a suitable protecting group, may be carried out by the protection of the piperazine ring in a suitable solvent e.g. methylene chloride or chloroform with a appropriate protecting reagent e.g. di-tert-butyl dicarbonate with a suitable base e.g. triethylamine or $K_2CO_3$ and at a temperature between −20° C. and +60° C.

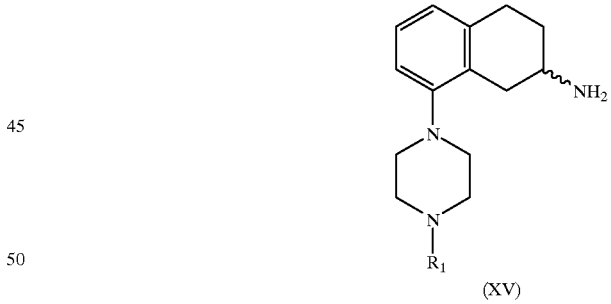

(XV)

(xv) Conversion of the compound of formula IX, where $R_1$ is hydrogen, $C_1$–$C_6$ alkyl or $C_3$–$C_6$ cycloalkyl to a compound of formula XV, where $R_1$ is hydrogen, $C_1$–$C_6$ alkyl or $C_3$–$C_6$ cycloalkyl may be carried out by cleavage of the benzyl groups by hydrogenation over a suitable catalyst containing palladium, rhodium, platina or nickel, in a suitable solvent e.g. acetic acid or ethanol and the reaction may occur between +20° C. and +120.

(xvi) Halogenation of the compound of formula XV, where $R_1$ is hydrogen, $C_1$–$C_6$-alkyl or $C_3$–$C_6$-cycloalkyl,

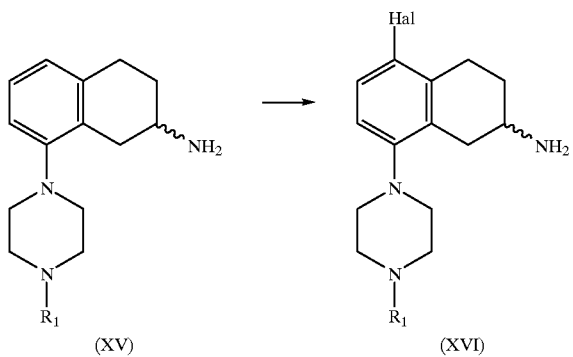

to obtain a compound of formula XVI may be performed by aromatic electrophilic substitution using a suitable halogenation agent such as $Br_2$, $Cl_2$, $I_2$, ICl, or $SO_2Cl_2$. The reaction may be carried out using the salt or the base of the compound XV in a appropriate solvent e.g. acetic acid, HCl/ethanol or water with or without a suitable base e.g. alkali metal acetate such as sodium acetate and at a reaction temperature between –20° C. and room temperature.

(xvii) Conversion of a compound of formula XVI, where $R_1$ is hydrogen, to a compound of formula XVII,

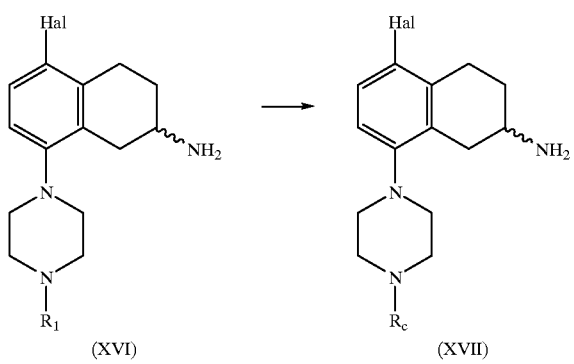

where $R_c$ is a suitable protecting group, may be carried out by the protection of the piperazine ring in a suitable solvent e.g. methylene chloride or chloroform with an appropriate protecting reagent e.g. di-tert-butyl dicarbonate with a suitable base e.g. triethylamine or $K_2CO_3$ and at a temperature between –20° C. and +60° C.

(xviii) Halogenation of the compound of formula XVIII, where $R_9$ is $C_1$–$C_6$ alkoxy, either as racemate or as an enantiomer

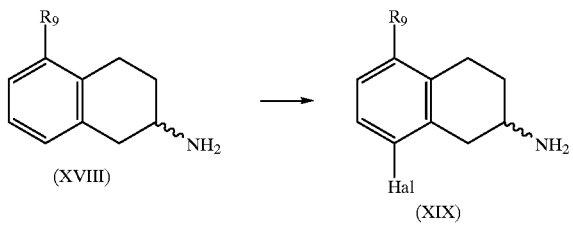

to obtain a compound of formula XIX may be performed by aromatic electrophilic substitution using a suitable halogenation agent such as $Br_2$, $Cl_2$, $I_2$, ICl, or $SO_2Cl_2$. The reaction may be carried out using the salt or the base of the compound XVIII in an appropriate solvent e.g. acetic acid, HCl/ethanol or water with or without a suitable base e.g. alkali metal acetate such as sodium acetate and at a reaction temperature between –20° C. and room temperature.

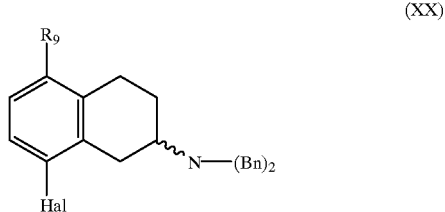

(xix) Benzylation of the compound of the formula XIX, either as a racemate or as an enantiomer, to obtain a compound of the formula XX by reaction with a suitable benzylation agent e.g. benzyl halide such as benzyl bromide or benzyl chlorideor an activated alcohol e.g. benzylmesylate or -tosylate. The reaction may be carried out using the salt or the base of compound XIX in a suitable solvent e.g. N,N-dimethylformamide, acetone or acetonitrile with a suitable base such as triethylamine, NaOH, $NaHCO_3$ or $K_2CO_3$ at a temperature within the range of +20° C. to +150° C. The presence of a suitable catalyst e.g. alkali metal halide such as potassium iodide or sodium iodide may increase the speed of the reaction.

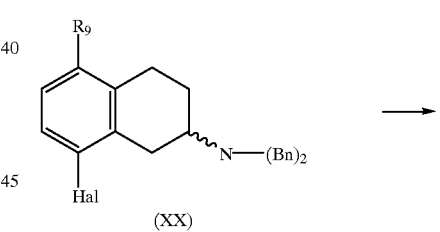

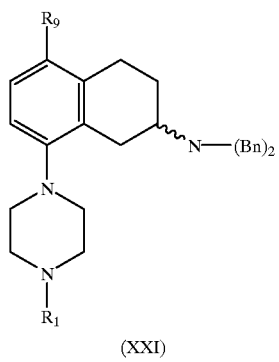

(xx) Conversion of the compound of formula XX to a compound of formula XXI, where $R_1$ is hydrogen, $C_1$–$C_6$ alkyl or $C_3$–$C_6$ cycloalkyl and $R_9$ is $C_1$–$C_6$ alkoxy, may be carried out by the reaction with a compound of formula XXII, where $R_1$ is hydrogen, $C_1$–$C_6$ alkyl or $C_3$–$C_6$ cycloalkyl.

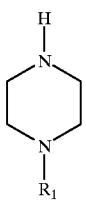

(XXII)

The process may be carried out in a suitable solvent e.g. an aprotic solvent such as benzene, toluene, dioxane, tetrahydrofuran or N,N-dimethylformamide with a suitable base such as sodium tert-butoxide or lithium bis(trimethylsilyl)amide in the presence of a suitable palladium catalyst such as $PdX_2$, $L_2Pd(O)$ or $L_2PdX_2$ where X stands for a halogen such as chlorine or bromine and L stands for a suitable ligand such as triphenylphosphine, tri-o-tolylphosphine, trifurylphosphine, triphenylarsine or dibenzylidenacetone and with or without an addition of a ligand L' such as triphenylphosphine, tri-o-tolylphosphine, trifurylphosphine, 2,2'-bis(diphenylphosphino)-1,1'-binaphthalen (either as a racemate or as an enantiomer) or triphenylarsine and the reaction may occur at a temperature between +20° C. and +150° C.

(xxi) Conversion of the compound of formula XXI to a compound of formula XXIII

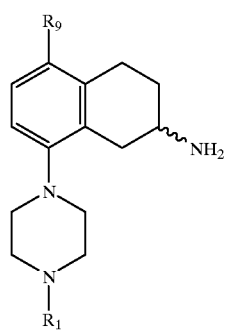

(XXIII)

where $R_1$ is hydrogen, $C_1$–$C_6$ alkyl or $C_3$–$C_6$ cycloalkyl and $R_9$ is $C_1$–$C_6$ alkoxy may be carried out by hydrogenation using a catalyst containing palladium, platinum, rhodium or nickel in a suitable solvent e.g. acetic acid or ethanol at a reaction temperature between +20° C. and +120° C.

(xxii) Conversion of compound of formula XXIII, where $R_1$ is hydrogen, to a compound of formula XXIV,

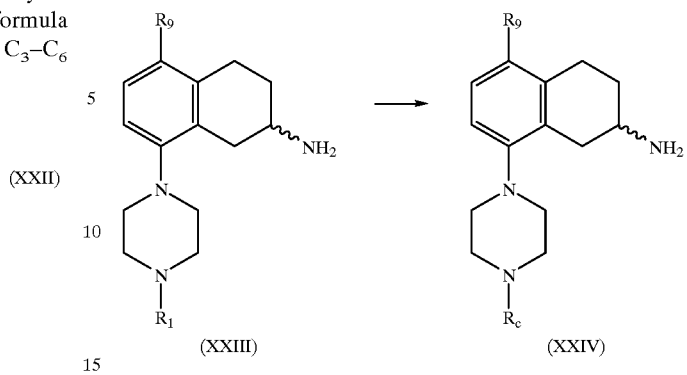

(XXIII)  (XXIV)

where $R_c$ is a suitable protecting group, may be carried out by the protection of the piperazine ring in a suitable solvent e.g. methylene chloride or chloroform with a is appropriate protecting reagent e.g. di-tert-butyl dicarbonate with a suitable base e.g. triethylamine or $K_2CO_3$ and at a temperature between −20° C. and +60° C.

(xxiii) Dealkylation of the compound of formula XXI,

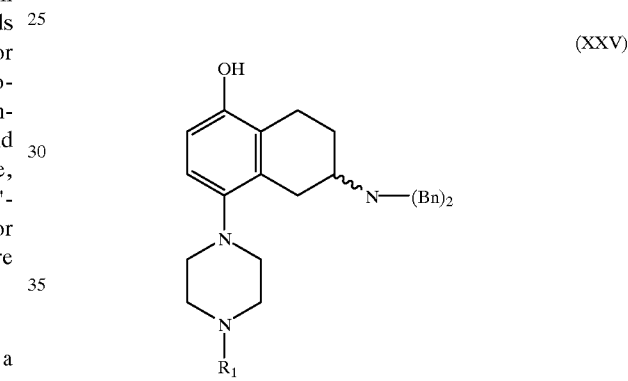

(XXV)

to obtain a compound of formula XXV, where $R_1$ is hydrogen, $C_1$–$C_6$ alkyl or $C_3$–$C_6$ cycloalkyl, may be carried out by treating the compound with an acidic reagent such as aqueous HBr, HI, $HBr/CH_3COOH$, $BBr_3$, $AlCl_3$, pyridine-HCl or with a basic nucleophilic reagent such as $CH_3C_6H_4S^-$ or $C_2H_5S^-$ in a suitable solvent. Suitable solvents may be methylene chloride or chloroform and the reaction may occur between −78° C. and +60° C.

(xxiv) Conversion of the compound of formula XXV to a compound of formula XXVI

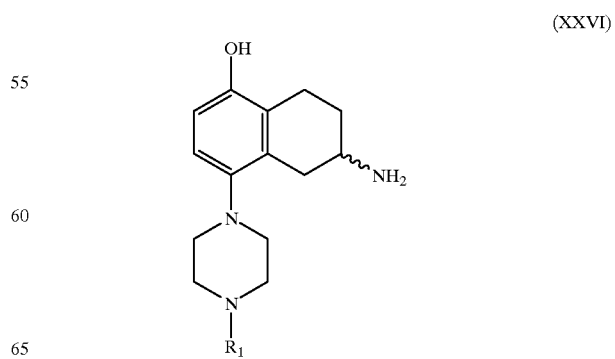

(XXVI)

where $R_1$ is hydrogen, $C_1$–$C_6$ alkyl or $C_3$–$C_6$ cycloalkyl may be carried out by hydrogenation using a catalyst containing palladium, platinum, rhodium or nickel in a suitable solvent e.g. acetic acid or ethanol at a reaction temperature between +20° C. and +120° C.

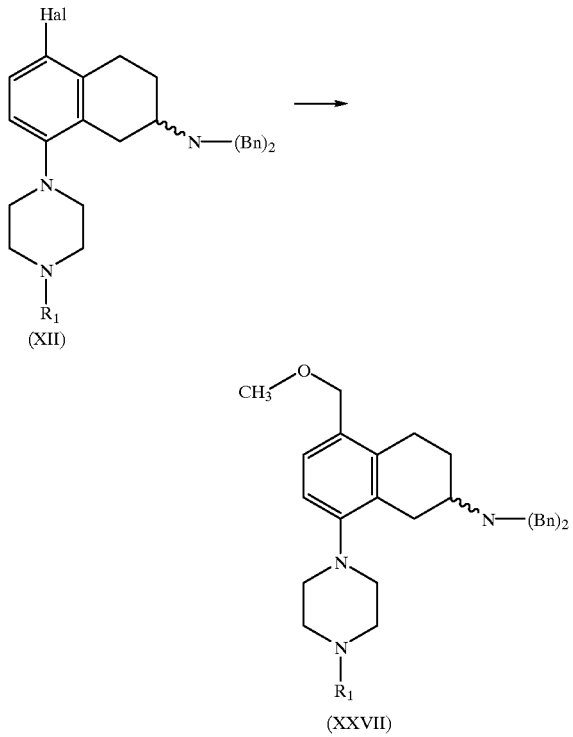

(xxv) Conversion of the compound of the formula XII, where $R_1$ is $C_1$–$C_6$-alkyl or $C_3$–$C_6$-cycloalkyl, to a compound of the formula XXVII, where $R_1$ is $C_1$–$C_6$-alkyl or $C_3$–$C_6$-cycloalkyl, may be performed by a metal-halogen exchange, in a appropriate anhydrous solvent such as tetrahydrofuran or diethyl ether using a suitable alkyl-lithium or metal e.g. buthyllithium, lithium or magnesium turnings, followed by treatment with an appropriate electrophile such as bromomethyl methyl ether and a thereafter following suitable work-up. The reaction may be performed at a reaction temperature within the range of −78° C. to room temperature.

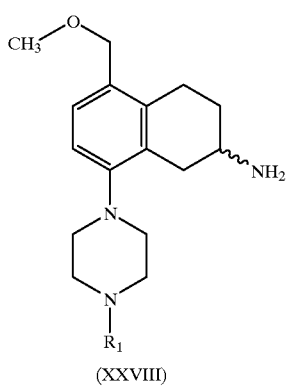

(xxvi) Conversion of a compound of formula XXVII, where $R_1$ is $C_1$–$C_6$-alkyl or $C_3$–$C_6$-cycloalkyl, to a compound of formula XXVIII, where $R_1$ is $C_1$–$C_6$-alkyl or $C_3$–$C_6$-cycloalkyl, may be performed by cleavage of the benzyl groups by hydrogenation over a suitable catalyst containing palladium, rhodium, platina or nickel, in a suitable solvent e.g. acetic acid or ethanol and the reaction may occur between +20° C. and +120° C.

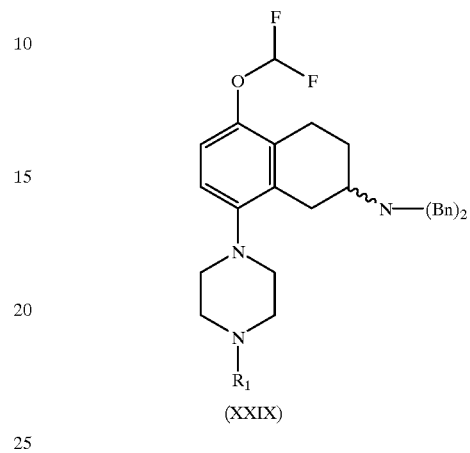

(xxvii) Alkylation of a compound of formula XXV, where $R_1$ is $C_1$–$C_6$-alkyl or $C_3$–$C_6$-cycloalkyl to obtain a compound of formula XXIX, where $R_1$ is $C_1$–$C_6$-alkyl or $C_3$–$C_6$-cycloalkyl may be carried out in a suitable solvent such as iso-propanol or dioxane with a suitable alkylating reagent such as chlorodifluoromethane in the presence of a suitable base such as NaOH or KOH at a reaction temperature between +20° C. and +80° C.

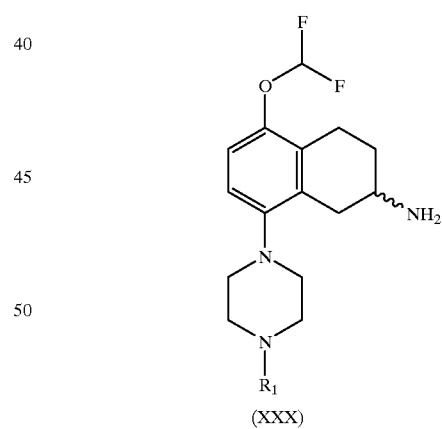

(xxviii) Conversion of a compound of formula XXIX, where $R_1$ is $C_1$–$C_6$-alkyl or $C_3$–$C_6$-cycloalkyl, to a compound of formula XXX, where $R_1$ is $C_1$–$C_6$-alkyl or $C_3$–$C_6$-cycloalkyl, may be performed by cleavage of the benzyl groups by hydrogenation over a suitable catalyst containing palladium, rhodium, platina or nickel, in a suitable solvent e.g. acetic acid or ethanol and the reaction may occur between +20° C. and +120° C.

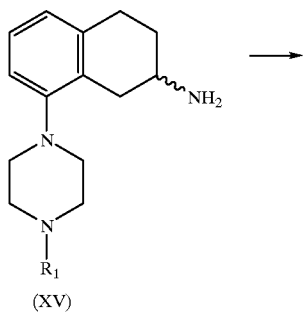

(XV)

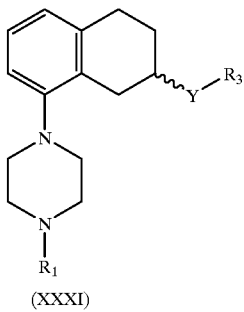

(XXXI)

(xxix) Conversion of a compound of formula XV, where $R_1$ is $C_1$–$C_6$ alkyl or $C_3$–$C_6$ cykloalkyl to a compound of formula XXXI, where Y is $NR_2CO$, $R_2$ is hydrogen and $R_3$ is $C_1$–$C_6$ alkyl, $C_3$–$C_6$ cycloalkyl or $(CH_2)_n$-aryl, wherein aryl is phenyl or a heteroaromatic ring containing one or two heteroatoms selected from N, O and S and which may be mono- or di-substituted with $R_4$ and/or $R_5$; may be carried out by acylation with an appropriate activated carboxylic acid such as an acid chloride in a suitable solvent such as methylene chloride or chloroform with a suitable base e.g. trialkylamine such as triethylamine or by using a carboxylic acid ($R_3$COOH) with an activating reagent e.g. N,N'-carbonyldiimidazole, N,N'-dicyclohexylcarbodiimide or diphenylphosphinic chloride with a suitable base such as N-methylmorpholine in a suitable solvent such as N,N-dimethylformamide or tetrahydrofuran and the reaction may be conducted at a temperature between +20° C. and +150° C.

2. In the case where Y is $CONR_2$ and X is N (i) Nitration of a compound of formula XXXII, described in Johnson D. W.; Mander L. N. Aust. J. Chem. 1974, 27, 1277–1286, either as racemate or as an enantiomer, to obtain a compound of formula XXXIII,

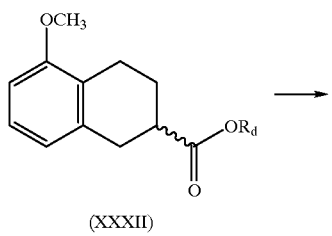

(XXXII)

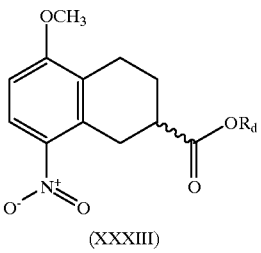

(XXXIII)

where $R_d$ is $C_1$–$C_6$ alkyl, may be carried out by aromatic electrophilic substitution using a suitable nitration reagent such as nitric acid or nitric acid and sulphuric acid in a suitable solvent e.g. acetic acid, acetic anhydride or water at a reaction temperature between −20° C. and room temperature.

(ii) Hydrolysis of a compound of formula XXXIII may be carried out under acidic conditions using acids such as $H_2SO_4$, HCl, HBr, in a suitable solvent such as $H_2O$, ethanol, methanol, acetic acid or mixtures thereof and the reaction may occur at a temperature between +20° C. and reflux or under basic conditions using bases such as NaOH or KOH in a suitable solvent such as $H_2O$, ethanol, methanol or mixtures thereof and the reaction may occur at a temperature between +20° C. and reflux, resulting in a compound of formula XXXIV

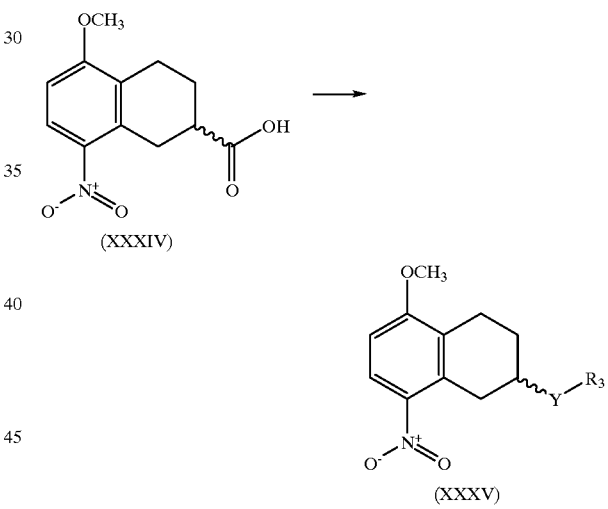

(XXXIV)

(XXXV)

(iii) Conversion of a compound of formula XXXIV to a compound of formula XXXV, where Y is $CONR_2$, may be carried out by activation of the acid function of a compound of formula XXXIV as an acid halide such as an acid chloride with a suitable base such as a trialkylamine e.g. triethylamine or by using an activating reagent such as N,N'-carbonyldiimidazole, N,N-dicyclohexylcarbodiimide or diphenylphosphinic chloride with a suitable base such as N-methylmorpholine in a suitable solvent e.g. methylene chloride, chloroform, toluene, N,N-dimethylformnamide, dioxane or tetrahydrofuran followed by the addition of an appropriate amine or aniline $HNR_2R_3$, where $R_2$ is H or $C_1$–$C_6$ alkyl and $R_3$ is $C_1$–$C_6$ alkyl, $C_3$–$C_6$ cycloalkyl or $(CH_2)_n$-aryl, wherein aryl is phenyl or a heteroaromatic ring containing one or two heteroatoms selected from N, O and S and which may be mono- or di-substituted with $R_4$ and/or $R_5$; and the reaction may occur between 0° C. and +120° C.

(iv) Conversion of the compound of formula XXXV to a compound of formula XXXVI, where Y is $CONR_2$, $R_2$ is H or $C_1$–$C_6$ alkyl and $R_3$ is $C_1$–$C_6$ alkyl, $C_3$–$C_6$ cycloalkyl or $(CH_2)_n$-aryl, wherein aryl is phenyl or a heteroaromatic ring containing one or two heteroatoms selected from N, O and S and which may be mono- or di-substituted with $R_4$ and/or $R_5$; may be carried out by

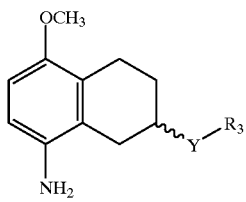

(XXXVI)

hydrogenation using a catalyst containing palladium, platina or nickel in a suitable solvent such as ethanol, methanol or acetic acid at a reaction temperature between +20° C. and +120° C.; or reduction with sodium dithionite in a suitable solvent.

3. In the case where X is CH and Y is $NR_2CO$

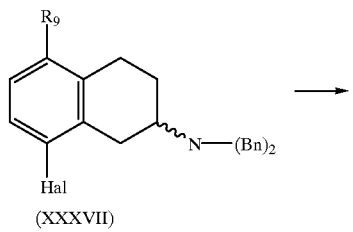

(XXXVII)

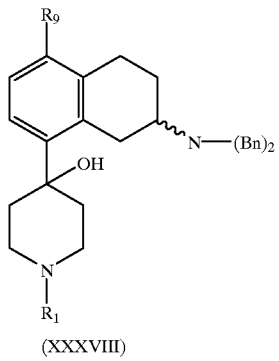

(XXXVIII)

(i) The conversion of the compound of the formula XXXVII, where $R_9$ is $C_1$–$C_6$ alkoxy, to the compound of the formula XXXVIII, where $R_1$ is $C_1$–$C_6$ alkyl or $C_3$–$C_6$ cycloalkyl and $R_9$ is $C_1$–$C_6$ alkoxy, may be performed by a metal-halogen exchange, in an appropriate anhydrous solvent such as tetrahydrofuran or diethyl ether using a suitable alkyl-lithium or metal e.g. butyllithium, lithium or magnesium turnings, followed by treatment with an appropriate N-alkylpiperidone, where alkyl ($R_1$) is $C_1$–$C_6$ alkyl or $C_3$–$C_6$ cycloalkyl such as N-methyl-4-piperidone followed by a suitable work-up. The reaction may be performed at a reaction temperature within the range of −78° C. to room temperature.

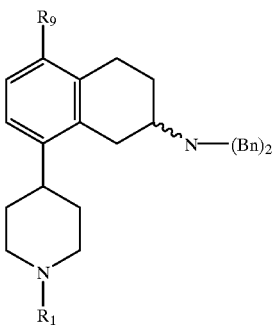

(XXXIX)

(ii) The compound of the formula XXXVIII may be reduced to the compound of the formula XXXIX by treatment with a suitable reducing agent such as sodium borohydride and a protonating agent such as $CF_3COOH$, $CF_3SO_3H$ or HCOOH in an appropriate solvent such as tetrahydrofuran or diethyl ether. The reaction may be performed at a reaction temperature between 0° C. and reflux.

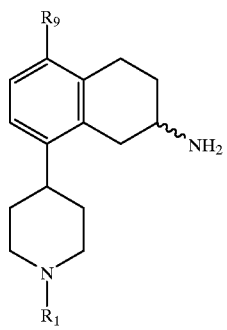

(XL)

(iii) Conversion of the compound of formula XXXIX to a compound of formula XL may be performed by hydrogenation using a catalyst such as palladium, platinum, rhodium or nickel in a suitable solvent such as acetic acid or ethanol and at a reaction temperature between +20° C. and +120° C.

4. In the case where Y is $NR_2CO$ and $R_9$ is in the 6-position (i) Benzylation of the compound of the formula XLI, either as a racemate or as an enantiomer,

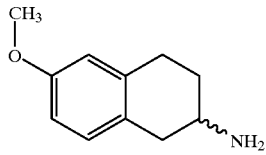

(XLI)

to obtain a compound of formula XLII may be carried out by reaction with a suitable benzylation agent e.g. a benzyl halide such as benzyl bromide or benzyl chloride or an activated alcohol e.g. benzylmesylate or benzyltosylate. The reaction may be carried out using a salt or the base of compound XLI in a suitable solvent e.g. N,N-dimethylformamide, acetone or acetonitrile with a suitable base e.g. NaOH, $NaHCO_3$, $K_2CO_3$ or a trialkylamine such as triethylamine at a temperature within the range of +20° C. to +150° C. The presence of a suitable catalyst e.g. potassium iodide or sodium iodide, may increase the speed of the reaction.

(ii) Demethylation of the compound of formula XLII

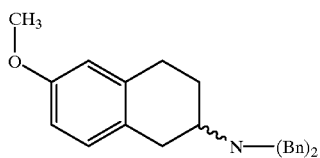
(XLII)

to obtain a compound of formula XLIII may be carried out by treating the compound with an acidic reagent such as aqueous HBr, HI, HBr/CH$_3$COOH, BBr$_3$, AlCl$_3$, pyridine-HCl or with a basic nucleophilic reagent such as CH$_3$C$_6$H$_4$S$^-$ or C$_2$H$_5$S$^-$ in a suitable solvent. Suitable solvents may be methylene chloride or chloroform and the reaction may occur between −78° C. and +60° C.

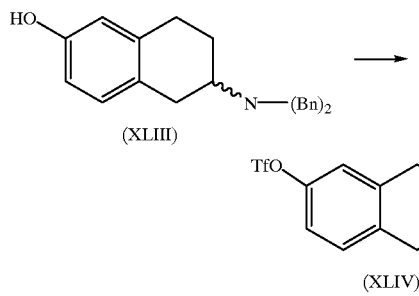
(XLIII)

(XLIV)

(iii) Conversion of the compound of formula XLIII to a compound of formula XLIV may be carried out with a compound such as trifluoromethanesulfonic anhydride in a suitable solvent such as methylene chloride or carbon tetrachloride in the presence of a base such as 2,4,6-collidine, triethylamine or pyridine at a reaction temperature within the range of −78° C. to room temperature.

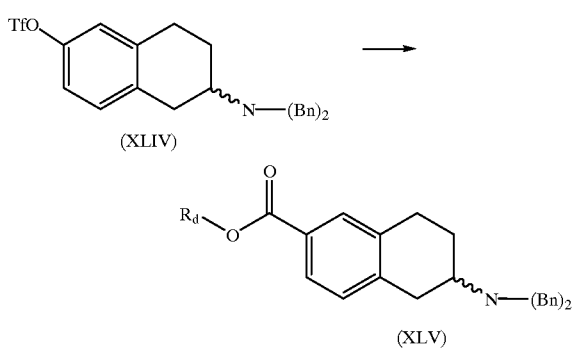
(XLIV)

(XLV)

(iv) Conversion of the compound of formula XLIV to a compound of formula XLV where R$_d$ is a C$_1$–C$_6$ alkyl group may be carried out in a suitable solvent such as dimethylsulphoxide or N,N-dimethylformamide with a suitable base such as a trialkylamine e.g. triethylamine in the presence of a suitable catalyst such as Pd(OAc)$_2$ and a suitable ligand such as triphenylphosphine, 1,1'-bis(diphenylphosphino)ferrocene or 1,3-bis(diphenylphosphino)propane and a suitable alcohol such as methanol, ethanol or propanol under a carbon monoxide atmosphere at a reaction temperature between 40° C. and 120° C.

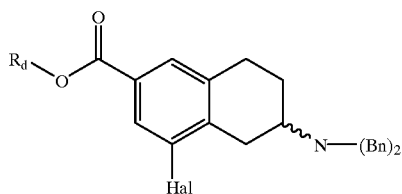
(XLVI)

(v) Halogenation of the compound of formula XLV, where R$_d$ is a C$_1$–C$_6$ alkyl group, to obtain a compound of formula XLVI may be carried out with a suitable halogenation reagent such as 1,3-dibromo-5,5-dimethylhydantoin. The reaction may be carried out using the salt or the base of the compound XLV in a appropriate solvent e.g. CF$_3$SO$_3$H or H$_2$SO$_4$ and at a reaction temperature between 30° C. and 150° C.

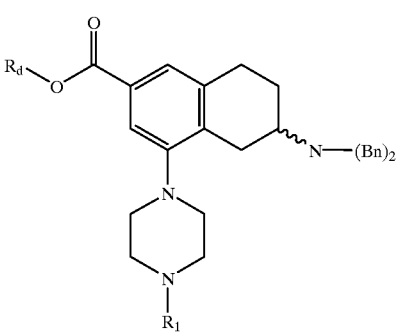
(XLVII)

(vi) Conversion of the compound of formula XLVI to a compound of formula XLVII, where R$_1$ is C$_1$–C$_6$ alkyl or C$_3$–C$_6$ cycloalkyl may be carried out by the reaction with a compound of formula XXII, where R$_1$ is C$_1$–C$_6$ alkyl or C$_3$–C$_6$ cycloalkyl.

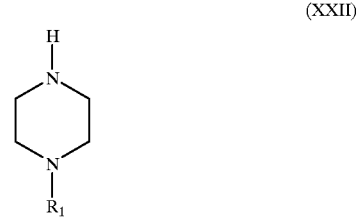
(XXII)

The process may be carried out in a suitable solvent e.g, an aprotic solvent such as benzene, toluene, dioxane, tetrahydrofuran or N,N-dimethylformamide with a suitable base such as sodium tert-butoxide or lithium bis(trimethylsilyl)amide in the presence of a suitable palladium catalyst such as PdX$_2$, L$_2$Pd(O) or L$_2$PdX$_2$ where X stands for a halogen such as chlorine or bromine and L stands for a suitable ligand such as triphenylphosphine, tri-o-tolylphosphine, trifurylphosphine, triphenylarsine or dibenzylideneacetone and with or without an addition of a ligand L' such as triphenylphosphine, tri-o-tolylphosphine, trifurylphosphine, 2,2'-bis(diphenylphosphino)-1,1'-binaphthalen (either as a racemate or as an enantiomer) or triphenylarsine and the reaction may occur at a temperature between +20° C. and +150° C.

(ix) Nitration of a compound of formula XLIX

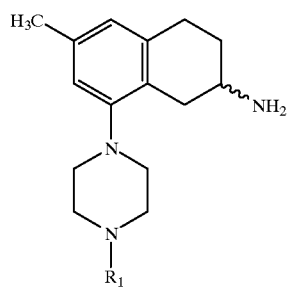

(XLVIII)

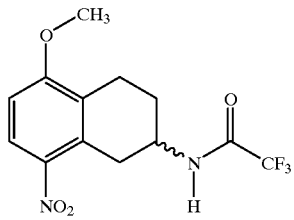

(L)

to obtain a compound of formula L may be carried out by treating the compound with a suitable nitrating agent such as nitric acid in a suitable solvent such as acetic acid and the reaction may occur between 0° C. and +30° C.

(vii) Conversion of compound of formula XLVII to a compound of formula XLVIII may be carried out by the reduction of the alkyl ester in a suitable solvent such as diethyl ether or tetrahydrofuran with an appropriate reductive agent such as lithium aluminum hydride and the reaction may occur between +20° C. and reflux, followed by cleavage of the benzyl groups and reduction of the benzyl alcohol by hydrogenation over a suitable catalyst containing palladium, rhodium, platina or nickel, in a suitable solvent e.g. acetic acid or ethanol and the reaction may occur between +20° C. and +120° C. Compound of formula XLVIII may also be prepared by, (viii) Compound of formula XLVIII may also be prepared by protection of the amino group of the compound of the formula XVIII, either as a racemate or as an enantiomer,

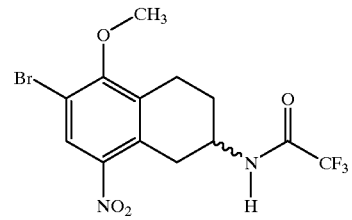

(LI)

(x) Halogenation of the compound of formula L to obtain a compound of formula LI may be carried out with a suitable halogenation reagent such as N-bro mosuccinimide or 1,3-dibromo-5,5-dimethylhydantoin. The reaction may be carried out in a appropriate solvent such as chloroform or methylene chloride with or without a suitable acid e.g. $CF_3SO_3H$ or $H_2SO_4$ and at a reaction temper ature between 0° C. and +80° C.

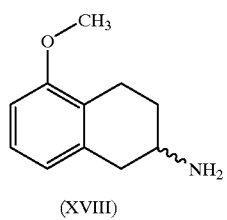

(XVIII)

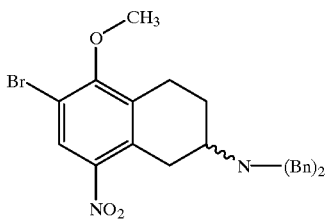

(LII)

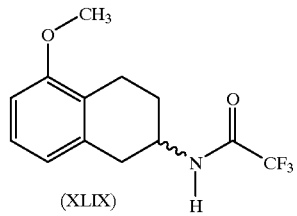

(XLIX)

to obtain a compound of formula XLIX by the reaction with a suitable acylating agent e.g. trifluoroacetyl chloride or trifluoroacetic anhydride. The reaction may be carried out using a salt or the base of compound XVIII in a suitable solvent e.g. methylene chloride or chloroform with a suitable base e.g. NaOH, $NaHCO_3$, $K_2CO_3$ or a trialkylamine such as triethylamine at a temperature within the range of −20° C. to +80° C.

(xi) Conversion of a compound of formula LI to a compound of formula LII may be carried out by a) hydrolysis of the amide in the compound of formula LI under acidic conditions using acids such as $H_2SO_4$, HCl or HBr in a suitable solvent e.g. $H_2O$, ethanol, methanol or mixtures thereof and the reaction may occur between +20° C. and +100° C. or under basic conditions using bases such as NaOH or KOH in a suitable solvent e.g. $H_2O$, ethanol, methanol or mixtures thereof and the reaction may occur between +20° C. and +100° C.

Hydrolysis is followed by b) benzylation of the primary amine by reaction with a suitable benzylation agent e.g. a benzyl halide such as benzyl bromide or benzyl chloride or an activated alcohol e.g. benzylmesylate or benzyltosylate. The reaction may be carried out in a suitable solvent e.g. N,N- dimethylformamide, acetone or acetonitrile with a suitable base e.g. NaOH, NaHCO₃, K₂CO₃ or a trialkylamine such as triethylamine at a temperature within the range of +20° C. to +150° C., resulting in the compound of formula LII. The presence of a suitable catalyst e.g. potassium iodide or sodium iodide, may increase the speed of the reaction.

(xii) Reduction of a compound of formula LII to obtain a compound of formula LIII may be carried out in a suitable solvent such as mixtures of methanol/water or ethanol/water in the presence of a suitable reducing agent e.g. sodium hydrosulfite at a reaction temperature between +20° C. to +100° C.

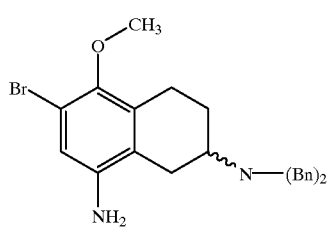

(LIII)

(xiii) Conversion of compound of formula LIII to a compound of formula LIV

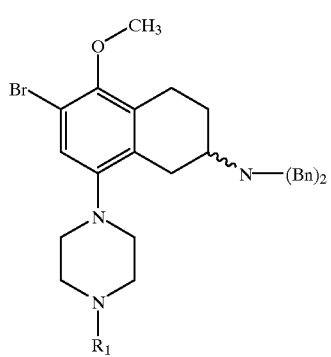

(LIV)

may be carried out by the reaction with a compound of formula XI

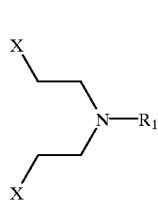

(XI)

where X stands for a leaving group, e.g. a halogen such as chlorine or bromine or an alkane- or arenesulfonyloxy group such as p-toluenesulfonyloxy group and $R_1$ is $C_1$–$C_6$-alkyl or $C_3$–$C_6$ cycloalkyl. The process may be carried out in a suitable solvent such as ethanol, buthanol, N,N-dimethylformamide, acetonitrile or a mixture of water and acetonitrile with a suitable base e.g. K₂CO₃, NaHCO₃ or KOH and the reaction may occur between +20° C. and +150° C.

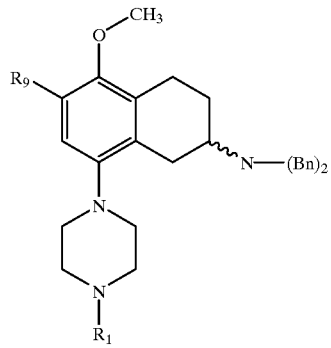

(LV)

(xiv) Conversion of the compound of formula LIV to a compound of formula LV, where $R_1$ is $C_1$–$C_6$ alkyl or $C_3$–$C_6$ cycloalkyl and $R_9$ is $C_1$–$C_6$ alkyl, may be carried out by a metal-halogen exchange, in a appropriate anhydrous solvent such as tetrahydrofuran or diethyl ether using a suitable alkyl-lithium or metal e.g. buthyllithium, lithium or magnesium turnings, followed by treatment with appropriate alkyl halide such as methyl iodide, ethyl bromide or propyl iodide and the reaction may be performed at a reaction temperature within the range of −78° C. to room temperature or treatment with other electrophiles such as acetaldehyde or methyl chloroformate and a thereafter following suitable work-up. The reaction may be performed at a reaction temperature within the range of −78° C. to room temperature.

In the case where acetaldehyde is used as electrophile, the above reaction is followed by reduction of the benzyl alcohol by hydrogenation over a suitable catalyst containing palladium, rhodium, platina or nickel, in a suitable solvent e.g. acetic acid or ethanol and the reaction may occur between +20° C. and +120° C.

In the case where methyl chloroformate is used as electrophile, the above reaction is followed by reduction of the methyl ester in a suitable solvent such as diethyl ether or tetrahydrofuran with an appropriate reductive agent such as lithium aluminum hydride and the reaction may occur between +20° C. and reflux, followed by reduction of the benzyl alcohol by hydrogenation over a suitable catalyst containing palladium, rhodium, platina or nickel, in a suitable solvent e.g. acetic acid or ethanol and the reaction may occur between +20° C. and +120° C.

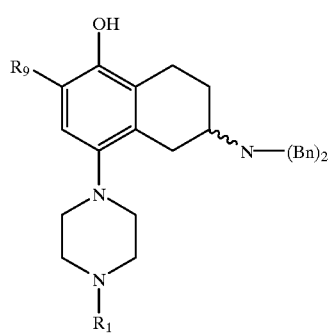

(LVI)

(xv) Demethylation of the compound of the formula LV to obtain a compound of formula LVI may be performed by treating the compound with an acidic reagent such as aqueous HBr, HI, HBr/acetic acid, BBr$_3$, AlCl$_3$, pyridine-HCl or with a basic nucleophilic reagent such as C$_2$H$_5$S$^-$ or CH$_3$C$_6$H$_4$S$^-$ in a suitable solvent. Suitable solvents may be acetic acid, methylene chloride or chloroform and the reaction may occur between −78° C. and +60° C.

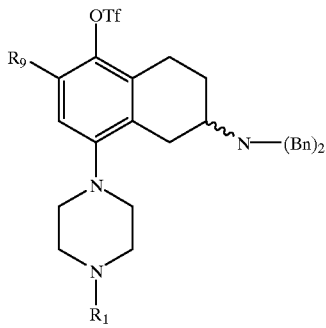

(LVII)

(xvi) Conversion of the compound of formula LVI to a compound of formula LVII may be carried out by treatment with a compound such as trifluoromethanesulfonic anhydride in a suitable solvent such as methylene chloride or carbon tetrachloride in the presence of a base such as 2,4,6-collidine, triethylamine or pyridine at a reaction temperature within the range of −78° C. to room temperature.

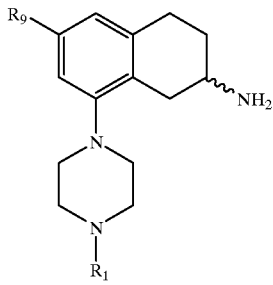

(XLVIII)

(xvii) Conversion of the compound of formula LVII to a compound of formula XLVIII may be performed by a) treatment of compound of formula LVII with a suitable palladium catalyst such as palladium(II)acetate and a suitable ligand such as triphenylphosphine in the presence of a suitable acid e.g. formic acid in a suitable solvent such as N,N-dimethylformamide at a reaction temperature between +20° C. and +120° C., followed by b) reaction in a suitable solvent such as methanol in the presence of ammonium formate and Pd/C at a reaction temperature between +20° C. and reflux, resulting in the compound of formula XLVIII.

Methods of Preparation of End Products

Another object of the invention is a process A(i), A(ii), B or C for the preparation of the compound of general formula I by A(i)

acylation, in the case where R$_1$ is C$_1$–C$_6$ alkyl or C$_3$–C$_6$ cycloalkyl, Y is NR$_2$CO, R$_2$ is hydrogen and X, R$_3$ and R$_9$ are as defined in general formula I above with the exception of when R$_9$ is a substituent that is susceptible to certain acylating agents, of a compound of formula A,

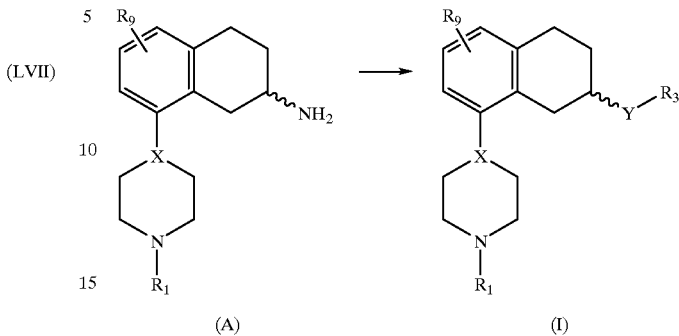

(A)  (I)

with an activated carboxylic acid R$_3$—COL where L is a leaving group or by using a carboxylic acid R$_3$—COOH with an activating reagent.

Thus, the acylation according to the process A(i) may be carried out with an appropriate activated carboxylic acid, R$_3$COL where R$_3$ is as defined above and L is a leaving group, such as halogen e.g. chlorine, in a suitable solvent such as methylene chloride or chloroform with a suitable base e.g. trialkylamine such as triethylamine at a temperature between −20° C. and reflux temperature or by using an carboxylic acid, R$_3$COOH wherein R$_3$ is as defined above with an activating reagent e.g. N,N'-carbonyldiimidazole, N,N'-dicyclohexylcarbodiimide or diphenylphosphinic chloride with a suitable base such as N-methylmorpholine in a suitable solvent such as N,N-dimethylformamide or tetrahydrofuran and the reaction may be conducted at a temperature between +20° C. and +150° C.

A(ii)

acylation, in the case where R$_1$ is hydrogen, Y is NR$_2$CO, R$_2$ is hydrogen, R$_c$ is a protecting group and X, R$_3$ and R$_9$ are as defined in general formula I above with the exception of when R$_9$ is a substituent that is susceptible to certain acylating agents, of a compound of formula B

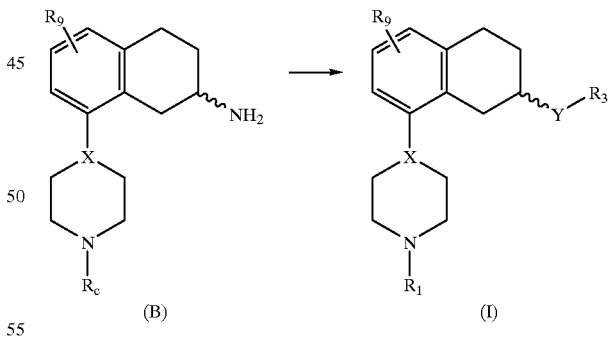

(B)  (I)

with an activated carboxylic acid R$_3$—COL where L is a leaving group or by using a carboxylic acid R$_3$—COOH with an activating reagent, followed by the removal of the protecting group R$_c$;

Thus, the acylation according to the process A(ii) may be carried out with an appropriate activated carboxylic acid, R$_3$COL where R$_3$ is as defined above and L is a leaving group, such as halogen e.g. chlorine, in a suitable solvent such as methylene chloride or chloroform with a suitable base e.g. trialkylamine such as triethylamine at a temperature between −20° C. and reflux temperature or by using an carboxylic acid, R₃COOH wherein R₃ is as defined above with an activating reagent e.g. N,N'-carbonyldiimidazole, N,N'-dicyclohexylcarbodiimide or diphenylphosphinic chloride with a suitable base such as N-methylmorpholine in a suitable solvent such as N,N-dimethylformamide or tetrahydrofuran and the reaction may be conducted at a temperature between +20° C. and +150° C., followed by removal of the protecting group $R_c$ by hydrolysis in a suitable solvent such as methylene chloride or chloroform with a suitable acid such as trifluoroacetic acid at a temperature between +20° C. and +60° C.

B reacting, in the case where Y is CONR₂, R₂, R₃ and R₉ is as defined in general formula I above with the exception of when R₉ is a substituent that is susceptible to certain alkylating reaoents XI, a compound of formula C

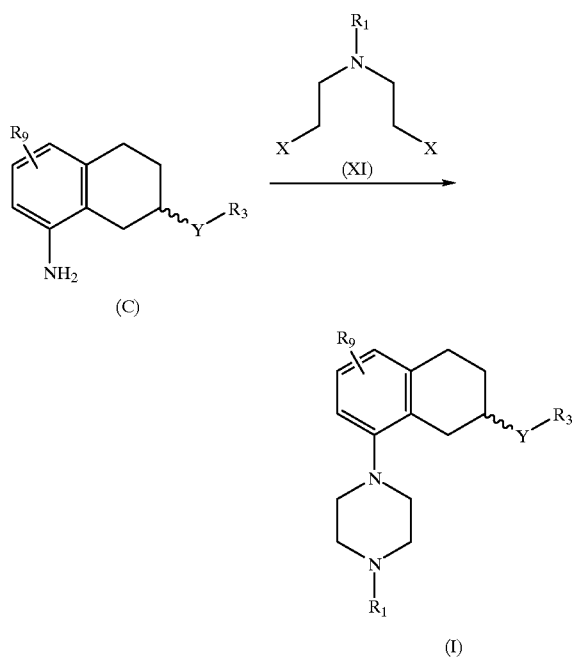

with a compound of formula XI wherein X is a leaving group.

Thus, the reaction according to the process B may be carried out with a compound of formula XI wherein R₁ is as defined in general formula I and X is a leaving group, e.g. a halogen such as chlorine or bromine or an alkane- or arenesulfonyloxy group such as p-toluene-sulfonyloxy group. The process may be carried out in a suitable solvent such as ethanol, butanol, N,N-dimethylformamide, acetonitrile or a mixture of water and acetonitrile with or without a suitable base e.g. K₂CO₃, NaHCO₃ or KOH and the reaction may occur between +20° C. and +150° C.

C reacting, in the case where Y is NR₂CO, R₉ is halogen and Rl, R₂ and R₃ is as defined in general formula I above a compound of formula D

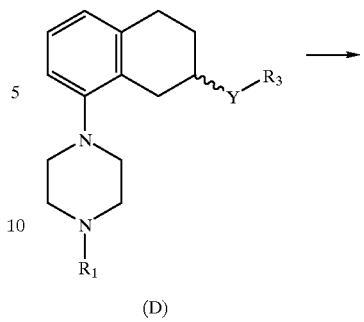

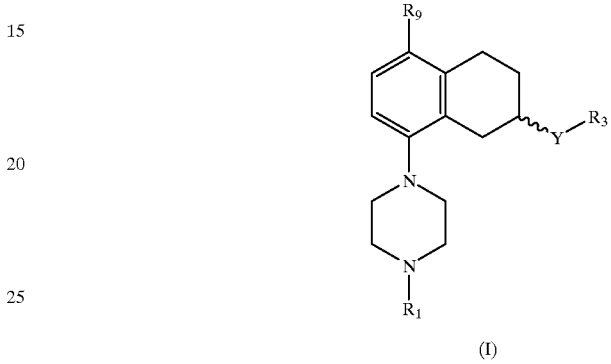

with a suitable halogenation agent such as Br₂, Cl₂, I₂, ICl, or SO₂Cl₂.

Thus, the reaction according to the process C may be carried out by aromatic electrophilic substitution using a suitable halogenation agent such as Br₂, Cl₂, I₂, ICl, or SO₂Cl₂. The reaction may be carried out using the salt or the base of the compound D in an appropriate solvent e.g. acetic acid, HCl/ethanol or water with or without a suitable base e.g. alkali metal acetate such as sodium acetate and at a reaction temperature between −20° C. and room temperature.

Intermediates

Another object of the invention is a compound having the formula

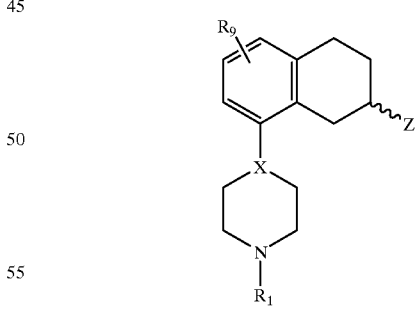

wherein
X=N or CH;
Z=NH₂ or COOH;
R₁ is H, C₁–C₆ alkyl or C₃–C₆ cycloalkyl;
R₉ is C₁–C₆ alkyl, C₃–C₆ cycloalkyl, OCF₃, OCHF₂, OCH₂F, halogen, CN, CF₃, OH, C₁–C₆ alkoxy, C₁–C₆ alkoxy-C₁–C₆ alkyl, NR₆R₇, SO₃CH₃, SO₃CF₃, SO₂NR₆R₇, an unsubstituted or substituted heterocyclic or heteroaromatic ring containing one or two heteroatoms selected from N and O, wherein the substituent(s) is(are) $C_1$–$C_6$ alkyl; or $COR_8$; wherein $R_6$ is H, $C_1$–$C_6$ alkyl or $C_3$–$C_6$ cycloalkyl;

$R_7$ is H, $C_1$–$C_6$ alkyl or $C_3$–$C_6$ cycloalkyl; and $R_8$ is $C_1$–$C_6$ alkyl, $C_3$–$C_6$ cycloalkyl, $CF_3$, $NR_6R_7$, phenyl, a heteroaromatic ring containing one or two heteroatoms selected from N, O and S or a heterocyclic ring containing one or two heteroatoms selected from N, O, S, SO and $SO_2$ wherein $R_6$ and $R_7$ are as defined above and

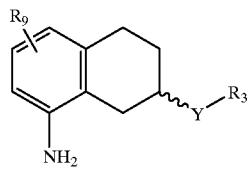

wherein

Y is $CONR_2$ wherein $R_2$ is H or $C_1$–$C_6$ alkyl.

$R_3$ is $C_1$–$C_6$ alkyl, $C_3$–$C_6$ cycloalkyl or $(CH_2)_n$-aryl, wherein aryl is phenyl or a heteroaromatic ring containing one or two heteroatoms selected from N, O and S and which may be mono- or di-substituted with $R_4$ and/or $R_5$; wherein with $R_4$, $R_5$ and n are as defined above.

$R_9$ is $C_1$–$C_6$ alkyl, $C_3$–$C_6$ cycloalkyl, $OCF_3$, $OCHF_2$, $OCH_2F$, halogen, CN, $CF_3$, OH, $C_1$–$C_6$ alkoxy, $C_1$–$C_6$ alkoxy-$C_1$–$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent(s) is(are) $C_1$–$C_6$ alkyl; or $COR_8$; wherein $R_6$, $R_7$ and $R_8$ are as defined above.

WORKING EXAMPLES

The following examples will describe, but not limit, the invention.

Example 1

(R)-2-N,N-Dibenzylamino-8-methoxy-1,2,3,4-tetrahydronaphthalene

To a solution of (R)-8-methoxy-2-amino-1,2,3,4-tetrahydronaphthalene hydrochloride (24 g, 0.11 mol) in acetonitrile (600 mL) were added potassium carbonate (53 g, 0.39 mol), potassium iodide (catalytic amount) and benzyl bromide (34 mL, 0.28 mol). The reaction mixture was stirred at reflux for a period of 35 h.

After the precipitate was filtered off and the acetonitrile removed in vacuo, the residue was partitioned between diethyl ether and water. The organic phase was separated, dried ($Na_2SO_4$) and evaporated in vacuo to give a crude product which was purified on a silica gel column using hexane/ethyl acetate, (3:1) as the eluent. Yield: 36 g (91%) of the title compound as a white solid: mp 105–107° C.; $[\alpha]^{21}_D$+124° (c 1.0, chloroform); EIMS (70 eV) m/z (relative intensity) 357 (100, M+).

Example 2

(R)-7-N,N-Dibenzylamino-5,6,7,8-tetrahydro-1-naphthol (R)-2-N,N-Dibenzylamino-8-methoxy-1,2,3,4-tetrahydronaphthalene (43 g, 0.12 mol) was dissolved in diethyl ether (800 mL) and an excess of an ethereal HCl solution was added dropwise. The precipitate was filtered and dried in vacuo to give a white solid. This crude product (42 g, 0.11 mol) was dissolved in anhydrous methylene chloride (1 L) and cooled to −60° C. To the solution was boron tribromide (16 mL, 0.15 mol), dissolved in anhydrous methylene chloride (100 mL), added dropwise. The reaction temperature was allowed to reach −5° C. and was kept there overnight. To the ice-cooled solution was a 2 M aqueous ammonium hydroxide solution added dropwise and the mixture was extracted, twice, with methylene chloride. The combined organic phases were dried ($Na_2SO_4$), filtered and the solvent removed in vacuo to give a crude residue. Chromatography on silica (eluent: methylene chloride) gave 34 g (93% yield) of the title compound as a viscous clear oil: $[\alpha]^{21}_D$+118° (c 1.5, chloroform); EIMS (70 eV) m/z (relative intensity) 343 (53, M+).

Example 3

(R)-2-(7-N,N-Dibenzylamino-5,6,7,8-tetrahydro-1-naphthyloxy)-2-methylpropanamide (R)-2-N,N-Dibenzylamino-5,6,7,8-tetrahydro-1-naphthol (10 g, 29 mmol) was stirred in anhydrous dioxane (150 mL) with sodium hydride (80% in oil, 0.96 g, 32 mmol) for 1 h. 2-Bromo-2-methylpropanamide (4.8 g, 29 mmol; described in: Coutts, I. G. C.; Southcott, M. R. *J. Chem. Soc. Perkin Trans.* 1 1990, 767-770) was added and the reaction mixture was heated at 100° C. for 2.5 h. After cooling, the precipitated sodium bromide was filtered off, the filtrate evaporated in vacuo and the residue was partitioned between water and methylene chloride. The organic phase was separated, dried ($Na_2SO_4$), filtered and evaporated to give a crude product which was purified on a silica gel column using methylene chloride as the eluent. Yield: 9.6 g (76%) of the title compound as white crystals: mp 125–126° C.; $[\alpha]^{21}_D$+98° (c 1.1, chloroform); EIMS (70 eV) m/z (relative intensity) 428 (13, M+).

Example 4

(R)-N-(7-N,N-Dibenzylamino-5,6,7,8-tetrahydro-1-naphthyl)-2-hydroxy-2-methylpropanamide To a solution of (R)-2-(7-N,N-dibenzylamino-5,6,7,8-tetrahydro-1-naphthyloxy)-2-methylpropanamide (9.1 g, 21 mmol) in anhydrous 1,3-dimethyl-3,4,5,6-tetrahydro-2(1H)-pyrimidone (10 mL) and dry N,N-dimethylformamide (100 mL) was added sodium hydride (80% in oil, 1.4 g, 47 mmol) and the reaction was heated at 130° C. for 8 h. The solution was poured into a mixture of ice and water and extracted three times with ethyl acetate. The combined organic phases were dried ($Na_2SO_4$), filtered and evaporated in vacuo. Chromatography on silica (eluent: chloroform/ethanol saturated with $NH_3$; 100:0.5) gave 7.6 g (84% yield) as white crystals: mp 134–135° C.; $[\alpha]^{21}_D$+130° (c 1.1, chloroform); EIMS (70 eV) m/z (relative intesity) 428 (1, M+).

Example 5

(R)-2-N,N-Dibenzylamino-8-amino-1,2,3,4-tetrahydronaphthalene (R)-N-(7-N,N-Dibenzylamino-5,6,7,8-tetrahydro-1-naphthyl)-2-hydroxy-2-methylpropionamide (7.4 g, 17 mmol) was dissolved in a mixture of ethanol (200 mL) and a 20% HCl aqueous solution (300 mL) and heated to reflux for 8 h. The ethanol was evaporated in vacuo and the remaining solution was washed twice with diethyl ether and cooled on ice-bath. After alkalization with a 45% aqueous solution of sodium hydroxide the mixture was extracted with methylene chloride. The combined organic phases were dried (Na$_2$SO$_4$), filtered and evaporated in vacuo. Purification on a silica gel column using chloroform as the eluent gave 3.8 g (76% yield) of the title compound as a light-brown oil: $[\alpha]^{21}_D$+124° (c 0.9, chloroform); EIMS (70 eV) m/z (relative intensity) 342 (92, M$^+$).

Example 6

(R)-1-(7-N,N-Dibenzylamino-5,6,7,8-tetrahydro-1-naphthyl)-4-N-methylpiperazine-2,6-dione 1,1'-Carbonyldiimidazole (6.0 g, 37 mmol) was added to a stirred suspension of methyliminodiacetic acid (2.7 g, 18 mmol) in anhydrous tetrahydrofuran (250 mL). The reaction mixture was heated at reflux for 1.5 h. (R)-2-N,N-Dibenzylamino-8-amino-1,2,3,4-tetrahydronaphthalene (5.7 g, 17 mmol) was then added and stirring at reflux was continued for 17 h. An additional amount of 1,1'-carbonyldiimidazole (2.9 g, 18 mmol) was added and heating at reflux was continued for another 17 h. The solvent was evaporated in vacuo and the crude product was purified on a silica gel column using chloroforn/ethanol saturated with NH$_3$ (100:0.5) as the eluent. Yield: 6.6 g (87%) of the title compound as an oil: $[\alpha]^{21}_D$+90° (c 0.52, chloroform); EIMS (70 eV) m/z (relative intensity) 453 (8, M$^+$).

Example 7

(R)-2-N,N-Dibenzylamino-8-(4-methylpiperazin-1-yl)-1,2,3,4-tetrahydronaphthalene (R)-1-(7-N,N-Dibenzylarino-5,6,7,8-tetrahydro-1-naphthyl)-4-methylpiperazine-2,6-dione (1.4 g, 3.1 mmol) was added to a suspension of lithium aluminium hydride (0.57 g, 15 mmol) in anhydrous diethyl ether (70 mL). The reaction mixture was heated at reflux for 7 h. The reaction was quenched by the addition of water (0.60 mL), 15% aqueous sodium hydroxide (0.60 mL) and again water (1.8 mL). The mixture was filtered, dried (Na$_2$SO$_4$) and evaporated in vacuo. Purification on a silica gel column using chloroform/ethanol saturated with NH$_3$ (100:2) as the eluent gave 1.0 g (79% yield) of the title compound as a viscous oil: $[\alpha]^{21}_D$+53° (c 0.5, chloroform); EIMS (70 eV) m/z (relative intensity) 425 (2, M$^+$).

Example 8

(R)-5-Bromo-2-N,N-dibenzylamino-8-(4-methylpiperazin-1-yl)-1,2,3,4-tetrahydronaphthalene To a solution of (R)-2-N,N-dibenzylamino-8-(4-methylpiperazin-1-yl)-1,2,3,4-tetrahydronaphthalene (2.8 g, 6.5 mmol) and sodium acetate (6.8 g, 83 mmol) in acetic acid (100 mL) was bromine (370 µL, 7.2 mmol) added in one portion and the reaction was stirred for 5 min. The solvent was evaporated in vacuo and the remaining solid was partitioned between water and methylene chloride and cooled on ice-bath. The water phase was alkalized with 2 M aqueous solution of sodium hydroxide and the phases were separated. The organic phase was dried (Na$_2$SO$_4$), filtered and evaporated in vacuo to give a crude product which was purified on a silica gel column using chloroform/ethanol saturated with NH$_3$ (100:2) as the eluent. Yield: 2 g (61%) of a viscous brown oil: EIMS (70 eV) m/z (relative intensity) 503 and 505 (0.6, M$^+$)

Example 9

(R)-2-N,N-Dibenzylamino-5-hydroxy-8-(4-methylpiperazin-1-yl)-1,2,3,4-tetrahydronaphthalene.

To a solution of (R)-2-N,N-dibenzylamino-5-methoxy-8-(4-methylpiperazin-1-yl)-1,2,3,4-tetrahydronaphthalene (2.1 g, 4.7 mmol) in acetic acid (40 mL) was added an 47% aqueous hydrobromic acid solution (20 mL) and the reaction was heated at reflux for 7 h. The solvent was evaporated in vacuo and the residue was dissolved in water (75 mL) and cooled on ice-bath. The solution was alkalized with an 2 M aqueous solution of sodium hydroxide and extracted with methylene chloride. The phases were separated and the organic phase was dried (Na$_2$SO$_4$), filtered and evaporated in vacuo. Purification on a silica gel column using chloroform/methanol/concentrated ammonium hydroxide (95:5:0.5) as the eluent gave 1.8 gram (89% yield) of the title compound as a viscous oil: EIMS (70 eV) m/z (relative intensity) 441 (7, M$^+$)

Example 10

(R)-2-Amino-5-hydroxy-8-(4-methylpiperazin-1-yl)-1,2,3,4-tetrahydronaphthalene

To a solution of (R)-2-N,N-dibenzylamino-5-hydroxy-8-(4-methylpiperazin-1-yl)-1,2,3,4-tetrahydronaphthalene (0.70 g, 1.6 mmol) and ammonium formate (2.4 g, 38 mmol) in methanol (50 mL) was added palladium (10%) on activated carbon. The mixture was refluxed for 4 h and the palladium was then filtered off. The solvent was evaporated in vacuo and the residue was partitioned between diethyl ether and 2 M ammonium hydroxide. The organic phase was separated, dried (Na$_2$SO$_4$), filtered and evaporated in vacuo. The residue was washed with water and diethyl ether and was then dried in vacuo. Yield: 200 mg (44%) of grey crystals: mp 238–239° C.; $[\alpha]^{21}_D$+43° (c=0.5, chloroform); EIMS (70 eV) m/z (relative intensity) 261 (65, M$^+$)

Example 11

(R)-N-[5-Hydroxy-8-(4-methypiperazin-1-yl)-1,2,3,4-tetrahydro-2-naphthyl]-4-butoxybenzamide To an ice-cooled solution of (R)-2-amino-5-hydroxy-8-(4-methylpiperazin-1-yl)-1,2,3,4-tetrahydronaphthalene (100 mg, 0.38 mmol) and triethylamine (79 µL, 0.57 mmol) in N,N-dimethylformamide (30 mL) was 4-butoxybenzoyl chloride in N,N-dimethylformamide (5 mL) added dropwise. After the addition the reaction was stirred at ambient temperature for 15 min. The solvent was evaporated in vacuo and the residue was purified on a silica gel column using chloroform/methanol/concentrated ammonium hydroxide (95:5:0.5) as the eluent. Yield: 73 mg (44%) as an amorphous solid: mp 125° C. (decomp.); $[\alpha]^{21}_D$−20° (c=0.25, chloroform); EIMS (70 eV) m/z (relative intensity) 437 (16, M$^+$).

Example 12

(R)-2-N,N-Dibenzylamino-8-(piperazin-1-yl)-1,2,3,4-tetrahydronaphthalene (R)-2-N,N-Dibenzylamino-8-amino-1,2,3,4-tetrahydronaphthalene (9.8 g, 39 mmol) and bis-(2-chloroethyl)amine hydrochloride (5.5 g, 32 mmol) was dissolved in n-butanol (80 mL). The reaction mixture was stirred at 100° C. and after 65 h the mixture was filtered and the solvent evaporated in vacuo. Purification on a silica gel column using chloroform/methanol/concentrated ammonium hydroxide (95:5:0.5) as the eluent gave 6.0 g (51% yield) of the title compound as a viscous oil: $[\alpha]^{21}_D +72°$ (c 1.0, chloroform); EIMS (70 eV) m/z (relative intensity) 411 (2, M⁺).

Example 13

(R)-2-Amino-8-(piperazin-1-yl)-1,2,3,4-tetrahydronaphthalene

To a solution of (R)-2-N,N-dibenzylamino-8-(piperazin-1-yl)-1,2,3,4-tetrahydronaphthalene (5.5 g, 13 mmol) in methanol (400 mL) were added ammonium formate (20 g, 0.32 mol) and palladium (10%) on activated carbon (1.9 g). The mixture was refluxed for 1 h and the palladium was then filtered off. The solvent was evaporated in vacuo and the residue was partitioned between methylene chloride and a 2 M ammonium hydroxide solution. The organic phase was separated, dried ($Na_2SO_4$), filtered and evaporated in vacuo to give a crude product which was purified on a silica gel column using chloroform/ethanol/concentrated ammonium hydroxide (80:20:2.5) as the eluent. Yield: 2.4 g (76%) of the title compound as an oil: $[\alpha]^{21}_D +9.9°$ (c 1.0, chloroform); EIMS (70 eV) m/z (relative intensity) 231 (24, M⁺).

Example 14

(R)-2-Amino-5-bromo-8-(piperazin-1-yl)-1,2,3,4-tetrahydronaphthalene

The title compound was prepared from (R)-2-amino-8-(piperazin-1-yl)-1,2,3,4-tetrahydronaphthalene following the general method of Example 8. Purification on a silica gel column using methylene chloride/ethanol/concentrated ammonium hydroxide (80:20:2) as the eluent gave 0.8 g (67% yield) of a viscous light brown oil: $[\alpha]^{21}_D -6.2°$ (c=1, chloroform); EIMS (70 eV) m/z (relative intensity) 309 and 311 (3.5, M⁺)

Example 15 tert-Butyl (R)-4-(7-Amino-4-bromo-5,6,7,8-tetrahydro-1-naphthyl)piperazin-1-carboxylate To an ice-cooled solution of (R)-2-amino-5-bromo-8-(piperazin-1-yl)-1,2,3,4-tetrahydronaphthalene (0.8 g, 2.6 mmol) and triethylamine (0.53 mL, 3.9 mmol) in methylene chloride (50 mL) was added di-tert-butyl dicarbonate (0.56 g, 2.6 mmol) dissolved in methylene chloride (10 mL). After the addition, the reaction was allowed to stir at ambient temperature for 1 h. Water (10 mL) was added and the mixture was cooled on an ice-bath. The water phase was alkalized with a 2 M aqueous solution of sodium hydroxide and the phases were separated. The organic phase was dried ($Na_2SO_4$), filtered and evaporated in vacuo to give a crude product which was purified on a silica gel column using chloroform/methanol/concentrated ammonium hydroxide (95:5:0.5) as the eluent. Yield: 0.41 g (38%) of a viscous colorless oil: $[\alpha]^{21}_D +13°$ (c=1, chloroform); EIMS (70 eV) m/z (relative intensity) 409 and 411 (75, M⁺)

Example 16

(R)-N-[5-Bromo-8-(4-tert-butyloxycarbonylpiperazin-1-yl)-1,2,3,4-tetrahydro-2-naphthyl]-4-morpholinobenzamide 4-Morpholinobenzoic acid (0.50 g, 2.4 mmol; described in: Degutis, J.; Rasteikiene, L.; Degutiene, A. *Zh. Org. Khim*. 1978, 14(10), 2060–2064) was dissolved in thionyl chloride (10 mL). After 2 min, the thionyl chloride was evaporated in vacuo and the residue was treated with toluene and again the solvent was evaporated in vacuo. Crude acid chloride (81 mg, 0.36 mmol) was dissolved in methylene chloride (10 mL) and added dropwise to a solution of tert-butyl (R)-4-(7-amino-4-bromo-5,6,7,8-tetrahydro-1-naphthyl)piperazin-1-carboxylate (140 mg, 0.34 mmol) and triethylamine (71 µL, 0.51 mmol) in methylene chloride (10 mL). After the addition, the reaction was stirred at ambient temperature for 15 min and was then washed with a diluted aqueous solution of sodium hydrogen carbonate and the phases were separated. The organic phase was dried ($Na_2SO_4$), filtered and evaporated in vacuo and the residue was purified on a silica gel column using chloroform/ethanol saturated with $NH_3$ (100:2) as the eluent. Yield: 160 mg (79%) of a viscous colorless oil: $[\alpha]^{21}_D -11°$ (c=1, chloroform); TSPMS m/z (relative intensity) 599 and 601 (35, M⁺+1).

Example 17

(R)-N-[5-Bromo-8-(piperazin-1-yl)-1,2,3,4-tetrahydro-2-naphthyl]-4-morpholinobenzamide To an ice-cooled solution of (R)-N-[5-bromo-8-(4-tert-butyl oxycarbonylpiperazin-1-yl)-1,2,3,4-tetrahydro-2-naphthyl]-4-morpholinobenzazmide (150 mg, 0.26 mmol) in methylene chloride (20 mL) was added trifluoroacetic acid (0.7 mL). The reaction was stirred at ambient temperature for 20 h. The solvent was evaporated in vacuo and the residue was dissolved in water (20 mL), alkalized with a 2 M aqueous solution of sodium hydroxide and extracted with methylene chloride. The phases were separated and the organic phase was dried ($Na_2SO_4$), filtered and evaporated in vacuo. The residue was purified on a silica gel column using chloroform/methanol/concentrated ammonium hydroxide (90:10:1) as the eluent. Yield: 94 mg (72%) of a white crystals: mp 228–229° C.; $[\alpha]^{21}_D -6°$ (c-1, chloroform); EIMS (70 eV) m/z (relative intensity) 498 and 500 (1.5, M⁺)

Example 18

(R)-2-Amino-8-(4-methylpiperazin-1-yl)-1,2,3,4-tetrahydronaphthalene

To a solution of (R)-2-N,N-dibenzylamino-8-(4-methylpiperazin-1-yl)-1,2,3,4-tetrahydronaphthalene (4.0 g, 9.4 mmol) in methanol (250 mL) were added ammonium formate (14 g, 56 mmol) and palladium (10%) on activated carbon (1.4 g). The mixture was refluxed for 3 h and the palladium was then filtered off. The solvent was evaporated in vacuo and the residue was partitioned between methylene chloride and a 2 M ammonium hydroxide solution. The organic phase was separated, dried ($Na_2SO_4$), filtered and evaporated in vacuo to give a crude product which was purified on a silica gel column using chloroform/methanol/concentrated ammonium hydroxide (90:9:0.5) as the eluent. Yield: 1.9 g (83%) as an oil: $[\alpha]^{21}_D -2.7°$ (c 1.0,chloroform); EIMS (70 eV) m/z (relative intensity) 245 (5, M⁺).

Example 19

(R)-2-Amino-5-bromo-8-(4-methylpiperazin-1-yl)-1,2,3,4-tetrahydronaphthalene

The title compound was prepared from (R)-2-amino-8-(4-methylpiperazin-1-yl)-1,2,3,4-tetrahydronaphthalene following the general method of Example 8. Purification on a silica gel column using chloroform/ethanol/concentrated ammonium hydroxide (80:20:2) as the eluent gave 630 mg (89% yield) of a viscous colorless oil: EIMS (70 eV) m/z (relative intensity) 323 and 325 (20, M$^+$)

Example 20

(R)-N-[5-Bromo-8-(4-methylpiperazin-1-yl)-1,2,3,4-tetrahydro-2-naphthyl]-4-morpholinobenzamide The title compound was prepared from (R)-2-amino-5-bromo-8-(4-methylpiperazin-1-yl)-1,2,3,4-tetrahydronaphthalene following the general method of Example 16. Purification on a silica gel column using chloroform/methanol/concentrated ammonium hydroxide (95:5:1) as the eluent gave 100 mg (62% yield) of white crystals: mp 245–246° C. $[\alpha]^{21}_D$ −23° (c=1, chloroform); EIMS (70 eV) m/z (relative intensity) 512 and 514 (1, M$^+$).

Example 21

(R)-2-Amino-8-bromo-5-methoxy-1,2,3,4-tetrahydronaphthalene Hydrochloride (R)-2-Amino-5-methoxy-1,2,3,4-tetrahydronaphthalene hydrochloride (5.0 g, 23 mmol) was dissolved in acetic acid (300 mL) under nitrogen atmosphere. Sodium acetate (5.5 g, 70 mmol) was added and bromine (3.5 g, 23 mmol) was then added in one portion. The mixture was stirred for 5 minutes at room temperature. The solvent was removed in vacuo to give a solid residue which was partitioned between ethyl acetate and NaOH (2 M). The layers were separated and the aqueous phase was extracted twice with ethyl acetate. The organic layers were combined and dried (Na$_2$SO$_4$). The solvent was removed in vacuo to give a brown oily residue. The HCl salt was precipitated from diethyl ether/methylene chloride by the addition of HCl in diethyl ether (3 M): yield 7.7 g (94%). Recrystallization from methanol gave the title compound as needle crystals: mp 264–265° C.; $[\alpha]^{21}_D$+54° (c 1, MeOH); EIMS (70 eV) m/z (relative intensity) 257 (30, M$^+$, $^{81}$Br), 255 (31, M$^+$, $^{79}$Br).

Example 22

(R)-8-Bromo-2-N,N-dibenzylamino-5-methoxy-1,2,3,4-tetrahydronaphthalene (R)-2-Amino-8-bromo-5-methoxy-1,2,3,4-tetrahydronaphthalene hydrochloride (4.5 g, 17.5 mmol), benzyl bromide (6.6 g, 38 mmol), potassium carbonate (9.7 g, 70 mmol) and potassium iodide (100 mg, catalytic amount) were mixed with acetonitrile (250 mL) under nitrogen atmosphere and refluxed for 18 h. The solvent was removed in vacuo and the residue was partitioned between ethyl acetate and ammonia (2 M). The layers were separated and the organic layer was dried (MgSO$_4$). The solvent was removed in vacuo to give a residue which was purified by flash chromatography on silica gel using hexane/methylene chloride 8:2 as the eluent. The title compound was obtained as an oil. Yield 7.5 g (98%): $[\alpha]^{21}_D$+87° (c 1, MeOH); EIMS (70 eV) m/z (relative intensity) 437 (12, M$^+$,$^{81}$Br), 435 (13, M$^+$,$^{79}$Br).

Example 23

(R)-2-N,N-Dibenzylamino-5-methoxy-8-(4-methylpiperazin-1-yl)-1,2,3,4-tetrahydronaphthalene To a solution of (R)-8-bromo-2-N,N-dibenzylamino-5-methoxy-1,2,3,4-tetrahydronaphthalene (19 g, 44 mmol) in dry toluene (500 mL) under an argon atmosphere was added N-methylpiperazine (5.9 mL, 53 mmol), tris (dibenzylideneacetone)dipalladium(0) (0.41 g, 0.44 mmol), (R)-BINAP (0.82 g, 1.3 mmol) and sodium tert-butoxide (0.40 mg, 4.2 mmol). The dark solution was stirred at 85° C. for 23 h and was then cooled, filtered and evaporated in vacuo. Purification on a silica gel column using chloroform/ethanol saturated with NH$_3$ (100:2) as the eluent gave 19 g (97% yield) of a viscous colorless oil: $[\alpha]^{21}_D$+72° (c=1, chloroform); EIMS (70 eV) m/z (relative intensity) 455 (15, M$^+$).

Example 24

(R)-2-Amino-5-methoxy-8-(4-methylpiperazin-1-yl)-1,2,3,4-tetrahydronaphthalene

The title compound was prepared from (R)-2-N,N-dibenzylamino-5-methoxy-8-(4-methylpiperazin-1-yl)-1,2,3,4-tetrahydronaphthalene following the general method of Example 10. Yield: 5.3 g (82%) of a viscous colorless oil: $[\alpha]^{21}_D$+20° (c=1.1, chloroform); EIMS (70 eV) m/z (relative intensity) 275 (53, M$^+$).

Example 25

(R)-N-[5-Methoxy-8-(4-methylpiperazin-1-yl)-1,2,3,4-tetrahydro-2-naphthyl]-4-morpholinobenzamide To a solution of 4-morpholinobenzoic acid (0.92 g, 4.5 mmol; described in: Degutis, J.;Rasteikiene, L.; Degutiene, A. Zh. Org. Khim. 1978, 14(10), 2060–2064) in anhydrous N,N-dimethylformarnmide (75 mL) was added 1,1'-carbonyldiimidazole (0.76 g, 4.8 mmol) and the reaction was heated at 75° C. When the carbon dioxide evolution had ceased (after 45 min), the reaction was cooled to room temperature and a solution of (R)-2-amino-5-methoxy-8-(4-methylpiperazin-1-yl)-1,2,3,4-tetrahydronaphthalene (1.2 g, 4.2 mmol) dissolved in anhydrous N,N-dimethylformamide (20 mL) was added. The reaction was allowed to stir at ambient temperature for 48 h and the solvent was evaporated in vacuo. Purification on a silica gel column using chloroform/methanol/concentrated ammonium hydroxide (180:5:0.5) as the eluent followed by recrystallization from ethyl acetate and a few drops of methanol gave 1.0 g (53% yield) of white crystals: mp 237–238° C. $[\alpha]^{21}_D$−40° (c=1, chloroform); EIMS (70 eV) m/z (relative intensity) 464 (5, M$^+$).

Example 26

(R)-N-[5-Hydroxy-8-(4-methylpiperazin-1-yl)-1,2,3,4-tetrahydro-2-naphthyl]-4-cyanobenzamide The title compound was prepared from (R)-2-amino-5-hydroxy-8-(4-methylpiperazin-1-yl)-1,2,3,4-tetrahydronaphthalene following the general method of Example 11. Purification on a silica gel column using chloroform/methanol/concentrated ammonium hydroxide (95:5:0.5) as the eluent gave 71 mg (45% yield) of light-brown crystals: mp 144° C. (sinters); $[\alpha]^{21}_D$+15° (c=0.25, methanol); EIMS (70 eV) m/z (relative intensity) 390 (12, M$^+$).

Example 27

(R)-N-[5-Methoxy-8-(4-methylpiperazin-1-yl)-1,2,3,4-tetrahydro-2-naphthyl]-4-morpholinocarbonylbenzamide The title compound was prepared from (R)-2-amino-5-methoxy-8-(4-methylpiperazin-1-yl)-1,2,3,4- tetrahydronaphthalene following the general method of Example 16. Purification on a silica gel column using chloroform/methanol/concentrated ammonium hydroxide (96:4:0.3) as the eluent gave after recrystallization from ethyl acetaldiethyl ether 93 mg (52% yield) of white crystals: mp 209–210° C.; $[\alpha]^{21}_D$ –18° (c=1, chloroform); EIMS (70 eV) m/z (relative intensity) 492 (36, M$^+$).

Example 28

(R)-N-[5-Bromo-8-(4-methylpiperazin-1-yl)-1,2,3,4-tetrahydro-2-naphthyl]-4-morpholinocarbonylbenzamide The title compound was prepared from (R)-2-amino-5-bromo-8-(4-methylpiperazin-1-yl)-1,2,3,4-tetrahydronaphthalene following the general method of Example 16. Purification on a silica gel column using chloroform/methanol/concentrated ammonium hydroxide (96:4:0.3) as the eluent gave after recrystallization from ethyl acetate/diethyl ether 110 mg (64% yield) of white crystals: mp 228–230° C.; $[\alpha]^{21}_D$ –10° (c=1, chloroform); EIMS (70 eV) m/z (relative intensity) 540 and 542 (32, M$^+$).

Example 29

Methyl 5-Methoxy-8-nitro-1,2,3,4-tetrahydronaphthalene-2-carboxylate

Methyl 5-methoxy-1,2,3,4-tetrahydronaphthalene-2-carboxylate (1.1 g, 5 mmol; described in: Johnson, D. W.; Mander, L. N. Aust. J. Chem. 1974, 8, 1277–1286) dissolved in acetic anhydride (20 mL), was treated with 70% nitric acid (0.4 mL) at 0° C. for 1 h and the mixture was poured into ice-water and diethyl ether. The organic phase was separated, evaporated in vacuo and the residue triturated with diisopropyl ether to yield 0.27 g (20%) of the title compound as crystals: mp 100–104° C.; EIMS (70 eV) m/z (relative intensity) 265 (35, M$^+$).

Example 30

5-Methoxy-8-nitro-1,2,3,4-tetrahydronaphthalene-2-carboxylic Acid

A mixture of methyl 5-methoxy-8-nitro-1,2,3,4-tetrahydronaphthalene-2-carboxylate (1.9 g, 7.1 mmol) in methanol (20 mL) and 2 M NaOH (10 mL) was refluxed for 1.5 h and the solvent was evaporated in vacuo. The residue was taken up in ethyl acetate and acidified. The organic phase was separated and dried and evaporated in vacuo to afford 1.7 g (95% yield) of crystals: mp (after recrystallization in diisopropyl ether/ethanol) 189–190° C.; EIMS (70 eV) m/z (relative intensity) 251 (30, M$^+$).

Example 31

N-(4-Morpholinophenyl)-5-methoxy-8-nitro-1,2,3,4-tetrahydronaphthalene-2-carboxamide A mixture of 5-methoxy-8-nitro-1,2,3,4-tetrahydronaphthalene-2-carboxylic acid (1.3 g, 5 mmol), toluene (20 mL) and thionyl chloride (1.8 mL, 25 mmol) was heated at 80° C. for 1 h. The solvents were removed in vacuo and the residue, dissolved in methylene chloride (10 mL), was added to a solution of 4-morpholinoaniline (890 mg, 5 mmol) and triethylamine (1.0 g, 10 mmol) in methylene chloride (20 mL) at 0° C. The mixture was stirred at 20° C. for 2 h, water was added and the precipitate was filtered to yield 1.9 g (90%) of the title product as crystals: mp 251–253° C.; EIMS (70 eV) m/z (relative intensity) 411 (100, M$^+$).

Example 32

N-(4-Morpholinophenyl)-8-amino-5-methoxy-1,2,3,4-tetrahydronaphthalene-2-carboxamide A solution of N-(4-morpholinophenyl)-5-methoxy-8-nitro-1,2,3,4-tetrahydronaphthalene-2-carboxamide (2.05 g, 5 mmol) and sodium dithionite (3.5 g, 20 mmol) in N,N-dimethylformamide (20 mL) and water (2 mL) was heated at 90° C. for 7 h. After cooling, the reaction mixture was partitioned between water and ethyl acetate, the phases were separated and the organic phase was washed, twice, with water and evaporated in vacuo. The residue was triturated with diisopropyl ether/ethyl acetate affording 1.4 g (72% yield) of the title product as crystals: mp 219–222° C.; EIMS (70 eV) m/z (relative intensity) 381 (70, M$^+$).

Example 33

N-(4-Morpholinophenyl)-8-(4-methylpiperazinyl)-5-methoxy-1,2,3,4-tetrahydronaphthalene-2-carboxamide A solution of N-(4-morpholinophenyl)-8-amino-5-methoxy-1,2,3,4-tetrahydronaphthalene-2-carboxamide (1.4 g, 3.5 mmol), bis(2-chloroethyl)-methylamine hydrochloride (960 mg, 5 mmol) and sodium hydrogen carbonate (420 mg, 5 mmol) in n-butanol (30 mL) was heated at 90° C. for 5 h. After cooling, 2 M ammonium hydroxide (30 mL) was added and the mixture heated at 50° C. for 1 h. The phases were separated, evaporated in vacuo and purified by flash chromatography on a silica gel column with chloroform/ethanol/conc. ammonium hydroxide 90/10/0.3 as eluent. Yield: 320 mg (20%) of the title compound: mp 230–232° C.; EIMS (70 eV) m/z (relative intensity) 464 (75, M$^+$).

Example 34

N-(4-Morpholinocarbonylphenyl)-5-methoxy-8-nitro-1,2,3,4-tetrahydronaphthalene-2-carboxamide A mixture of 5-methoxy-8-nitro-1,2,3,4-tetrahydronaphthalene-2-carboxylic acid (1.0 g, 4 mmol), toluene (20 mL), N,N-dimethylformamide (10 drops) and thionyl chloride (1.5 mL, 20 mmol) was heated at 60° C. for 1 h. The solvents were removed in vacuo and the residue, dissolved in methylene chloride (20 mL), was added to a solution of 4-aminobenzoylmorpholine (820 mg, 4 mmol, described in: Devlin J.P. J. Chem. Soc. Perkin Trans I, 1975, 830–841) and triethylamine (800 mg, 8 mmol) in methylene chloride (30 mL) at 5° C. After stirring at 20° C. for 2 h, water was added and the organic phase was separated, dried and the solvent removed in vacuo. The oily residue was crystallized from diisopropyl ether/ethyl acetate affording 1.2 g (73% yield) of the title compound as crystals: mp 186–189° C.; EIMS (70 eV) m/z (relative intensity) 439 (20, M$^+$).

Example 35

N-(Morpholinocarbonylphenyl)-8-amino-5-methoxy-1,2,3,4-tetrahydronaphthalene-2-carboxamide A solution of N-(4-morpholinocarbonylphenyl)-5-methoxy-8-nitro-1,2,3,4-tetrahydronaphthalene-2-carboxamide (1.3 g, 2.8 mmol) and sodium dithionite (2.0 g, 11 mmol in N,N-dimethylformamide (20 mL) and water (2.5 mL) was heated at 85° C. for 3 h. After cooling, the reaction mixture was partitioned between water and ethyl acetate, the phases were separated and the organic phase was washed, twice, with water and evaporated in Vacuo. The residue was treated with diisopropyl ether affording 310 mg (30% yield) of the title product as crystals: EIMS (70eV) m/z (relative intensity) 409 (100, M+).

Example 36

N-(Morpholinocarbonylphenyl)-8-(4-methylpiperazin-1-yl)-5-methoxy-1,2,3,4-tetrahydronaphthalene-2-carboxamide A solution of N-(morpholinocarbonylphenyl)-8-amino-5-methoxy-1,2,3,4-tetrahydronaphthalene-2-carboxamide (280 mg, 0.69 mmol), bis(2-chloroethyl)methyl amine hydrochloride (190 mg, 1.0 mmol) and sodium hydrogen carbonate (84 mg, 1.0 mmol) in n-butanol (20 mL) was heated at 90° C. for 5 h. After cooling, 2 M ammonium hydroxide (10 mL) was added and the mixture was heated at 50° C. for 1 h. The organic phase was evaporated in vacuo and the residue was purified by flash chromatography on a silica gel column using chloroform/ethanol/conc. ammonium hydroxide (90:10:0.5) as eluent to yield 60 mg (18%) of the title compound: EIMS (70 eV) m/z (relative intensity) 492 (50, M$^+$).

Example 37

(R)-2-Amino-5-methoxy-8-(1-methylpiperidin-4-yl)-1,2,3,4-tetrahydronaphthalene (R)-8-Bromo-2-N,N-dibenzylamino-5-methoxy-1,2,3,4-tetrahydronaphthalene (6.8 g, 16 mmol) was dissolved in anhydrous tetrahydrofuran (100 mL) under nitrogen atmosphere. The solution was cooled to −78° C. and n-butyllithium (11.7 mL, 1.6 M, 19 mmol) was added dropwise during 3 minutes. The mixture was stirred for 5 min and N-methyl-4-piperidone (5.4 g, 48 mmol) was added during 3 min. The cooling bath was removed and the temperature was allowed to rise to 0° C. before the reaction was quenched by the addition of water. The layers were separated and the organic layer was dried (MgSO$_4$). The solvent was removed in vacuo to give a residue which was purified by crystallization (ethyl acetate/hexane). Yield 5.8 g (77%): EIMS (70 eV) m/z (relative intensity) 470 (2, M$^+$). The crystals (4.6 g, 9.8 mmol) were dissolved in toluene and p-toluenesulfonic acid (2.8 g, 15 mmol) was added and the reaction was stirred at reflux for 8 h under nitrogen with azeotropic removal of water in a Dean-Stark trap. The cooled reaction mixture was washed with a 2 M aqueous solution of sodium hydroxide and the phases were separated, dried (MgSO$_4$), filtered and evaporated in vacuo to give a viscous oil: EIMS (70 eV) m/z (relative intensity) 452 (1, M$^+$). The oil (0.6 g, 1.3 mmol) was dissolved in a solution of methanol (30 mL) and water (15 mL) and ammonium formate (1.7 g, 26 mmol) and palladium (0.3 g: 10% on activated carbon) was added. The mixture was refluxed for 45 min and the palladium was filtered off. The solvent was evaporated in vacuo and the residue was partitioned between ethyl acetate and a 2 M solution of ammonium hydroxide. The organic phase was separated, dried (Na$_2$SO$_4$), filtered and evaporated in vacuo to give 300 mg (95% yield) of the title compound.

Example 38

(R)-N-[5-Methoxy-8-(1-methylpiperidin-4-yl)-1,2,3,4-tetrahydro-2-naphthyl]-4-morpholinobenzamide The title compound was prepared from (R)-2-amino-5-methoxy-8-(1-methylpiperidin-4-yl)-1,2,3,4-tetrahydronaphthalene following the general method of Example 16. Purification on a silica gel column using methylene chloride/ethanol/concentrated ammonium hydroxide (10:1:0.5) as the eluent gave 135 mg (53% yield) of crystals: mp 237–242° C. (decomp.); [α]$^{21}_D$ −2° (c=0.5, chloroform); EIMS (70 eV) m/z (relative intensity) 463 (15, M$^+$).

Example 39

Chromatographic Preparation of the Enantiomers of N-(4-Morpholinophenyl)-8-(4-methylpiperazinyl)-5-methoxy-1,2,3,4-tetrahydronaphthalene-2-carboxamide N-(4-Morpholinophenyl)-8-(4-methylpiperazinyl)-5-methoxy-1,2,3,4-tetrahydronaphthalene-2-carboxamide (5 mg) was dissolved in 4 ml of eluent consisting of acetonitrile and pH 3.0 phosphate buffer, μ=0.1 (62.5: 37.5, v/v). This solution was purified on a Nucleosil 7 C$_{18}$ column (25×250 mm) with the above mobile phase to remove late eluting impurities. The collected fractions of the main component were concentrated under reduced pressure at 35–39° C. The residue was dissolved in 30 ml of the eluent composed of 10 mM ammonium acetate, diethylamine and acetic acid (4000+2+2, v/v/v, pH 5.26) and the chiral semi-preparation of the enantiomers of N-(4-morpholinophenyl)-8-(4-methylpiperazinyl)-5-methoxy-1,2,3,4-tetrahydronaphthalene-2-carboxamide was carried out on a Chiral AGP semi-prepative column (10×150 mm) using a guard column of the same stationary phase. 2.0 ml/min of flow rate was used and detection was monitored at 260 nm. Fractions of both enantiomers were separately collected and concentrated to a volume of about 5 ml under reduced pressure at 35–39° C. The concentrated fractions were adjusted to pH 10–11 with 5 M NaOH and extracted with chloroform. The two organic phases were washed with water and dried with anhydrous magnesium sulfate. After being filtered through glasswool, the organic filtrates were evaporated in vacuo affording the two enantiomers as two slightly yellow solids.

Example 40

(R)-2-N,N-Dibenzylamino-5-(1-hydroxyethyl)-8-(4-methylpiperazin-1-yl)-1,2,3,4-tetrahydronaphthalene (R)-5-Bromo-2-N,N-dibenzylamino-8-(4-methylpiperazin-1-yl)-1,2,3,4-tetrahydronaphthalene (1.4 g, 2.8 mmol) was dissolved in freshly distilled tetrahydrofuran (100 mL), flushed with argon and cooled to −78° C. To the solution was added tert-butyl lithium (2.6 mL, 1.4 M in pentane, 3.7 mmol) and the reddish solution was stirred at ambient temperature for 10 min. Acetaldehyde (320 μL, 5.7 mmol) was added and the reaction mixture was stirred at −78° C. for 10 min, at 0° C. for 2 h and at room temperature for 10 min. The reaction was quenched with water and the solvent was evaporated in vacuo. The residue was partitioned between diethyl ether (100 mL) and 2 M NH$_3$ (20 mL) and the aqueous phase was extracted with diethyl ether (20 mL). The combined organic layers were washed with brine (20 mL) and dried (MgSO$_4$). The solvent was evaporated giving 2.0 g of a crude product. Purification by column chromatography on silica gel using chloroform/methanol/conc. NH$_3$ (95:5:0.5) as the eluent gave 910 mg (68% yield) of the title compound as a yellowish foam: ESIm/z (relative intensity) 470 (100, M+1).

Example 41

(R)-2-Amino-5-ethyl-8-(4-methylpiperazin-1-yl)-1,2,3,4-tetrahydronaphthalene (R)-2-N,N-Dibenzylamino-5(1-hydroxyethyl)-8-(4-methylpiperazin-1-yl)-1,2,3,4-tetrahydronaphthalene (1.6 g, 3.4 mmol) was dissolved in acetic acid (80 mL) and stirred at 100° C. for 2 h. The solvent was evaporated in vacuo and the residue was dissolved in methanol (50 mL). Palladium (10%) on charocoal (600 mg) was added and the solution was flushed with nitrogen. To the solution was added ammonium formate (1.7 g, 28 mmol) and the reaction mixture was stirred at 65° C. for 2 h. The catalyst was filtered off and the solvent was evaporated in vacuo giving 1.3 g of a crude product. The residue was partitioned between methylene chloride (120 mL) and 2 M $NH_3$ (30 mL). The organic phase was washed with brine (20 mL) and dried ($MgSO_4$). The solvent was evaporated in vacuo giving 740 mg (79% yield) of the title compound as a white semi-crystalline solid: EIMS (70eV) m/z (relative intensity) 273 (24, $M_+$)

Example 42

(R)-N-[5-Ethyl-8-(4-methylpiperazin-1-yl)-1,2,3,4-tetrahydro-2-naphthyl]-4-morpholinobenzamide 4-Morpholinobenzoic acid (64 mg, 0.31 mmol) was dissolved in dry N,N-dimethylformamide (1 mL) and 1,1'-carbonyldiimidazole (52 mg, 0.32 mmol) was added. The reaction mixture was stirred at 75° C. for 1 h and cooled to room temperature. A solution of (R)-2-amino-5-ethyl-8-(4-metylpiperazin-1-yl)-1,2,3,4-tetrahydronaphthalene (80 mg, 0.29 mmol) in dry N,N-dimethylformamide (3 mL) was added and the reaction mixture was stirred at room temperature for 14 h. The solvent was evaporated and the residue was dried in vacuo. The crude product was purified by preparative TLC on silica using chloroform/methanol/conc. $NH_3$ (95:5:0.5) as the eluent which gave 85 mg (59% yield) of the title compound as a white solid: mp 234° C. (dec); EIMS (70 eV) m/z (relative intensity) 462 (27, $M^+$); $[\alpha]^{21}_D$–48° (c 0.09, chloroform).

Example 43

(R)-N-[5-Ethyl-8-(4-methylpiperazin-1-yl)-1,2,3,4-tetrahydro-2-naphthyl]-(4-morpholinocarbonyl)benzamide 4-Morpholinocarbonylbenzoic acid (180 mg, 0.77 mmol; described in: *J. Med. Chem.* 1994, 37(26), 4538–4554) and 1,1'-carbonyldiimidazole (130 mg, 0.80 mmol) were dissolved in dry N,N-dimethylformamide (3 mL) and stirred at 75° C. for 2 h. After cooling to room temperature, a solution of (R)-2-amino-5-ethyl-8-(4-methylpiperazin-1-yl)-1,2,3,4-tetrahydronaphthalene (200 mg, 0.73 mmol) in dry N,N-dimethylformamide was added and the reaction mixture was stirred for 60 h. The solvent was evaporated in vacuo and the residue was partitioned between methylene chloride (60 mL) and 2 M $NH_3$ (5 mL). The organic phase was washed with brine (10 mL) and dried ($Na_2SO_4$). Evaporation of the solvent in vacuo gave 360 mg of a crude product. Purification by column chromatography on silica using chloroform/methanol/conc. $NH_3$ (95:5:0.5) as the eluent afforded 240 mg (65% yield) of the title compound as a white solid: mp 213–214° C.; EIMS (70 eV) m/z (relative intensity) 490 (27, $M^+$); $[\alpha]^{21}_D$–28° (c 0.15, chloroform).

Example 44

(R)-2-N,N-Dibenzylamino-5-difluoromethoxy-8-(4-methylpiperazin-1-yl)1,2,3,4-tetrahydronaphthalene To a solution of (R)-2-N,N-dibenzylamino-5-hydroxy-8-(4-methylpiperazin-1,2,3,4-tetrahydronaphthalene (1 g, 2.3 mmol) in 2-propanol (75 mL) was added sodium hydroxide (2.8 g, 69 mmol) with stirring, until most of it was dissolved (1.5 h) and the reaction mixture was heated to 65° C. Chlorodifluoromethane was bubbled into the reaction with vigorous stirring for 6 min and the reaction mixture was allowed to cool to room temperature. The reaction mixture was filtered and the solvent was evaporated in vacuo and the residue was partitioned between diethyl ether and water. The phases were separated and the organic phase was dried ($Na_2SO_4$), filtered and evaporated in vacuo. Purification on a silica gel column using chloroform/ethanol saturated with $NH_3$ (100:1) as the eluent gave 230 mg (21% yield) of a viscous colorless oil: $[\alpha]^{21}_D$+119° (c 0.5 chloroform) EIMS (70 eV) m/z (relative intensity) 492 (1, M+).

Example 45

(R)-2-Amino-5-difluoromethoxy-8-(4-methylpiperazin-1-yl)-1,2,3,4-tetrahydronaphthalene The title compound was prepared from (R)-2-N,N-dibenzylamino-5-difluoromethoxy-8-(4-methylpiperazin-1-yl)-1,2,3,4-tetrahydronaphthalene following the general method of Example 10. Yield: 67 mg (42%) of a viscous colorless oil: EIMS (70 eV) m/z (relative intensity) 311 (28, $M^+$).

Example 46

(R)-N-[5-Difluoromethoxy-8-(4-methylpiperazin-1-yl)-1,2,3,4-tetrahydro-2-naphthyl]-4-morpholinobenzamide The title compound was prepared from (R)-2-amino-5-difluoromethoxy-8-(4-methylpiperazin-1-yl)-1,2,3,4-tetrahydronaphthalene following the general method of Example 25. Purification on a silica gel column using chloroform/ethanol saturated with $NH_3$ (100:3) as the eluent gave 26 mg (24% yield) of white crystals: mp 222–223° C.; $[\alpha]^{21}_D$–51° (c=1, chloroform); EIMS (70 eV) m/z (relative intensity) 500 (0.9, $M^+$).

Example 47

(R)-N-[8-(4-Methylpiperazin-1-yl)-1,2,3,4-tetrahydro-2-naphthyl]-4-trifluoromethylbenzamide To an ice-cooled solution of (R)-2-amino-8-(4-methylpiperazin-1-yl)-1,2,3,4-tetrahydronaphthalene (10 mg, 0.44 mmol) and triethylamine (91 µL, 0.66 mmol) in methylene chloride (20 mL) was 4-(trifluoromethyl)benzoyl chloride (96 mg, 0.46 mmol) in methylene chloride (5 mL) added dropwise. After the addition the reaction was allowed to stir at ambient temperature for 15 min and was then washed with diluted aqueous sodium hydrogen carbonate. The phases were separated and the organic phase was dried ($Na_2SO_4$), filtered and evaporated in vacuo to give a crude product which was purified on a silica gel column using chloroform/ethanol saturated with $NH_3$ (100:2) as the eluent. Yield: 150 mg (81%) of the title compound as white crystals: mp 203–204° C.; $[\alpha]^{21}_D$–20° (c 1.0, chloroform); EIMS (70 eV) m/z (relative intensity) 417 (10, $M^+$).

Example 48

(R)-N-[5-Bromo-8-(4-methylpiperazin-1-yl)-1,2,3,4-tetrahydro-2-naphthyl]-4-trifluoromethylbenzamide (R)-N-[8-(4-methylpiperazin-1-yl)-1,2,3,4-tetrahydro-2-naphthyl]-4-trifluoromethylbenzamide (80 mg, 0.19 mmol)

and sodium acetate (200 mg) were dissolved in acetic acid (3 mL) and the mixture was stirred at room temperature. Bromine (34 mg, 0.21 mmol) was added dropwise to the reaction mixture and the mixture was stirred for 2 h at ambient temperature. A 2 M sodium hydroxide solution (100 mL) was added and the mixture was extracted with diethyl ether (2×50 mL). The combined organic phases were dried over anhydrous sodium sulfate, filtered and concentrated in vacuo. Purification on a silica gel column using methylene chloride/ethanol saturated with $NH_3$ (94:6) as the eluent gave 80 mg (85% yield) of the title compound as a white solid: mp 229–230° C.; $[\alpha]^{21}_D$ -5.4° (c=1, chloroform); EIMS (70 eV) m/z (relative intensity) 495 and 497 (3, M$^+$).

Example 49

(R)-2-N,N-Dibenzylamino-5-methoxymethyl-8-(4-methylpiperazin-1-yl)-1,2,3,4-tetrahydronaphthalene (R)-5-Bromo-2-N,N-dibenzylamino-8-(4-methylpiperazin-1-yl)-1,2,3,4-tetrahydronaphthalene (400 mg, 0.79 mmol) was dissolved in freshly distilled tetrahydrofuran (40 mL), flushed with argon and cooled to −78° C. To the solution was added tert-butyl lithium (740 μL, 1.4 M in pentane, 1.0 mmol). The reddish solution was stirred at ambient temperature for 10 min. Bromomethyl methyl ether (65 μL, 0.79 mmol) was added and the reaction mixture was stirred at −78° C. for 1 h, at 0° C. for 1 h and at room temperature for 10 min. The reaction was quenched with water and the solvent was evaporated. The residue was partitioned between diethyl ether (70 mL) and 2 M $NH_3$ (15 mL) and the aqueous layer was extracted with diethyl ether (20 mL). The combined organic layers were washed with brine (15 mL) and dried (MgSO$_4$). The solvent was evaporated giving 330 mg of a crude product. Purification by column chromatography on two silica gel columns using chloroform/methanol/conc. $NH_3$ (250:5:0.5) and (180:5:0.5) as the eluents afforded 160 mg (43% yield) of the title compound as a yellowish oil: EIMS (70 eV) m/z (relative intensity) 469 (4, M$^+$); $[\alpha]^{21}_D$ +33° (c 0.13, chloroform).

Example 50

(R)-2-Amino-5-methoxymethyl-8-(4-methylpiperazin-1-yl)-1,2,3,4-tetrahydronaphthalene (R)-2-N,N-Dibenzylamino-5-methoxymetyl-8-(4-methylpiperazin-1-yl)-1,2,3,4-tetrahydronaphthalene (160 mg, 0.34 mmol) was dissolved in methanol and the solution was flushed with nitrogen. Palladium (10%) on charcoal (80 mg) and ammonium formate (170 mg, 2.7 mmol) were added. The reaction was stirred at 65° C. for 2 h. The catalyst was filtered off and the solvent was evaporated in vacuo giving 97 mg of a crude product. Purification by preparative TLC using chloroform/ethanol saturated with ammonia (8:1) as the eluent gave 72 mg (73% yield) of the title compound as a semi-solid material: EIMS (70 eV) m/z (relative intensity) 289 (40, M$^+$); $[\alpha]^D_{21}$ −10° (c 0.06, chloroform).

Example 51

(R)-N-[5-Methoxymethyl-8-(4-methylpiperazin-1-yl)-1,2,3,4-tetrahydro-2-naphthyl]-4-morpholinobenzamide 4-Morpholinobenzoic acid (54 mg, 0.26 mmol) was dissolved in dry N,N-dimethylformamide (1 mL) and 1,1'-carbonyldiimidazole was added. The reaction mixture was stirred at 75° C. for 1.5 h and cooled to room temperature. A solution of (R)-2-amino-5-methoxymethyl-8-(4-methylpiperazin-1-yl)-1,2,3,4-tetrahydronaphthalene (72 mg, 0.25 mmol) in dry N,N-dimethylformamide (3 mL) was added. The reaction mixture was stirred at room temperature for 15 h. The solvent was evaporated giving 160 mg of a crude product. Purification by preparative TLC using chloroform/methanol/conc. $NH_3$ (95:5:0.5) as the eluent afforded 95 mg (80% yield) of the title compound as a white solid: mp 200° C. (dec); EIMS (70 eV) m/z (relative intensity) 478 (7, M$^+$); $[\alpha]^{21}$D 46° (c 0.12, chloroform).

Example 52

(R)-2-N,N-Dibenzylamino-5-hydroxymethyl-8-(4-methylpiperazin-1-yl)-1,2,3,4-tetrahydronaphthalene (R)-5-Bromo-2-N,N-dibenzylamino-8-(4-methylpiperazin-1-yl)-1,2,3,4-tetrahydrqnaphthalene (800 mg, 1.6 mmol) was dissolved in freshly distilled tetrahydrofuran (80 mL), flushed with argon and cooled to −78° C. To the solution was added tert-butyl lithium (1.5 mL, 1.4 M in pentane, 2.1 mmol) and the reaction mixture was stirred at ambient temperature for 10 min. Methyl chloroformate (250 μL, 3.2 mmol) was added and the reaction mixture was stirred at −78° C. for 50 min and at 0° C. for 1 h. The reaction was quenched with water and the solvent was evaporated in vacuo. The residue was partitioned between diethyl ether (90 mL) and 2 M $NH_3$ (15 mL). The organic layer was washed with brine (10 mL) and dried (MgSO$_4$). The solvent was evaporated in vacuo giving 770 mg of a crude product. Purification by column chromatography on silica gel using chloroform/methanol/conc. $NH_3$ (250:5:0.5) as the eluent afforded 610 mg of (R)-5-carboxymethyl-2-N,N-dibenzylamino-8-(4-methylpiperazin-1-yl)-1,2,3,4-tetrahydronaphthalene (containing 13% of the corresponding 5-hydrogen analogue) as a yellowish oil: EIMS (70 eV) m/z (relative intensity) 483 (1, M$^+$). The methyl ester (610 mg, 1.1 mmol) was dissolved in freshly distilled tetrahydrofuran (35mL) and lithium aluminum hydride (120 mg, 3.1 mmol) was added. The reaction mixture was stirred at 45° C. for 2 h followed by cooling to room temperature. The reaction was quenched with water (120 μL), 15% NaOH (120 μL) and water (240 μL) followed by stirring the slurry at s room temperature for 2.5 h. The precipitate was filtered off and the solvent was evaporated in vacuo giving 730 mg of a crude product. Purification by column chromatography on a silica gel column using chloroform/methanol/conc. $NH_3$ (95:5:0.5) as the eluent gave 360 mg (50% yield) of the title compound as a white foam: EIMS (70 eV) m/z (relative intensity) 455 (1, M$^+$); $[\alpha]^{21}_D$ +44° (c 0.12, chloroform).

Example 53

(R)-2-Amino-5-methyl-8-(4-methylpiperazin-1-yl)-1,2,3,4-tetrahydronaphthalene (R)-2-N,N-Dibenzylamino-5-hydroxymethyl-8-(4-methylpiperazin-1-yl)-1,2,3,4-tetrahydronaphthalene (360 mg, 0.78 mmol) was dissolved in methanol (35 mL), palladium (10%) on charcoal (170 mg) was added and the solution was flushed with nitrogen. To the solution was added ammonium formate (390 mg, 6.2 mmol) and the reaction mixture was stirred at 65° C. for 13 h. The catalyst was filtered off and the solvent was evaporated in vacuo giving 220 mg of a residue. The crude hydroxymethyl compound was dissolved in acetic acid (25 mL), palladium (10%) on charcoal (60 mg) was added and the solution was flushed with hydrogen. The reaction mixture was hydrogenated at room temperature and at atmospheric pressure for 4 h. The catalyst was filtered off and more palladium (10%) on charcoal (160 mg) was added followed by hydrogenation at room temperature and at atmospheric pressure for 24 h. The catalyst was filtered off and the solvent was evaporated in vacuo. The residue was partitioned between diethyl ether (70 mL) and conc. $NH_3$ and the organic phase was washed with brine (5 mL). The organic layer was dried ($MgSO_4$) and the solvent was evaporated in vacuo to give 120 mg (61% yield) of the title compound as a white semi-crystalline solid: EIMS m/z (relative intensity) 259 (20, $M^+$); $[\alpha]^{21}_D -1°$ (c 0.09, chloroform).

Example 54

(R)-N-[5-Methyl-8-(4-methylpiperazin-1-yl)-1,2,3,4-tetrahydro-2-naphthyl]-4-morpholinobenzamide 4-Morpholinobenzoic acid (92 mg, 0.44 mmol) was dissolved in dry N,N-dimethylformamide (2 mL) and flushed with nitrogen. To the solution was added 1,1'-carbonyldiimidazole (76 mg, 0.47 mmol) and the reaction mixture was stirred at 75° C. for 1.5 h. The solution was cooled to room temperature and (R)-2-amino-5-methyl-8-(4-methylpiperazin-1-yl)-1,2,3,4-tetrahydronaphthalene (110 mg, 0.42 mmol), dissolved in dry N,N-dimethylformamide (2 mL) was added. The solution was stirred at room temperature for 30 h. The solvent was evaporated in vacuo giving 290 mg of a crude product. Purification by preparative TLC on silica gel using chloroform/methanol/conc. $NH_3$ (95:5:0.5) as the eluent afforded 145 mg (73% yield) of the title compound as a white solid: mp >231° C. (dec); EIMS (70 eV) m/z (relative intensity) 448 (3, $M^+$); $[\alpha]^{21}_D -60°$ (c 0.15, chloroform).

Example 55

(S)-2-Amino-8-bromo-5-methoxy-1,2,3,4-tetrahydronaphthalene

The title compound was synthesized according to the procedure of Example 21 using the (S)-form: $[\alpha]^{2}_D -62°$ (c 1.0, chloroform); EIMS (70 eV) m/z (relative intensity) 257 (17, $M^+$, $^{81}Br$), 255 (20, $M^+$, $^{79}Br$).

Example 56

(S)-8-Bromo-2-N,N-dibenzylamino-5-methoxy-1,2,3,4-tetrahydronaphthalene

The title compound was synthesized according to the procedure of Example 22 using the (S)-form: EIMS (70 eV) m/z (relative intensity) 437 (38, $M^+$, $^{81}Br$), 435 (41, $M^+$, $^{79}Br$).

Example 57

(S)-2-N,N-Dibenzylamino-5-methoxy-8-(4-methylpiperazin-1-yl)-1,2,3,4-tetrahydronaphthalene The title compound was synthesized according to the procedure of Example 23 using the (S)-form: EIMS (70 eV) m/z (relative intensity) 455 (10, $M^+$).

Example 58

(S)-2-Amino-5-methoxy-8-(4-methylpiperazin-1-yl)-1,2,3,4-tetrahydronaphthalene

The title compound was synthesized according to the procedure of Example 24 using the (S)-form: EIMS (70 eV) m/z (relative intensity) 275 (55, $M^+$).

Example 59

(S)-N-[5-Methoxy-8-(4-methylpiperazin-1-yl)-1,2,3,4-tetrahydro-2-naphthyl]-4-morpholinobenzamide The title compound was synthesized according to the procedure of Example 25 using the (S)-form: mp 229–232° C.; $[\alpha]^{21}D+48°$ (c 1.0, chloroform); EIMS (70 eV) m/z (relative intensity) 465 (92, $M^{+1}$).

Example 60

(R)-N-[5-Hydroxy-8-(4-methylpiperazin-1-yl)-1,2,3,4-tetrahydro-2-naphthyl]-4-morpholinobenzamide The title compound was synthesized according to the procedure of Example 25 using the product from Example 10: mp 84–88° C.; $[\alpha]^{21}_D -46°$ (c 1.0, chloroform); EIMS (70 eV) m/z (relative intensity) 450 (32, $M^+$).

Example 61

(R)-2-N,N-Dibenzylamino-8-(4-benzylpiperazin-1-yl)-1,2,3,4-tetrahydronaphthalene A solution of (R)-2-N,N-dibenzylamino-8-bromo-1,2,3,4-tetrahydronaphthalene (58 g, 0.14 mol), N-benzylpiperazine (31 g, 0.18 mol), R-BINAP (6.7 g, 11 mmol), tris(dibenzylideneacetone)dipalladium(0) (4.4 g, 4.8 mmol) and sodium tert-butoxide (19 g, 0.2 mol) was heated under argon at 100° C. for 17 h. The mixture was cooled to ambient temperature and filtered through a pad of celite. The solvent was removed and the crude residue was purified on a silica gel column using heptane/ethyl acetate, (4:1), as the eluent to give 62 g (86% yield) of the title compound as a light-brown oil. $[\alpha]_{20}^D =+63°$ (c 1, $CHCl_3$); EINS (70 eV) m/z (relative intensity) 501 (1, $M^+$).

Example 62

(R)-2-N,N-Dibenzylamino-5-bromo-8-(4-benzylpiperazin-1-yl)-1,2,3,4-tetrahydronaphthalene To a solution of (R)-2-N,N-dibenzylamino-8-(4-benzylpiperazin-1-yl)-1,2,3,4-tetrahydronaphthalene (61 g, 0.12 mol) and sodium acetate (148 g, 1.8 mol) in acetic acid (2 L) was bromine (24 g, 0.15 mol) added under stirring. The mixture was stirred for 5 min at room temperature and the solution was evaporate in vacuo. The remains were partitioned between diethyl ether (1.5 L) and water (1 L). The organic phase was collected and extracted with aqueous sodium hydroxide (5 M), washed with brine, dried ($Na_2SO_4$), filtered and evaporated in vacuo to give 70 g of a brown oil. The oil was purified on a silica gel column using heptane/ethyl acetate (5:1) as the eluent to give 41 g (58% yield) of the title compound as an oil. $[\alpha]_{20}^D =+19°$ (c 1, $CHCl_3$); EIMS (70 eV) m/z (relative intensity) 579 and 581 (0.2, $M^+$).

Example 63

(R)-2-N,N-Dibenzylamino-5-methyl-8-(4-benzylpiperazin-1-yl)-1,2,3,4-tetrahydronaphthalene A solution of (R)-2-N,N-dibenzylamino-5-bromo-8-(4-benzylpiperazin-1-yl)-1,2,3,4-tetrahydronaphthalene (35 g, 59 mmol) in anhydrous tetrahydrofuran (650 mL) under argon was cooled to −70° C. followed by the dropwise addition of n-butyllithium (36 mL, 89 mmol; 2.5 M in hexane) during 1 h. The solution was stirred at −70° C. for 2 h and iodomethane (9.3 g, 65 mmol), dissolved in anhydrous tetrahydrofuran (25 mL), was slowly added. The solution was kept at −70° C. for 1 h and then at 0° C. for an additional hour, and then quenched by the addition of 2-propanol (8 mL). The solvents were evaporated, and the remains were partitioned between methylene chloride (700 mL) and water (350 mL). The organic layer was collected, and the water phase was extracted with methylene chloride (200 mL). The combined organic phase was dried ($Na_2SO_4$), filtered and evaporated to give 31 g of a brown oil. The oil was purified on a silica gel column using heptane/diethyl ether (5:1) as the eluent to give 20 g (64% yield) of the title compound as an oil. EIMS (70 eV) m/z (relative intensity) 515 (2, $M^+$).

Example 64

(R)-2-Amino-5-methyl-8-(piperazin-1-yl)-1,2,3,4-tetrahydronaphthalene

A mixture of (R)-2-N,N-dibenzylamino-5-methyl-8-(4-benzylpiperazin-1-yl)-1,2,3,4-tetrahydronaphthalene (20 g, 38 mmol), ammonium forniate (57 g, 0.98 mol) and 10% palladium on charcoal (5.6 g) was refluxed in methanol (2 L) for 3 h. The mixture was cooled to room temperature and filtered through a pad of celite. The solution was evaporated in vacuo and the remains were partitioned between methylene chloride (750 mL) and aqueous ammonia (2 M, 250mL). The organic phase was collected and the aqueous phase was re-extracted with methylene chloride (250 mL). The combined organic phases were dried ($Na_2SO_4$), filtered and evaporated in vacuo to give 8.8 g (95% yield) of the title compound as an oil. The oil was triturated in diethyl ether to give light brown crystals: mp 204–205° C.; EIMS (70 eV) m/z (relative intensity) 245 (31, $M^+$).

Example 65 tert-Butyl (R)-4-(4-Methyl-7-amino-5,6,7,8-tetrahydro-1-naphthyl)piperazin-1-carboxylate A solution of (R)-2-amino-5-methyl-8-(piperazin-1-yl)-1,2,3,4-tetrahydronaphthalene (8.3 g, 34 mmol) and triethylamine (4.0 g, 40 mmol) in methylene chloride (2 L) was cooled to 2° C. and di-tert-butyl dicarbonate (7.4 g, 34 mmol) in methylene chloride (250 mL) was added dropwise under 30 min. The mixture was stirred at room temperature for 1 h followed by the addition of an aqueous solution of sodium hydrogen carbonate (500 mL). The phases were separated and the organic phase was dried ($Na_2SO_4$), filtered and evaporated in vacuo. The crude product was purified on a silica gel column using methylene chloride/methanol/$NH_3$ (aq) (10:0.6:0.06) as the eluent to give 3.7 g (32% yield) of the title compound as an oil which solidified after trituration in diethyl ether. EIMS (70 eV) m/z (relative intensity) 345 (37, $M^+$).

Example 66

(R)-N-[5-Methyl-8-(4-tert-butyloxycarbonylpiperazin-1-yl)-1,2,3,4-tetrahydro-2-naphthyl]-4-morfolinobenzamide To a solution of 4-morfolinobenzoic acid (2.5 g, 12 mmol; described in: Degutis, J.; Rasteikiene, L.; Degutiene, A. *Zh. Org. Khim.* 1978, 14(10), 2060–2064) in anhydrous N,N-dimethylformamide (120 mL) was 1,1'-carbonyldiimidazole (2.1 g, 13 mmol) added portionwise under argon atmosphere. The solution was heated to 75° C. for 30 min and was then cooled to room temperature. tert-Butyl (R)4-(4-methyl-7-amino-5,6,7,8-tetrahydro-1-naphthyl)piperazin-1-carboxylate (3.7 g, 11 mmol) in anhydrous N,N-dimethylformarnide (60 mL) was added dropwise to the solution and the mixture was stirred for 24 h. The solvent was evaporated in vacuo and the crude residue was purified on a silica gel column using heptane/ethyl acetate (3:2) as the eluent to give 4.2 g (74% yield) of the title compound as an oil.

$^{13}C$-NMR (75MHz, $CDCl_3$) δ166, 155, 153, 135, 132, 130, 128, 128, 125, 117, 114, 79, 66, 52, 48, 45, 32, 28.5, 29.5, 26, 19.

Example 67

(R)-N-[5-Methyl-8-(piperazin-1-yl)-1,2,3,4-tetrahydro-2-naphthyl]-4-morpholinobenzamide To a solution of (R)-N-[5-methyl-8-(4-tert-butyloxycarbonylpiperazin-1-yl)-1,2,3,4-tetrahydro-2-naphthyl]-4-morfolinobenzamide (4.2 g, 7.9 mmol) in methylene chloride (390 mL) at 5° C. was added trifluoroacetic acid (12 mL). The solution was the stirred at room temperature for 24 h and the solvent was evaporated in vacuo. The remains were partitioned between methylene chloride (250 mL) and a 5 M aqueous solution of sodium hydroxide (100 mL, pH 10–11). The organic phase was collected, and the aqueous phase was re-extracted with methylene chloride (100 mL). The combined organic phases were dried ($Na_2SO_4$), filtered and evaporated in vacuo. The crude product was purified on a silica gel column using methylene chloride/methanol/$NH_3$ (aq) (10:0.8:0.08) as the eluent to give 3.2 g (92% yield) of the title compound as an oil which crystallized (light brown crystals) by trituration in diethyl ether: mp 207–210° C.; $[α]_{20}^D$=−57° (c 0.5, $CHCl_3$); EIMS (70 eV) m/z (relative intensity) 434 (23, $M^+$).

Example 68

(R)-N-[5-Methyl-8-(4-methylpiperazin-1-yl)-1,2,3,4-tetrahydro-2-naphthyl]-4-chlorobenzamide To a solution of (R)-2-amino-5-methyl-8-(4-methylpiperazin-1-yl)-1,2,3,4-tetrahydronaphthalene (52 mg, 0.20 mmol) and triethylamine (1 mL, 7.7 mmol) in methylene chloride (10 mL) was added a solution of 4-chlorobenzoyl chloride (50 mg, 0.29 mmol) in methylene chloride (10 mL) and the reaction was stirred at 0° C. for 30 min. The stirring was continued for another 2 h at ambient temperature and then the solvent was evaporated in vacuo. The remains were purified on a silica gel column using ethyl acetate containing triethylamine (7.5%) as the eluent to give 50 mg (63% yield) of the title compound as white crystals: mp 210–212° C.; EIMS (70 eV) m/z (relative intensity) 397 (28, $M^+$).

Example 69

(R)-2-N,N-Dibenzylamino-8-bromo-1,2,3,4-tetrahydronaphthalene (R)-8-Bromo-2-amino-1,2,3,4-tetrahydronaphthalene hydrochloride (50 g, 0.19 mol) was partitioned between diethyl ether (700 mL) and a 2 M aqueous solution of NaOH (100 mL). The aqueous layer was extracted with diethyl ether (50 mL) and the combined organic phases were washed with brine (75 mL). The etheral layer was dried ($Na_2SO_4$) and the solvent was evaporated in vacuo giving 43.3 g of the free base. The base was slurried in acetonitrile (600 mL) and benzyl bromide (54 μL, 0.46 mol), potassium carbonate (66 g, 48 mol), potassium iodide (200 mg, 1 mmol) and an additional 100 mL of acetonitrile were added and the reaction mixture was heated to reflux. After stirring for 9 h the inorganic salts were filtered off followed by evaporation of the solvent in vacuo giving 91 g of a residue. The crude product was dissolved in diethyl ether (100 mL), cooled on ice and HCl in diethyl ether (200 mL, 200 mmol, 1 M) was slowly added. Hexane (1.2 L) was added to the slurry and the precipitate was filtered and washed with hexane (1 L). Diethyl ether (1.5 L) and a 2 M aqueous solution of NaOH (150 mL) were added and the mixture was stirred for 2 h. The phases were separated and the aqueous phase was re-extracted with diethyl ether (100 mL) and the combined organic layers was washed with brine (100 mL). The organic phase was dried ($Na_2SO_4$) and the solvent was evaporated in vacuo affording 73 g (94% yield) of the title compound as a yellow oil. An analytical sample was purified by preparative TLC on silica using chloroform/hexane (1:5) as the eluent; $[\alpha]_D^{22}$+134° (c 0.72, $CHCl_3$). EIMS (70 eV) m/z (relative intensity) 405 and 407 (6 and 9, $M^+$)

Example 70

(R)-2-N,N-Dibenzylamino-8-(4-methylpiperazin-1-yl)-1,2,3,4-tetrahydronaphthalene (R)-2-N,N-Dibenzylamino-8-bromo-1,2,3,4-tetrahydronaphthalene (48 g, 118 mmol) and 4-methylpiperazine (16 mL, 0.14 mol) were dissolved in toluene (450 mL) and flushed with argon. To the solution were added (R)-(+)-2,2'-bis(diphenyl)phosphino-1,1'-binaphthyl (5.5 g, 8.9 mmol), tris(dibenzylideneacetone) dipalladium(0) (3.4 g, 3.7 mmol) and sodium tert-butoxide (16 g, 0.17 mmol) and the reaction mixture was stirred at 85° C. for 3 h. Filtration through Celite using chloroform/methanol/conc. ammonia (95:5:0.5) as the eluent followed by evaporation of the solvent in vacuo gave 68 g of a crude product. Purification by column chromatography on a silica column using ethyl acetate/triethylamine (100:1) as the eluent gave 44 g (88% yield) of the title compound as a yellowish oil which crystallized after standing: mp 82–84° C.; EIMS (70 eV) m/z (relative intensity) 425 (26, $M^+$); $[\alpha]_D^{22}$+40° (c 0.57, $CHCl_3$).

Example 71

(R)-2-Amino-8-(4-methylpiperazin-1-yl)-1,2,3,4-tetrahydronaphthalene (R)-2-N,N-Dibenzylamino-8-(4-methylpiperazin-1-yl)-1,2,3,4-tetrahydronaphthalene (47 g, 0.11 mol) was dissolved in acetic acid (480 mL) and charged into a Büchi glass autoclave (1 L). To the solution was added 10% Pd/C (9.4 g, containing 50% $H_2O$). The reaction mixture was stirred at 70° C. and at 5 bar hydrogen pressure for 10 h. The catalyst was removed by filtration and the solvent was evaporated in vacuo giving 65 of the crude material as an oil. The crude material was used in the next step without isolation of the free amine.

An analytical sample was obtained by partitioning the crude product between methylene chloride and aqueous $NH_3$. The phases were separated and the organic phase was washed with brine, dried ($Na_2SO_4$) and purified on a silica gel column using chloroform/methanol/conc. $NH_3$ (90:9:0.5) as the eluent giving the title compound as a brownish oil: EIMS (70 eV) m/z (relative intensity) 245 (10, $M^+$); $[\alpha]_D^{25}$-2.7° (c 1.0, $CHCl_3$).

Example 72

(R)-2-Amino-5-bromo-8-(4-methylpiperazin-1-yl)-1,2,3,4-tetra-hydronaphthalene (R)-2-Amino-8-(4-methylpiperazin-1-yl)-1,2,3,4-tetrahydronaphthalene (27 g, 0.11 mmol) and sodium acetate (9.6 g, 0.12 mol) were dissolved in acetic acid (145 mL). To the solution was added bromine (6.0 mL, 0.12 mmol), dissolved in acetic acid (145 mL), during 13 min and at a maximum temperature of 23° C. After completed addition the reaction mixture was stirred at room temperature for 1.25 h. The solvent was evaporated in vacuo and additional acetic acid (60 mL) was added and evaporated. The residue was partitioned between ethyl acetate (300 mL) and $H_2O$ (100 mL) and cooled on ice. The pH was adjusted to 11–12 by the addition of aqueous NaOH (45%) and the phases were separated. The aqueous layer was extracted with ethyl acetate (2×200 mL) and the combined organic phases were washed with brine (80 mL) and dried ($Na_2SO_4$). The solvent was evaporated in vacuo giving 27 g of the title compound as a brownish oil: EIMS (70 eV) m/z (relative intensity) 324 and 325 (22 and 17, $M^+$); $[\alpha]_D^{22}$+3.5° (c 0.23, $CHCl_3$).

Example 73

(R)-2-N,N-Dibenzylamino-5-bromo-8-(4-methylpiperazin-1-yl)-1,2,3,4-tetrahydronaphthalene (R)-2-Amino-5-bromo-8-(4-methylpiperazin-1-yl)-1,2,3,4-tetrahydronaphthalene (35 g, 0.10 mol) was dissolved in methanol (250 mL) and flushed with nitrogen. Benzaldehyde (11 mL, 0.10 mol) and acetic acid (18 mL, 0.31 mol) were added and the solution was stirred for 1 h at room temperature. Sodium cyanoborohydride (6.9 g, 0.10 mol) was dissolved in methanol (100 mL) and added during 8 min. The reaction mixture was stirred at 40° C. for 1.5 h. An additional amount of benzaldehyde (21 mL, 208 mmol) and $NaCNBH_3$ (3.5 g, 52 mmol) was added portionwise during 48 h. The reaction mixture was stirred for another 7 h, quenched with acetic acid (27 mL, 0.49 mol) and stirred at room temperature for 15 h. To the solution was added aqueous NaOH (30 mL, 45%) and after 3.5 h the solvent was evaporated in vacuo. The residue was partitioned between ethyl acetate (400 mL) and $H_2O$ (100 mL) and pH was adjusted to 11 with aqueous NaOH (14 mL, 45%). The phases were separated and the aqueous phase was re-extracted with ethyl acetate (150 mL) and the combined organic layer was washed with brine (100 mL). The organic phase was dried ($Na_2SO_4$) and the solvent was evaporated in vacuo giving 68 g of a crude product. Purification by column chromatography on silica using ethyl acetate/triethylamine (100:1) as the eluent gave 45 g (85% yield) of the title compound as a yellowish oil: EIMS (70 eV) m/z (relative intensity) 504 and 505 (0.8 and 0.6, $M^+$); $[\alpha]_D^{22}$+25° (c 1.09, $CHCl_3$).

Example 74

(R)-2-N,N-Dibenzylamino-5-methyl-8-(4-methylpiperazin-1-yl)-1,2,3,4-tetrahydronaphthalene (R)-2-N,N-Dibenzylamino-5-bromo-8-(4-methylpiperazin-1-yl)-1,2,3,4-tetrahydronaphthalene (16 g, 0.31 mol) was dissolved in freshly distilled tetrahydrofuran (300 mL) and cooled to −78° C. under argon. To the solution was added n-butyl lithium (19 mL, 1.6 M in hexane, 0.31 mol,) dropwise during 45 min at a maximum temperature of −76° C. The dark green solution was stirred for an additional 20 min. A solution of methyl iodide (1.9 mL, 0.31 mol) in freshly distilled tetrahydrofuran (10 mL) was added dropwise during 25 min at a maximum temperature of −74° C. making the green color disappear. The reaction mixture was stirred at −78° C. for 50 min and at 0° C. for 50 min. The reaction was quenched with i-propylalcohol (3 mL) and the solvent was evaporated in vacuo. The residue was partitioned between ethyl acetate (300 mL) and $H_2O$ (30 mL) and the phases were separated and the organic layer was washed with brine (30 mL). After drying ($Na_2SO_4$), and evaporation of the solvent in vacuo, 15 g of a crude product was obtained. Purification by column chromatography on silica using ethyl acetate/triethylamine (100:1) as the eluent afforded 11 g (82% yield) of the title compound as a brown oil: EIMS (70 eV) m/z (relative intensity) 439 (5, $M^+$); $[\alpha]_D^{22}$ +86° (c 0.05, $CHCl_3$).

Example 75

(R)-2-Amino-5-methyl-8-(4-methylpiperazin-1-yl)-1,2,3,4-tetrahydro-naphthalene (R)-2-N,N-Dibenzylamino-5-methyl-8-(4-methylpiperazin-1-yl)-1,2,3,4-tetrahydronaphthalene (28 g, 64 mmol) was dissolved in acetic acid (280 mL) and charged into a Büchi glass autoclave (1 L). 10% Palladium on charcoal (2.8 g, containing 50% $H_2O$) was added. The reaction mixture was stirred at 70° C. and at 5 bar hydrogen pressure for 3.5 h. The catalyst was filtered off and the solvent was evaporated in vacuo. The residue was partitioned between ethyl acetate (400 mL) and water (100 mL) and cooled on an ice-bath. The pH was adjusted to 12 by addition of aqueous NaOH (45%) and the phases were separated. The aqueous phase was re-extracted with ethyl acetate (2×100 mL) and the combined organic layer was washed with brine (50 mL) and dried ($Na_2SO_4$). Evaporation of the solvent in vacuo gave 18 g (99% yield) of the title compound as a brown oil. EIMS (70 eV) m/z (relative intensity) 259 (34, $M^+$); $[\alpha]_D^{22}$ −1.1° (c 0.09, $CHCl_3$).

Example 76

Salts of (R)-N-[5-Methyl-8-(4-methylpiperazin-1-yl)-1,2,3,4-tetrahydro-2-naphthyl]-4-morpholinobenzamide.

All melting points were determined using Differential Scanning Calorimetry (DSC). The temperature scanning rate was 10° C. per minute starting from room temperature. The samples were investigated in aluminum-pans with loose lids under nitrogen.

(R)-N-[5-Methyl-8-(4-methylpiperazin-1-yl)-1,2,3,4-tetrahydro-2-naphthyl]-4-morpholinobenzamide Hydrogen (2S,3S)-Tartrate.

(R)-N-[5-Methyl-8-(4-methylpiperazin-1-yl)-1,2,3,4-tetrahydro-2-naphthyl]-4-morpholinobenzamide (150 mg, 0.33 mmol) was dissolved in tetrahydrofuran (3 mL) by heating and D-(−)-tartaric acid (110 mg, 0.69 mmol), dissolved in tetrahydrofuran (3 mL), was added dropwise. The white precipitate was filtered and washed with tetrahydrofuran to give 180 mg (86% yield). The crude salt (170 mg) was recrystallized from a 3% aqueous acetone solution (30 mL) and after standing for 3 h at room temperature the flask was put in the refrigerator for 65 h. The solid was filtered and washed with cold acetone to give 120 mg (61% yield) of white crystal: mp 142–148° C. Anal. Calcd. for $C_{27}H_{36}N_4O_2 \times C_4H_6O_6 \times 2H_2O$: C, 58.7; H, 7.0; N, 8.8. Found: C, 58.6; H, 7.1; N, 8.8.

Example 77

(R)-N-[5-Methyl-8-(4-methylpiperazin-1-yl)-1,2,3,4-tetrahydro-2-naphthyl]-4-morpholinobenzamide Hydrogen (2R,3R)-Tartrate (R)-N-[5-Methyl-8-(4-methylpiperazin-1-yl)-1,2,3,4-tetrahydro-2-naphthyl]-4-morpholinobenzamide (150 mg, 0.33 mmol) was dissolved in tetrahydrofuran (3 mL) by heating and L-(+)-tartaric acid (110 mg, 0.69 mmol), dissolved in tetrahydrofuran (3 mL), was added dropwise. The white precipitate was filtered and washed with tetrahydrofuran to give 180 mg (86% yield). The crude salt (180 mg) was recrystallized from a 3% aqueous acetone solution (48 mL) (some insoluable material was filtered) and after standing overnight at room temperature the solid was filtered to give 8 mg. The solvent was removed from the mother liquor by using a gentle stream of nitrogen so that 4 mL remained. The flask was allowed to stand at room temperature for 65 h and was then put in the refrigerator for 5 h. The solid was filtered and washed with cold acetone to give 61 mg (29% yield) of white crystal: mp 120–130° C. Anal. Calcd. for $C_{27}H_{36}N_4O_2 \times C_4H_6O_6 \times 2H_2O$: C, 58.7; H, 7.0; N, 8.8. Found: C, 58.9; H, 7.1; N, 8.6.

Example 78

(R)-N-[5-Methyl-8-(4-methylpiperazin-1-yl)-1,2,3,4-tetrahydro-2-naphthyl]-4-morpholinobenzamide Benzenesulfonate.

(R)-N-[5-Methyl-8-(4-methylpiperazin-1-yl)-1,2,3,4-tetrahydro-2-naphthyl]-4-morpholinobenzamide (100 mg, 0.22 mmol) was dissolved in tetrahydrofuran (2 mL) by heating and benzenesulfonic acid (40 mg, 0.24 mmol), dissolved in tetrahydrofuran (4 mL), was added dropwise. Diethyl ether was added and the resulting oil was titurated. The solid was filtered and washed with diethyl ether to give a white solid that was stored in an exicator over blue gel: mp >250° C. Anal. Calcd. for $C_{27}H_{36}N_4O_2 \times C_6H_6O_3S \times H_2O$: C, 63.4; H, 6.8; N, 9.0. Found: C, 63.1; H, 7.0; N, 8.7.

Example 79

(R)-N-[5-Methyl-8-(4-methylpiperazin-1-yl)-1,2,3,4-tetrahydro-2-naphthyl]-4-morpholinobenzamide Hydrogen 1,2-Ethanedisulfonate.

(R)-N-[5-Methyl-8-(4-methylpiperazin-1-yl)-1,2,3,4-tetrahydro-2-naphthyl]-4-morpholinobenzamide (100 mg, 0.22 mmol) was dissolved in tetrahydrofuran (3 mL) by heating and 1,2-ethanedisulfonic acid dihydrate (55 mg, 0.24 mmol), dissolved in tetrahydrofuran (2 mL), was added dropwise. Diethyl ether (2 mL) was added, the solid was filtered and washed with tetrahydrofuran/diethyl ether to give a white solid that was stored in an exicator over blue gel: mp 220° C. (decom.). Anal. Calcd. for $C_{27}H_{36}N_4O_2 \times C_2H_6O_6S_2 \times 4H_2O$: C, 48.9; H, 7.1; N, 7.9. Found: C, 49.1; H, 6.8; N, 7.6.

Example 80

(R)-N-[5-Methyl-8-(4-methylpiperazin-1-yl)-1,2,3,4-tetrahydro-2-naphthyl]-4-morpholinobenzamide Hydrogen Maleate (R)-N-[5-Methyl-8-(4-methylpiperazin-1-yl)-1,2,3,4-tetrahydro-2-naphthyl]-4-morpholinobenzamide (100 mg, 0.22 mmol) was dissolved in tetrahydrofuran (2 mL) by heating and maleic acid (29 mg, 0.24 mmol), dissolved in tetrahydrofuran (1 mL), was added dropwise. Diethyl ether (5 mL) was added to the clear solution to give an oil. The solvent was decanted and the resulting oil was titurated from diethyl ether. The solid was filtered and washed with diethyl ether to give a white solid that was stored in an exicator over blue gel: mp 160° C. (decom.). Anal. Calcd. for $C_{27}H_{36}N_4O_2 \times C_4H_4O_4 \times H_2O$: C, 63.8; H, 6.9; N, 9.6. Found: C, 63.7; H, 7.2; N, 9.3.

Example 81

(R)-N-[5-Methyl-8-(4-methylpiperazin-1-yl)-1,2,3,4-tetrahydro-2-naphthyl]-4-morpholinobenzamide Hydrogen Sulfate (R)-N-[5-Methyl-8-(4-methylpiperazin-1-yl)-1,2,3,4-tetrahydro-2-naphthyl]-4-morpholinobenzamide (100 mg, 0.22 mmol) was dissolved in tetrahydrofuran (2 mL) by heating and sulfuric acid (25 mg, 0.24 mmol), dissolved in tetrahydrofuran (1 mL), was added dropwise. The white precipitate was filtered and washed with tetrahydrofuran to give 110 mg (89% yield). The crude salt (80 mg) was recrystallized from $H_2O$ (12 mL) and allowed to stand in the refrigerator over night. The solid was filtered and washed with cold $H_2O$ to give 28 mg (31% yield) a white solid: nip 230° C. (decom.). Anal. Calcd. for $C_{27}H_{36}N_4O_2 \times H_2O_4S \times H_2O$: C, 57.4; H, 7.1; N, 9.9. Found: C, 57.7; H, 7.4; N, 9.9.

Example 82

(R)-N-[5-Methyl-8-(4-methylpiperazin-1-yl)-1,2,3,4-tetrahydro-2-naphthyl]-4-morpholinobenzamide Gluconate (R)-N-[5-Methyl-8-(4-methylpiperazin-1-yl)-1,2,3,4-tetrahydro-2-naphthyl]-4-morpholinobenzamide (100 mg, 0.22 mmol) was dissolved in ethanol (3 mL) and a 50% aqueous D-gluconic acid solution (80 µL, 0.24 mmol) was added dropwise. The solvent was removed in vacuo to give a white viscous oil. The crude oil was recrystallized from a 5% $H_2O$ in acetone solution (3 mL) and a 10% $H_2O$ in acetone solution (3 mL), decanted, then allowed to stand at room temperature for 65 h. The solid was filtered and washed with a cold 3% $H_2O$ in acetone solution to give 95 mg (65% yield) of a white solid: mp 130-140° C. Anal. Calcd. for $C_{27}H_{36}N_4O_2 \times C_6H_{12}O_7 \times H_2O$: C, 59.8; H, 7.6; N, 8.5. Found: C, 60.0; H, 7.4; N, 8.3.

Example 83

(R)-N-[5-Methyl-8-(4-methylpiperazin-1-yl)-1,2,3,4-tetrahydro-2-naphthyl]-4-morpholinobenzamide Hydrogen Succinate (R)-N-[5-Methyl-8-(4-methylpiperazin-1-yl)-1,2,3,4-tetrahydro-2-naphthyl]-4-morpholinobenzamide (100 mg, 0.22 mmol) was dissolved in tetrahydrofuran (2 mL) by heating and succinic acid (56 mg, 0.46 mmol), dissolved in tetrahydrofuran (2 mL), was added dropwise. Diethyl ether (4 mL) was added until the solution was cloudy. The solution was heated to reflux and set aside to cool. The solid was filtered to give 42 mg (34% yield) of a white solid that was stored in an exicator over blue gel: mp 150° C. (decom.).

Example 84

(R)-N-[5-Methyl-8-(4-methylpiperazin-1-yl)-1,2,3,4-tetrahydro-2-naphthyl]-4-morpholinobenzamide Methansulfonate (R)-N-[5-Methyl-8-(4-methylpiperazin-1-yl)-1,2,3,4-tetrahydro-2-naphthyl]-4-morpholinobenzamide (100 mg, 0.22 mmol) was dissolved in tetrahydrofuran (15 mL) and methanesulfonic acid (42 mg, 0.44 mmol), dissolved in tetrahydrofuran (5 mL), was added dropwise. The solvent was removed in vacuo to give a white solid that was recrystallized from acetone (5 mL) and then from a 15% $H_2O$ in acetone solution (7 mL). The crystals were filtered to give 37 mg (31% yield) of light yellow crystals that was stored in an exicator over blue gel: mp 250° C. (decom.). Anal. Calcd. for $C_{27}H_{36}N_4O_2 \times CH_4O_3S \times 2H_2O$: C, 57.9; H, 7.6; N, 9.7. Found: C, 58.1; H, 7.4; N, 9.6.

Example 85

(R)-N-[5-Methyl-8-(4-methylpiperazin-1-yl)-1,2,3,4-tetrahydro-2-naphthyl]-4-morpholinobenzamide Hydrogen (S)-Malate (R)-N-[5-Methyl-8-(4-methylpiperazin-1-yl)-1,2,3,4-tetrahydro-2-naphthyl]-4-morpholinobenzamide (100 mg, 0.22 mmol) was dissolved in tetrahydrofuran (20 mL) and L-(−)-malic acid (59 mg, 0.44 mmol), dissolved in tetrahydrofuran (3 mL), was added dropwise. The precipitate was filtered and the solid material was recrystallized from a 15% $H_2O$ in acetone solution (7 mL). The solid was filtered to give 100 mg (77% yield) of white crystals: mp 200° C. (decom.). Anal. Calcd. for $C_{27}H_{36}N_4O_2 \times C_4H_6O_5 \times 2H_2O$: C, 57.9; H, 7.6; N, 9.7. Found: C, 58.1; H, 7.4; N, 9.6.

Example 86

(R)-N-[5-Methyl-8-(4-methylpiperazin-1-yl)-1,2,3,4-tetrahydro-2-naphthyl]-4-morpholinobenzamide Dihydrogen Citrate (R)-N-[5-Methyl-8-(4-methylpiperazin-1-yl)-1,2,3,4-tetrahydro-2-naphthyl]-4-morpholinobenzamide (100 mg, 0.22 mmol) was dissolved in tetrahydrofuran (15 mL) and citric acid (51 mg, 0.27 mmol), dissolved in 10% $H_2O$ in tetrahydrofuran (5 mL), was added dropwise. The solid material was filtered and recrystallized from a 20% $H_2O$ in ethanol (5 mL). The solid was filtered to give 88 mg (62% yield) of white crystals: mp 160° C. (decom.). Anal. Calcd. for $C_{27}H_{36}N_4O_2 \times C_6H_8O_7 \times 2H_2O$: C, 57.9; H, 7.6; N, 9.7. Found: C, 58.1; H, 7.4; N, 9.6.

Example 87

(R)-N-[5-Methyl-8-(4-methylpiperazin-1-yl)-1,2,3,4-tetrahydro-2-naphthyl]-4-morpholinobenzamide Hydrochloride (R)-N-[5-Methyl-8-(4-methylpiperazin-1-yl)-1,2,3,4-tetrahydro-2-naphthyl]-4-morpholinobenzamide (100 mg, 0.22 mmol) was dissolved in anhydrous tetrahydrofuran (15 mL) and HCl in anhydrous diethyl ether (4 M) was added dropwise until the solution was acidic. The white precipitate was filtered and washed with diethyl ether to give the title compound as white crystals.

PHARMACOLOGY

Electrical Field Stimulation of [$^3$H]-5-HT Release from Occipital Cortex of Guinea Pigs

[$^3$H]-5-HT is released by electrical field stimulation from slices of occipital cortex of guinea pigs which have been pre-incubated with [³H]-5-HT. This release is similar to that caused by nerve stimulation, i.e. exocytotical release from serotonergic nerve terminals, depending on the presence of $Ca^{2+}$ in the incubation medium. The 5-HT release is regulated at the level of the nerve terminals by autoreceptors, in the guinea pigs (like in humans) belonging to the h5-$HT_{1B}$ receptor subtype. Thus, agonists of h5-$HT_{1B}$ receptors reduce the amount of [3H]-5-HT released by field stimulation whereas the release is increased by antagonists of this receptor type. Testing compounds with this method is accordingly a convenient screening technique for determining the potency and functional effect of new h5-$HT_{1B}$ receptor agonists and antagonists.

Methods and Materials

Buffer Composition (mM)

$NaHCO_3$ (25), $NaH_2PO_4.H_2O$ (1.2), NaCl (117), KCl(6), $MgSO_4 \times 7H_2O$(1.2), $CaCl_2$(1.3), EDTA $Na_2$(0.03). The buffer is gassed for at least 30 min before use. The pH of the buffer is about 7.2 at room temperature but it rises to about 7.4 at 37° C.

Preparation of Occipital Cortical Slices

Guinea pigs (200-250 g) were decapitated and the whole brain was removed. The occipital cortex was dissected and cut to slices 0.4×4 mm with McIlwain chopper machine. The white part of the tissue should be removed carefully with a tweezers before slicing. The slices were incubated in 5 ml buffer in the presence of 5 mM pargyline chloride. After incubation with 0.1 mM [³H]-5-HT for another 30 min the slices were transferred to a test tube and washed three times with same volume buffer. The slices were transferred to the superfusion chambers with a plastic pipette and were washed for 40 min with the buffer in the presence of uptake inhibitor citalopram 2.5 µM with a flow 0.5 ml/min.

Electrical Stimulation of 5-HT Release

The superfused buffer was collected in 2 mL fractions. The slices were stimulated by electricity with a train of pulses of frequency 3 Hz, duration 2 ms and current 30 mA for 3 min at the 4th and 13th fractions. The tested drugs were added from the 8th fraction to the end of experiment.

Results

A first electrical (orK+) stimulation results in a standard amount of [³H]-5-HT released ($S_1$). Between the first and a second stimulation the H5-$HT_{1B}$ antagonist is added to the media, which results in a dose-dependent increase of the release ($S_2$) after the second stimulation. See FIG. 1.

The $S_2/S_1$ ratio, which is the percent of released [³H]-5-HT at the second stimulation ($S_2$) divided by that of the first stimulation ($S_1$). was used to estimate drug effects on transmitter release.

What is claimed is:
1. A compound of the formula I

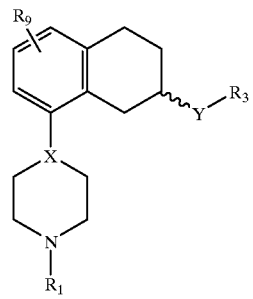

wherein
X is CH;
Y is $NR_2CH_2$, $CH_2$—$NR_2$, $NR_2$—CO, CO—$NR_2$ or $NR_2SO_2$ wherein $R_2$ is H or $C_1$–$C_6$ alkyl;
$R_1$ is H, $C_1$–$C_6$ alkyl or $C_3$–$C_6$ cycloalkyl;
$R_3$ is $C_1$–$C_6$ alkyl, $C_3$–$C_6$ cycloalkyl or $(CH_2)_n$-aromatic ring, wherein the aromatic ring is phenyl or a heteroaromatic ring containing one or two heteroatoms selected from the group consisting of N, O and S and wherein the aromatic ring may be mono- or di-substituted with $R_4$ and/or $R_5$;
wherein $R_4$ is H, $C_1$–$C_6$ alkyl, $C_3$–$C_6$ cycloalkyl, halogen, CN, $CF_3$, OH, $C_1$–$C_6$ alkoxy, $NR_6R_7$, $OCF_3$, $SO_3CH_3$, $SO_3CF_3$, $SO_2NR_6R_7$, phenyl-$C_1$–$C_6$ alkyl, phenoxy, $C_1$–$C_6$ alkyl phenyl, an optionally substituted heterocyclic ring containing one or two heteroatoms selected from the group consisting of N, O, S, SO and $SO_2$ wherein the substituent (s) is (are) selected from the group consisting of $C_1$–$C_6$ alkyl, $C_3$–$C_6$ cycloalkyl and phenyl-$C_1$–$C_6$ alkyl, an optionally substituted heteroaromatic ring containing one or two heteroatoms selected from the group consisting of N, O and S wherein the substituent (s) is (are) selected from the group consisting of $C_1$–$C_6$ alkyl, $C_3$–$C_6$ cycloalkyl and phenyl-$C_1$–$C_6$ alkyl, or $COR_8$;
wherein $R_6$ is H, $C_1$–$C_6$ alkyl or $C_3$–$C_6$ cycloalkyl; $R_7$ H, $C_1$–$C_6$ alkyl or $C_3$–$C_6$ cycloalkyl; and $R_8$ is $C_1$–$C_6$ alkyl, $C_3$–$C_6$ cycloalkyl, $CF_3$, $NR_6R_7$, phenyl, a heteroaromatic ring containing one or two heteroatoms selected from the group consisting of N, O and S or a heterocyclic ring containing one or two heteroatoms selected from the group consisting of N, O, S, SO and $SO_2$;
wherein $R_5$ is H, OH, $CF_3$, $OCF_3$, halogen, $C_1$–$C_6$ alkyl or $C_1$–$C_6$ alkoxy;
n is 0–4;
$R_9$ is $C_1$–$C_6$ alkyl, $C_3$–$C_6$ cycloalkyl, $OCF_3$, $OCHF_2$, $OCH_2F$, halogen, CN, $CF_3$. OH, $C_1$–$C_6$ alkoxy, $C_1$–$C_6$ alkoxy—$C_1$–$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from the group consisting of N, O and S, wherein the substituent (s) is (are) $C_1$–$C_6$ alkyl; or $COR_8$; wherein $R_6$, $R_7$ and $R_8$ are as defined above, wherein the compound is an (R)-enantiomer, an (S)-enantiomer, or a racemate in the form of a free base or a pharmaceutically acceptable salt or solvate thereof.
2. The compound according to claim 1 wherein Y is $NR_2$—CO or CO—$NR_2$.

3. The compound according to claim 1 wherein $R_1$ is H or $C_1$–$C_6$ alkyl.

4. The compound according to claim 1 wherein $R_2$ is $(CH_2)_n$-aromatic ring.

5. The compound according to claim 4 wherein the aromatic ring of substituent $R_3$ is substituted with $R_4$, and $R_4$ is an optionally substituted heterocyclic or heteroaromatic ring containing one or two heteroatoms selected from the group consisting of N, O and S; or $COR_8$.

6. The compound according to claim 4 or 5 wherein n is 0.

7. The compound according to claim 5 wherein $R_8$ is a heterocyclic ring containing two heteroatoms selected from N and O.

8. The compound according to claim 1 wherein $R_9$ is $C_1$–$C_6$ alkyl, $OCHF_2$, halogen or $C_1$–$C_6$ alkoxy.

9. The compound according to claim 1 wherein Y is $NR_2CO$ and $R_9$ is $C_1$–$C_6$ alkoxy.

10. The compound according to claim 5 wherein Y is $NR_2CO$, $R_4$ is morpholino or $COR_8$ and $R_9$ is $C_1$–$C_6$ alkoxy.

11. The compound according to claim 1 wherein Y is $NR_2CO$ and $R_9$ is $C_1$–$C_6$ alkyl.

12. The compound according to claim 1 wherein Y is $NR_2CO$, $R_1$ is H, $R_3$ is $(CH_2)_n$-aromatic ring and $R_9$ is $C_1$–$C_6$ alkyl.

13. The compound according to claim 5 wherein Y is $NR_2CO$, $R_4$ is morpholino or $COR_8$ and $R_9$ is $C_1$–$C_6$ alkyl.

14. A pharmaceutical formulation comprising as active ingredient a therapeutically effective amount of the compound of claim 1, wherein the compound is an enantiomer or racemate in the form of a free base or a pharmaceutically acceptable salt or solvate thereof optionally in association with diluents, excipients or inert carriers.

15. A method for the treatment of 5-hydroxytryptamine-mediated disorders, comprising administering to a patient in need of such treatment a therapeutically 16. A method for the treatment of mood disorders, anxiety disorders, personality disorders, obesity, anorexia, bulimia, premenstrual syndrome, sexual disturbances, alcoholism, tobacco abuse, autism, attention deficit, hyperactivity disorder, migraine, memory disorders, pathological aggression, schizophrenia, endocrine disorders, stroke, dyskinesia, Parkinson's disease, thermoregulatory disorders, pain, hypertension, urinary incontinence or vasospasm; or for inhibition of tumor growth, comprising administering to a patient in need of such treatment a therapeutically effective amount of the pharmaceutical formulation of claim 14.

17. A method for the treatment of 5hydroxytryptamine-mediated disorders in the central nervous system, comprising administering to a patient in need of such treatment a therapeutically effective amount of the pharmaceutical formulation of claim 14.

18. A method for the treatment of 5-hydroxytryptamine-mediated disorders in the central nervous system and/or urinary incontinence or vasospasm, or for inhibition of tumor growth, comprising administering to a patient in need of such treatment a therapeutically effective amount of a compound defined in claim 1.

19. The method according to claim 18 for the treatment of mood disorders, anxiety disorders, personality disorders, obesity, anorexia, bulimia, premenstrual syndrome, sexual disturbances, alcoholism, tobacco abuse, autism, attention deficit, hyperactivity disorder, migraine, memory disorders, pathological aggression, schizophrenia, endocrine disorders, stroke, dyskinesia, Parkinson's disease, thermoregulatory disorders, pain, or hypertension.

20. A method for the treatment of 5-hydroxytryptamine-mediated disorders which require treatment with a 5-$HT_{1B}$ antagonist, comprising administering to a patient in need of such treatment a therapeutically effective amount of a compound defined in claim 1.

21. A process for the preparation of the compound of formula I according to claim 1, comprising:

A(i). acylation, in the case wherein $R_1$–$C_6$ alkyl or $C_3$–$C_6$ cycloalkyl, Y is $NR_2CO$, $R_2$ is hydrogen, X, $R_3$ and $R_9$ are as defined in claim 1 with the exception of when $R_9$ is a substituent that is susceptible to certain acylating agents, of a compound of formula A

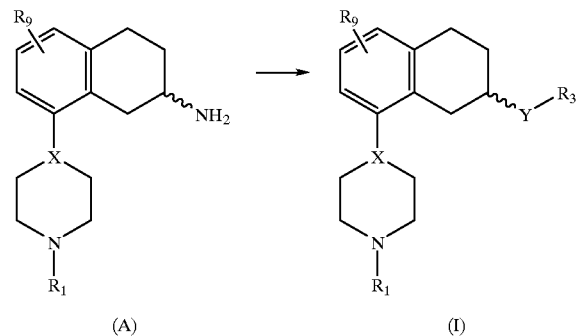

with an activated carboxylic acid $R_3$-COL wherein L is a leaving group or with a carboxylic acid $r_3$COOH and an activating reagent;

A(ii). acylation, in the case wherein $R_1$ is hydrogen, Y is $NR_2CO$, $R_2$ is hydrogen, $R_c$ is a protecting group and X, $R_3$ and $R_9$ are as defined in claim 1 with the exception of when $R_9$ is a substituent that is susceptible to certain acylating agents, of a compound of formula B

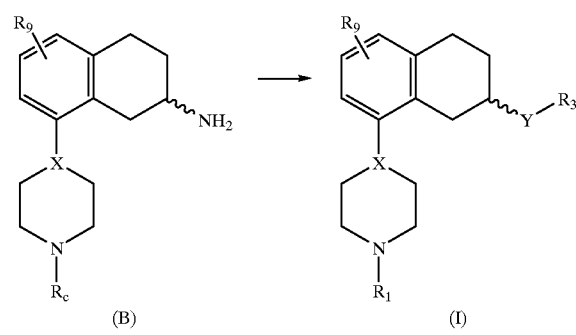

with an activated carboxylic acid $R_3$-COL wherein L is a leaving group or with a carboxylic acid $R_3$-COOH and an activating reagent, and removing the protecting group $R_c$.

22. A compound of the formula

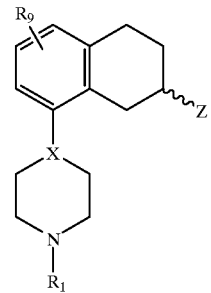

wherein

X is CH;

Z is $NH_2$ or COOH;

$R_1$ is H, $C_1$–$C_6$ alkyl or $C_3$–$C_6$ cycloalkyl;

$R_9$ is $C_1$–$C_6$ alkyl, $C_3$–$C_6$ cycloalkyl, $OCF_3$, $OCHF_2$, $OCH_2F$, halogen, CN, $CF_3$, OH, $C_1$–$C_6$ alkoxy, $C_1$–$C_6$ alkoxy-$C_1$–$C_6$ alkyl, $NR_6R_7$, $SO_3CH_3$, $SO_3CF_3$, $SO_2NR_6R_7$, an unsubstituted or substituted heterocyclic or heteroaromatic ring containing one or two heteroatoms selected from N and O, wherein the substituent (s) is (are) $C_1$–$C_6$ alkyl; or $COR_8$; wherein $R_6$ is H, $C_1$–$C_6$ alkyl or $C_3$–$C_6$ cycloalkyl;

$R_7$ is H, $C_1$–$C_6$ alkyl or $C_3$–$C_6$ cycloalkyl; and $R_8$ is $C_1$–$C_6$ alkyl, $C_3$–$C_6$ cycloalkyl, $CF_3$, $NR_6R_7$, phenyl, a heteroaromatic ring containing one or two heteroatoms selected from the group consisting of N, O and S or a heterocyclic ring containing one or two heteroatoms selected from the group consisting of N, O, S, SO and $SO_2$ wherein $R_6$ and $R_7$ are as defined above.

* * * * *

UNITED STATES PATENT AND TRADEMARK OFFICE
CERTIFICATE OF CORRECTION

PATENT NO.    : 6,410,532 B2
DATED         : June 25, 2002
INVENTOR(S)   : Berg et al.

It is certified that error appears in the above-identified patent and that said Letters Patent is hereby corrected as shown below:

Column 67,
Line 58, delete "(orK+)" and substitute therefor -- (or $K^+$) --.
Line 65, delete "." and substitute therefor -- , --.

Column 68,
Line 32, insert -- phenyl, -- after "$SO_2NR_6R_7$, --.
Line 44, insert -- is -- after "$R_7$".
Line 56, delete "." and substitute therefor -- , --.

Column 69,
Line 3, delete "$R_2$" and substitute therefor -- $R_3$ --.
Line 10, delete "o" and substitute therefor -- 0 --.
Line 35, insert -- effective amount of the pharmaceutical formulation of claim 14. -- after "therapeutically".
Line 47, insert a hyphen between "5" and "hydroxytryptamine".

Column 70,
Line 9, delete "susuceptible" and substitute therefor -- susceptible --.
Line 27, delete "$r_3COOH$" and substitute therefor -- $R_3$-COOH --.

Signed and Sealed this

Third Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,410,532 B2  Page 1 of 1
DATED : June 25, 2002
INVENTOR(S) : Berg et al.

It is certified that error appears in the above-identified patent and that said Letters Patent is hereby corrected as shown below:

<u>Title page,</u>
Item [75], delete "Mats Linderberg and Bengt Ulff" as inventors.

Signed and Sealed this

First Day of July, 2003

JAMES E. ROGAN
*Director of the United States Patent and Trademark Office*